US010538591B2

(12) United States Patent
Viapiano et al.

(10) Patent No.: US 10,538,591 B2
(45) Date of Patent: Jan. 21, 2020

(54) ANTI-FIBULIN-3 ANTIBODIES AND USES THEREOF

(71) Applicant: THE BRIGHAM AND WOMEN'S HOSPITAL, INC., Boston, MA (US)

(72) Inventors: Mariano S. Viapiano, Syracuse, NY (US); Nandhu Mohan Sobhana, Syracuse, NY (US); Ennio Antonio Chiocca, Weston, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 15/124,826

(22) PCT Filed: Mar. 10, 2015

(86) PCT No.: PCT/US2015/019639
§ 371 (c)(1),
(2) Date: Sep. 9, 2016

(87) PCT Pub. No.: WO2015/138411
PCT Pub. Date: Sep. 17, 2015

(65) Prior Publication Data
US 2017/0015757 A1  Jan. 19, 2017

Related U.S. Application Data

(60) Provisional application No. 61/950,410, filed on Mar. 10, 2014.

(51) Int. Cl.
| | | |
|---|---|---|
| C07K 16/30 | (2006.01) | |
| C07K 16/22 | (2006.01) | |
| A61K 39/395 | (2006.01) | |
| A61K 31/495 | (2006.01) | |
| A61K 31/166 | (2006.01) | |
| A61K 31/17 | (2006.01) | |
| A61K 31/175 | (2006.01) | |
| A61K 31/475 | (2006.01) | |
| A61K 49/00 | (2006.01) | |
| A61K 45/06 | (2006.01) | |
| C12N 5/0783 | (2010.01) | |
| A61K 39/00 | (2006.01) | |

(52) U.S. Cl.
CPC ............ *C07K 16/30* (2013.01); *A61K 31/166* (2013.01); *A61K 31/17* (2013.01); *A61K 31/175* (2013.01); *A61K 31/475* (2013.01); *A61K 31/495* (2013.01); *A61K 39/3955* (2013.01); *A61K 45/06* (2013.01); *A61K 49/0021* (2013.01); *C07K 16/22* (2013.01); *C07K 16/3053* (2013.01); *C12N 5/0636* (2013.01); *C12N 5/0646* (2013.01); *A61K 2039/505* (2013.01); *A61K 2039/5158* (2013.01); *A61K 2039/54* (2013.01); *A61K 2039/545* (2013.01); *C07K 2317/24* (2013.01); *C07K 2317/34* (2013.01); *C07K 2317/622* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 6,593,104 B1 | 7/2003 | Stone et al. |
| 2003/0105000 A1* | 6/2003 | Pero ........................ A61K 38/06 514/19.3 |
| 2004/0044187 A1 | 3/2004 | Sato et al. |
| 2006/0094054 A1 | 5/2006 | Schiemann et al. |
| 2008/0292619 A1 | 11/2008 | Sehara et al. |

FOREIGN PATENT DOCUMENTS

WO  02072138 A1  9/2002

OTHER PUBLICATIONS

Gura (Science, 1997, 278:1041-1042) (Year: 1997).*
Kaiser (Science, 2006, 313: 1370) (Year: 2006).*
Chames et al. (British J. of Pharmacology, 2009, 157, 220-233) (Year: 2009).*
Girmens et al. (Intractable & Rare Diseases Res. 2012, 1(3): 103-114) (Year: 2012).*
Lipowska-Bhalla et al. (Cancer Immunol. Immunotherapy 2012 61:953-962) (Year: 2012).*
Rudikoff et al. (PNAS USA, 1982, 79: 1979-1983) (Year: 1982).*
Coleman et al. (Research in Immunology, 1994; 145(1): 33-36) (Year: 1994).*
Ibragimova and Wade (Biophysical Journal, Oct. 1999, vol. 77, pp. 2191-2198) (Year: 1999).*
Almagro & Fransson, Frontiers in Bioscience 2008; 13:1619-33 (Year: 2008).*
Abaza et al. (Journal of Protein Chemistry, vol. 11, No. 5, 1992, pp. 433-444) (Year: 1992).*
Kojima T and Kitamura T. Nat Biotechnol. 17, 487-90(1999) (Year: 1999).*
EFEMP1 purified MaxPab mouse polyclonal antibody (B01P) ((http://www.abnova.com/products/products_detail.asp?catalog_id=H00002202-B01P) downloaded Jul. 30, 2019) (Year: 2019).*
Product datasheet fibulin-3/EFEMP1 antibody NB300-691.5 Mar. 2013.(online) 9Retrieved on May 19, 2005). Retrieved from the internet <URL:http://www.novusbio.com/fibulin-3-EFEMP10Antibody_NB300-691.html>p. 2, para 2.
Albig et al. "Fibulins 3 and 5 Antagonize Tumor Angiogenesis in vivo", Cancer Res., 66(5):2621-9 (2006).
Argraves et al., "Fibulins: physiological and disease perspectives", EMBO Rep., 4(12):1127-31 (2003).
(Continued)

*Primary Examiner* — Peter J Reddig
(74) *Attorney, Agent, or Firm* — Nixon Peabody LLP; David S. Resnick; Nicole D. Kling

(57) ABSTRACT

Embodiments described herein provide anti-fibulin-3 antibodies, recombinant proteins that bind specifically to fibulin-3, compositions and the treatment methods comprising these antibodies and recombinant proteins.

9 Claims, 39 Drawing Sheets
Specification includes a Sequence Listing.

(56) References Cited

OTHER PUBLICATIONS

Gallagher et al., "Fibulins and cancer: friend or foe?" Trends Mol. Med., 11(7):336-40 (2005).
Hu et al., "Fibulin-3 Is Uniquely Upregulated in Malignant Gliomas and Promotes Tumor Cell Motility and Invasion", Mol. Cancer Res., 7(11):1756-70 (2009).
Hu et al., "Fibulin-3 Promotes Glioma Growth and Resistance through a Novel Paracrine Regulation of Notch Signaling", Cancer Res., 72(15):3873-85 (2012).
Marmorstein et al., "Aberrant accumulation of EFEMP1 underlies drusen formation in Malattia Leventinese and age-related macular degeneration", Proc. Natl. Acad. Sci. U.S.A., 99(20):13067-72 (2002).
Marmorstein, "Association of EFEMP1 with malattia leventinese and age-related macular degeneration: a mini-review", Ophthalmic Genet., 25(3):219-26 (2004).
McLaughlin et al., "Lack of fibulin-3 causes early aging and herniation, but not macular degeneration in mice", Hum. Mol. Genet., 16(24):3059-70 (2007).
Obaya et al., "The dual role of fibulins in tumorigenesis", Cancer Lett., 325:132-8 (2012).
Pass et al., "Fibulin-3 as a Blood and Effusion Biomarker for Pleural Mesothelioma", N. Engl. J. Med., 367(15):1417-27 (2012).
Rahn et al., "Failure of Pelvic Organ Support in Mice Deficient in Fibulin-3", Am. J. Pathol., 174(1):206-15 (2009).
Seeliger et al. "EFEMP1 Expression Promotes in vivo Tumor Growth in Human Pancreatic Adenocarcinoma", Mol. Cancer Res., 7(2):189-98 (2009).
Song et al., "EFEMP1 expression promotes angiogenesis and accelerates the growth of cervical cancer in vivo", Gynecol. Oncol., 121:174-80 (2011).
Marmorstein "Association of EFEMP1 with malattia leventinese and age-related macular degeneration: a mini-review" Opthalmic Genet 25: 219-226 (2004).
Lotery et al., "Progress in defining the molecular biology of age related macular degeneration" Hum Genet 122: 219-236 (2007).
Marmorstein et al., "Formation and progression of sub-retinal pigment epithelium deposits in Efemp1 mutation knock-in mice: a model for the early pathogenic course of macular degeneration", Hum Mol Genet 16:2423-2432 (2007).

Wyatt et al., "Interaction of complement factor h and fibulin3 in age-related macular degeneration" PLoS One 8 (2013).
Perez-Rico et al., "Tropoelastin and fibulin overexpression in the subepithelial connective tissue of human pterygium", Am J Ophthalmol 151:44-52 (2011).
Engelsvold et al., "miRNA and mRNA expression profiling identifies members of the miR-200 family as potential regulators of epithelial-mesenchymal transition in pterygium", Exp Eye Res 115:189-198 (2013).
Hiddingh et al., "EFEMP1 induces γ-secretase/Notch-mediated temozolomide resistance in glioblastoma", Oncotarget 5:363-374 (2013).
Diersch et al., "Efemp1 and p27(Kip1) modulate responsiveness of pancreatic cancer cells towards a dual PI3K/mTOR inhibitor in preclinical models", Oncotarget 4:277-288 (2013).
Henrotin et al., "Fibulin 3 peptides Fib3-1 and Fib3-2 are potential biomarkers of osteoarthritis" Arthritis Rheum 64:2260-2267 (2012).
Hwang et al., "Fibulin-3 is associated with tumour progression and a poor prognosis in nasopharyngeal carcinomas and inhibits cell migration and invasion via suppressed AKT activity" 222:367-379 (2010).
Chen et al., "Overexpression of EFEMP1 correlates with tumor progression and poor prognosis in human ovarian carcinoma" PLoS One 8:e78783 (2013).
En-Lin et al., "The expression of EFEMP1 in cervical carcinoma and its relationship with prognosis", Gyencol Oncol 117:417-422 (2010).
Creaney et al., Comparison of fibulin-3 and mesothelin as markers in malignant mesothelioma, Thorax 69:895-902 (2014).
Giltay et al., "Sequence, recombinant expression and tissue localization of two novel extracellular matrix proteins, fibulin-3 and fibulin-4" Matrix Biol. 18(5): 469-480, 1999.
Marquez "Identification of hepatic microvascular adhesion-related genes of human colon cancer cells using random homozygous gene perturbation", Int. J. Cancer 133(9): 2113-2122 (2013).
Product datasheet GeneTex EFEMP1 antibody Retrieved on Jun. 10, 2019 URL https://www.genetex.com/PDF/Download?catno=GTX111657.
Product datasheet R&D Systems Human Fibulin 3 Antibody, Antigen Affinity-purified Polyclonal Sheet IgG, AF6235 Retrieved Jun. 10, 2019 URL https://www.rndsystems.com/products/human-fibulin-3-antibody_af6235.

* cited by examiner

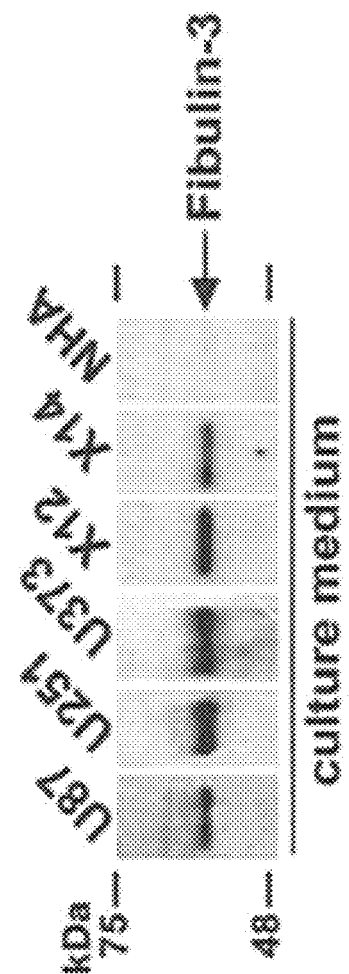
FIG. 1A
FIG. 1B

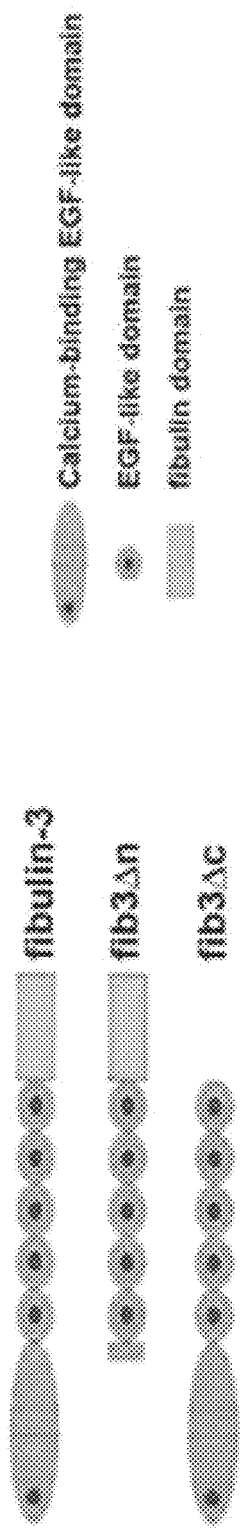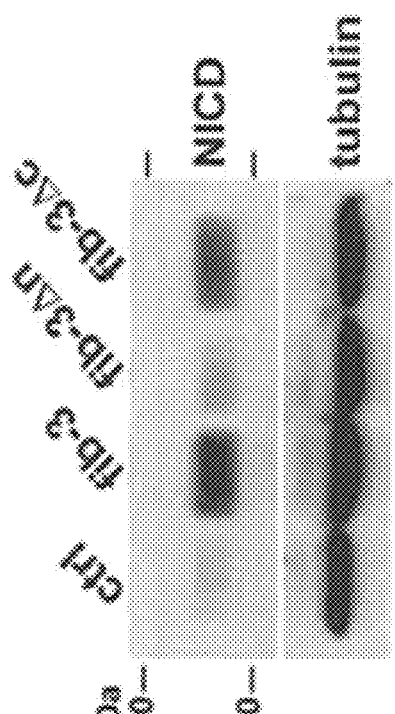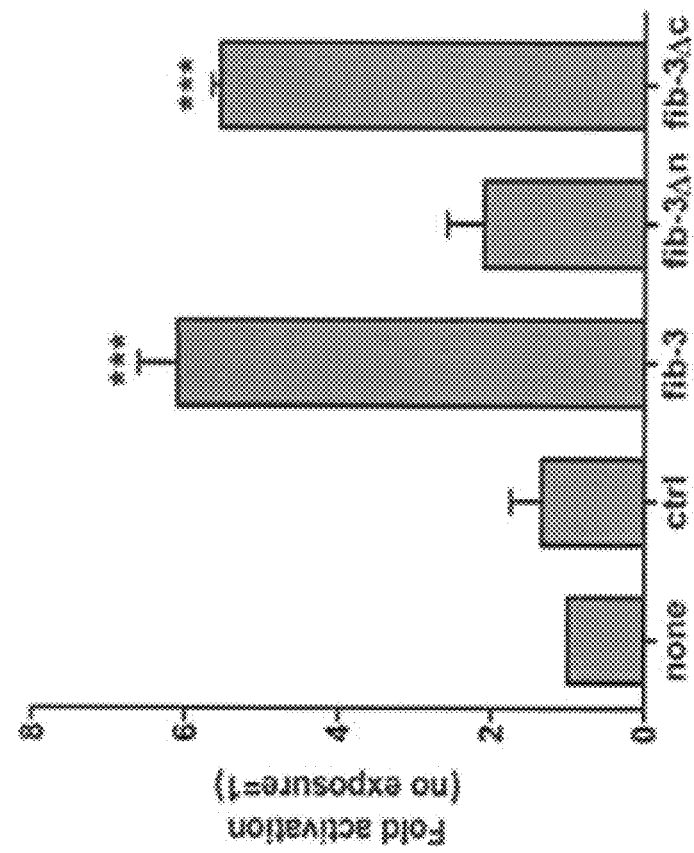
FIG. 2A
FIG. 2B
FIG. 2C fibulin-3  18QDTEETIIYTQCTDGYEWDPVRQQCKDIDECDIVPDACKGGMKCV (SEQ. ID. NO: 29)
fib3ΔDSL  18QDTEETI                             CDIVPDACKGGMKCV (SEQ. ID. NO: 30)

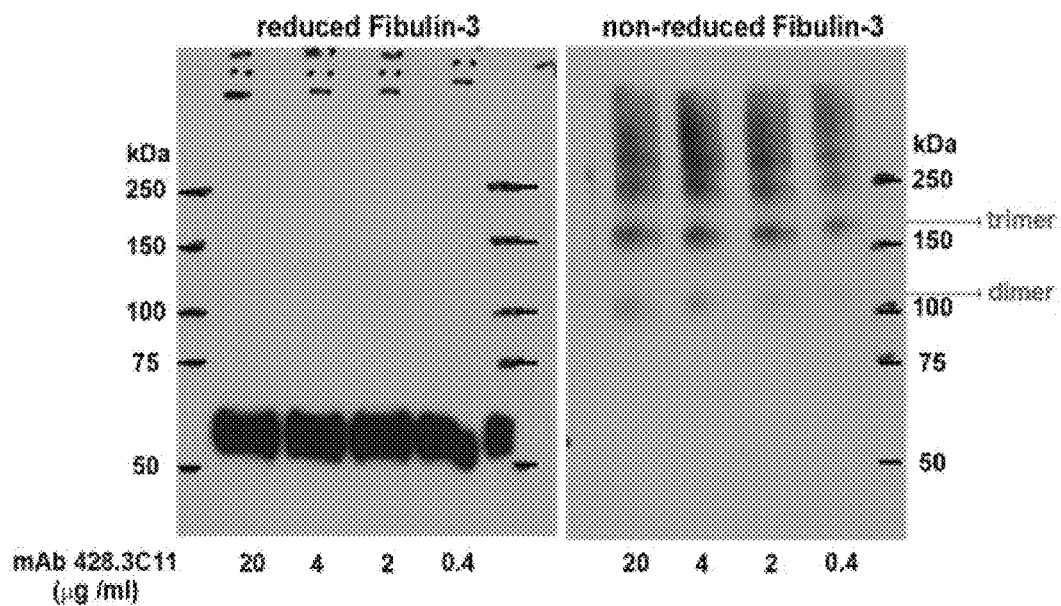
FIG. 11
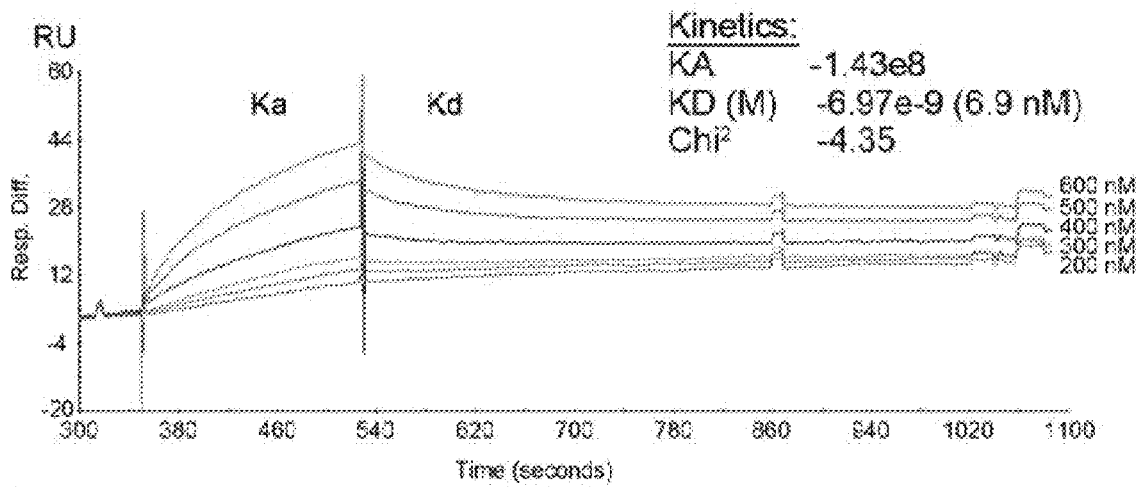
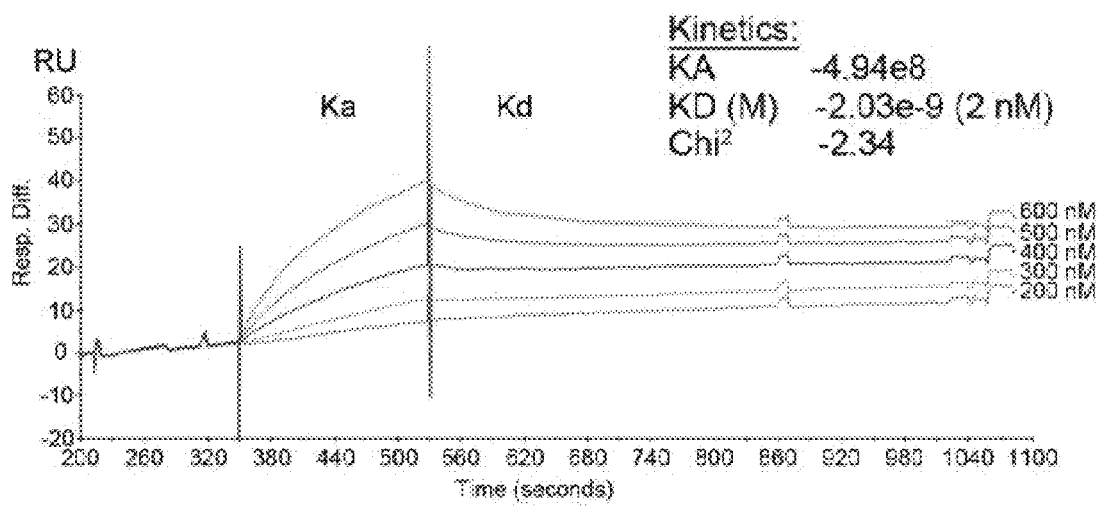
FIG. 12

VH CDR sequences:

cag atc cag ttg gta cag tct gga cct gag ttg aag aag cct gga gag aca gtc aag atc
 Q   I   Q   L   V   Q   S   G   P   E   L   K   K   P   G   E   T   V   K   I tcc tgc aag gct tct gga tat agt ttc aca acc tat gga atg agc tgg gtg aaa cag gct
 S   C   K   A   S   G   Y   S   F   T   T   Y   G   M   S   W   V   K   Q   A cca gga aag ggt tta aag tgg atg ggc tgg ata aac acc tac tct gga gtg cca aca tat
 P   G   K   G   L   K   W   M   G   W   I   N   T   Y   S   G   V   P   T   Y gct gat gac ttc aag gga cgg ttt gcc ttc ttt ttg gaa acc tct gcc agc act gcc tat
 A   D   D   F   K   G   R   F   A   F   L   E   T   S   A   S   T   A   Y ttg cag atc aat aac ctc aaa aat gag gac acg gct aca tat ttc tgt gca aga tgg gtt
 L   Q   I   N   N   L   K   N   E   D   T   A   T   Y   F   C   A   R   W   V gac tac tgg ggc caa ggc acc act ctc aca gtc tcc tca   (SEQ ID NO: 11)
 D   Y   W   G   Q   G   T   T   L   T   V   S   S    (SEQ ID NO: 3)

| CDR | Nucleotide sequence | Protein Sequence | # of AA residues |
|---|---|---|---|
| VH CDR-1 | ggatatagtttcacaacctatggaatgagc (SEQ ID NO: 13) | GYSFTTYGMS (SEQ ID NO: 5) | 10 |
| VH CDR-2 | tggataaacacctactctggagtgccaacatatgctgatgacttcaaggga (SEQ ID NO: 14) | WINTYSGVPTYADDFKG (SEQ ID NO: 6) | 17 |
| VH CDR-3 | tgggttgactac (SEQ ID NO: 15) | WVDY (SEQ ID NO: 7) | 4 |

VL CDR sequences:

gac atc aag atg acc cag tct cca tcc tcc atg tat gca tcg ctg gga gag aga gtc act
 D   I   K   M   T   Q   S   P   S   S   M   Y   A   S   L   G   E   R   V   T atc act tgc aag gcg agt cag gac att aaa agc tat tta agc tgg tac cag cag aaa cca
 I   T   C   K   A   S   Q   D   I   K   S   Y   L   S   W   Y   Q   Q   K   P tgg aaa tct cct aag acc ctg atc tat tat gca aca agc ttg gca gat ggg gtc cca tca
 W   K   S   P   K   T   L   I   Y   Y   A   T   S   L   A   D   G   V   P   S aga ttc agt ggc agc gga tct ggg caa gat tat tct cta acc atc agc agc ctg gag tct
 R   F   S   G   S   G   S   G   Q   D   Y   S   L   T   I   S   S   L   E   S gac gat aca gca act tat tac tgt cta cag cat ggt aag agc ccg tac acg ttc gga ggg
 D   D   T   A   T   Y   Y   C   L   Q   H   G   K   S   P   Y   T   F   G   G ggg acc aag ctg gaa ata aaa   (SEQ ID NO: 12)
 G   T   K   L   E   I   K    (SEQ ID NO: 4)

| CDR | Nucleotide sequence | Protein Sequence | # of AA residues |
|---|---|---|---|
| VL CDR-1 | tgcaaggcgagtcaggacattaaaagctatttaagc (SEQ ID NO: 16) | CKASQDIKSYLS (SEQ ID NO: 8) | 12 |
| VL CDR-2 | tatgcaacaagcttggcagat (SEQ ID NO: 17) | YATSLAD (SEQ ID NO: 9) | 7 |
| VL CDR-3 | ctacagcatggtaagagcccgtacacg (SEQ ID NO: 18) | LQHGKSPYT (SEQ ID NO: 10) | 9 |

*FIG. 13*

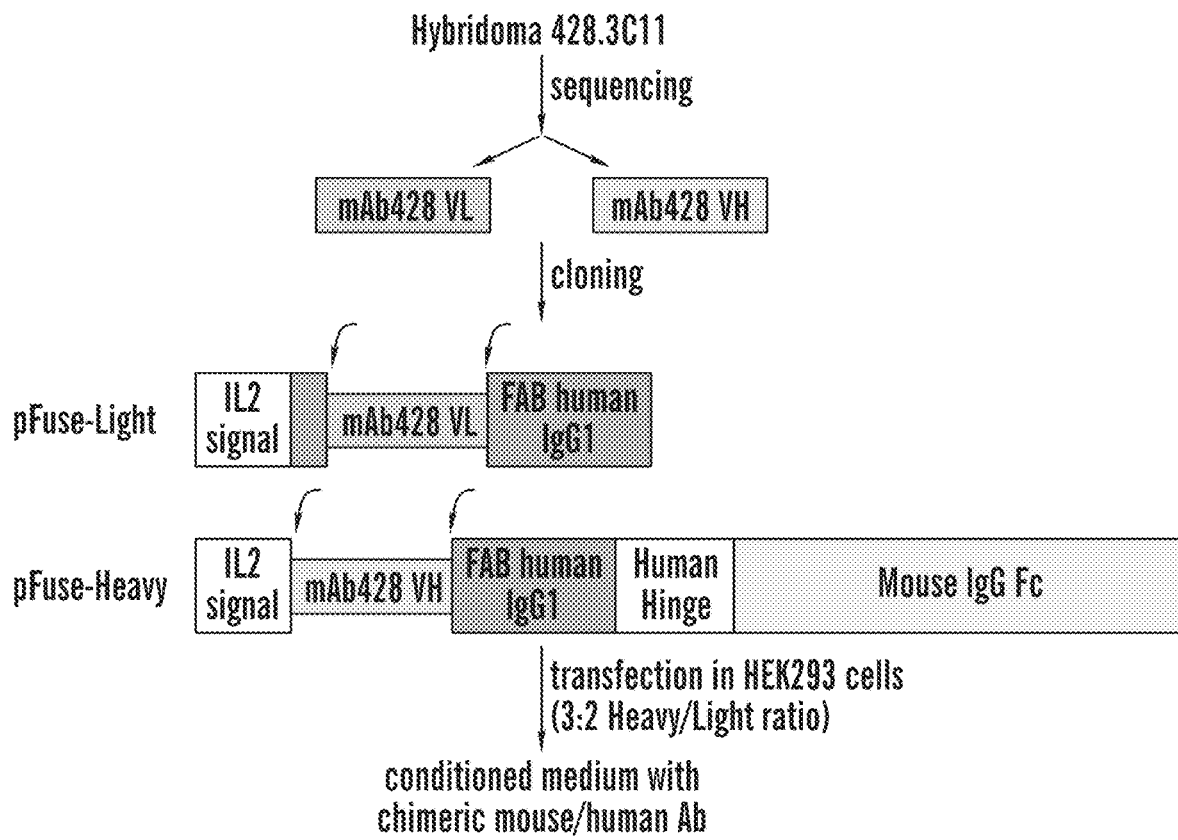
*FIG. 19A*
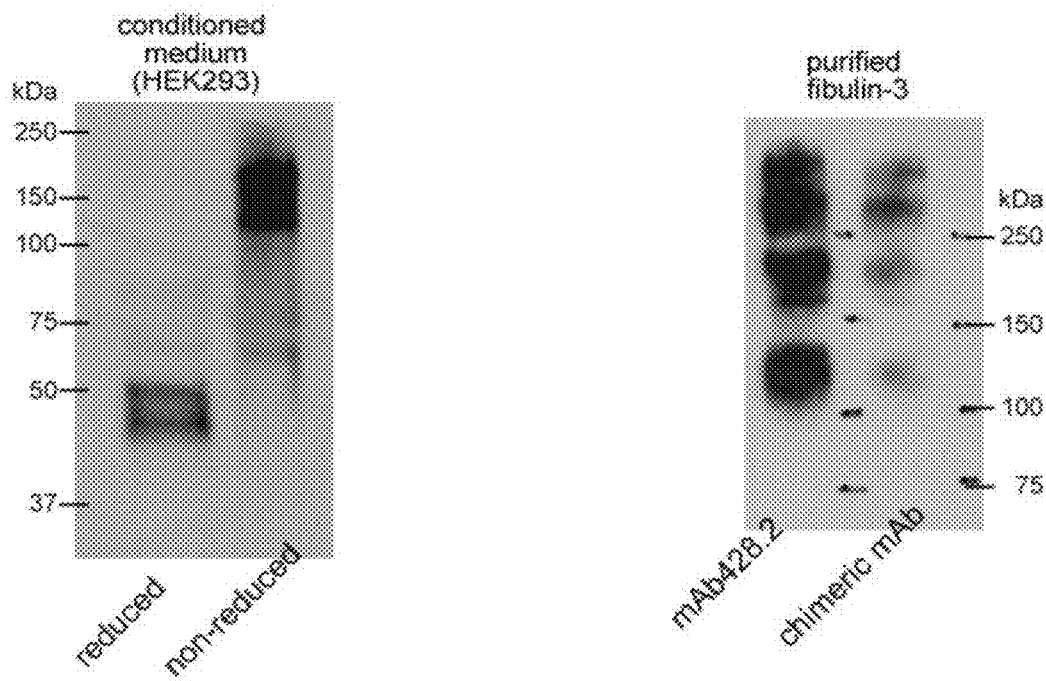
*FIG. 19B*          *FIG. 19C*

| Tissue | Detection of fibulin-3 in tissue | |
| --- | --- | --- |
| | mAb3-5 | mAb428.2 |
| Adrenal | negative | negative |
| Ovary | diffuse background | diffuse background |
| Pancreas | negative | some fibrils and diffuse background |
| Thyroid | negative | negative |
| Brain | negative, lipofuscin background | negative, high lipofuscin background |
| Lung | high elastin background, cannot detect specific staining | high elastin background, cannot detect specific staining |
| Cerebellum | negative | high background in white matter (which does not match expression of fibulin-3 protein or RNA; likely non-specific) |
| Spleen | negative | negative, punctate precipitation |
| Uterus | weak stromal staining, dense fibrils | stromal staining, very weak |
| Breast | weak stromal staining, scant fibrils | stromal staining, very weak |
| Cervix | weak stromal staining, dense density fibrils | stromal staining, very weak |
| Placenta | negative | negative |
| Heart | very weak fibril pattern to negative | very weak fibril pattern to negative |
| Kidney | very scant fibrils around major vessels | no fibrils detected, punctate precipitation |
| Skeletal Muscle | small punctate pattern to negative | negative or very small punctate pattern |
| Stomach | very weak fibrils to negative | negative, non-specific mAb aggregation |
| Small Intestine | negative | negative |
| Salivary Gland | few fibrils, mostly negative | negative |
| Liver | negative | negative |
| Skin | strong basement membrane staining | strong basement membrane staining |

*FIG. 20*

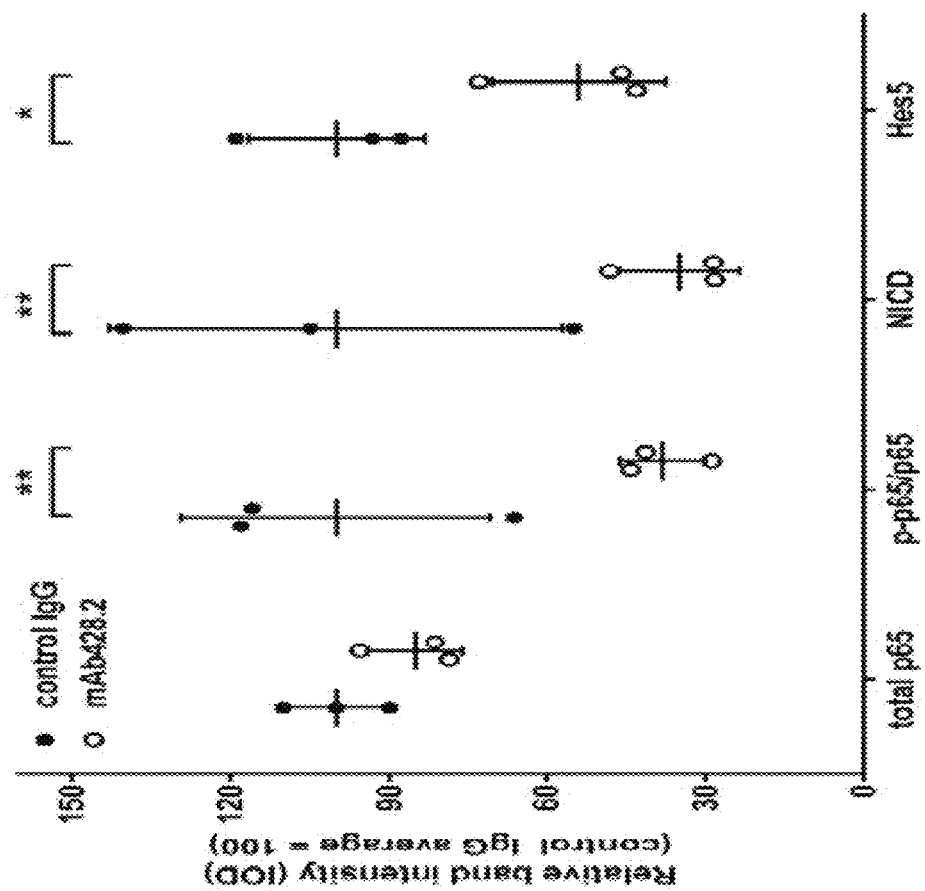
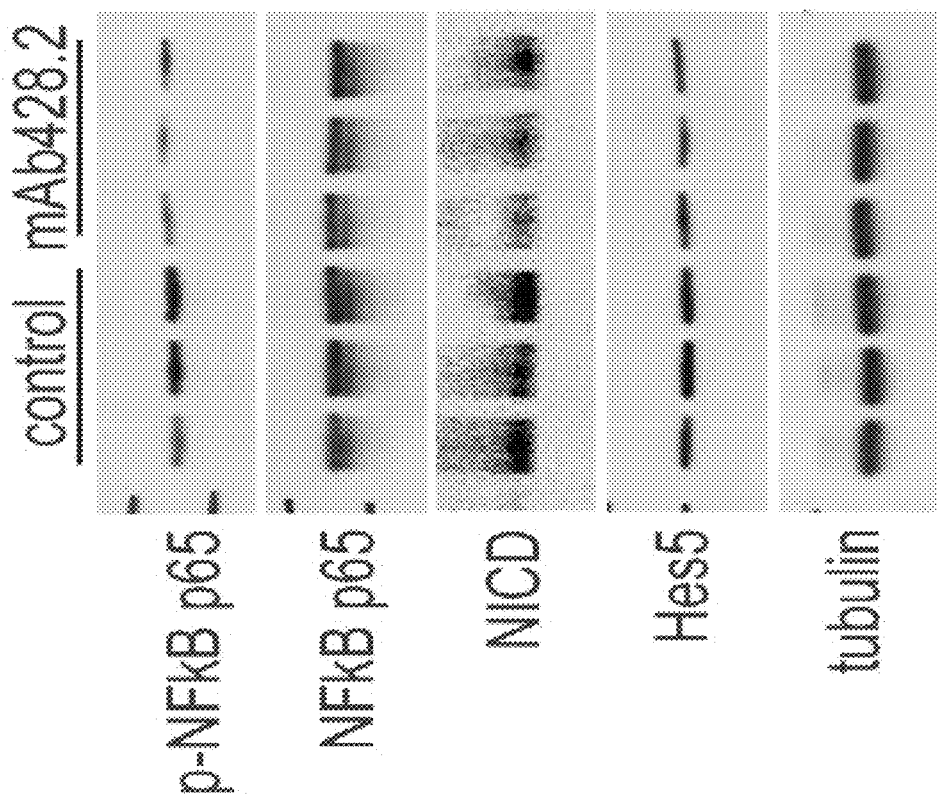
FIG. 23B
FIG. 23A

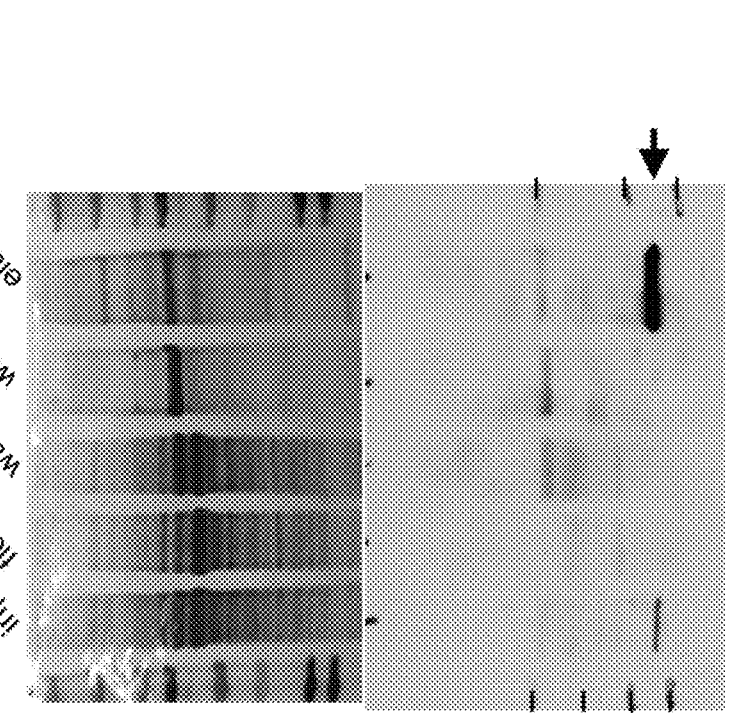
FIG. 26C
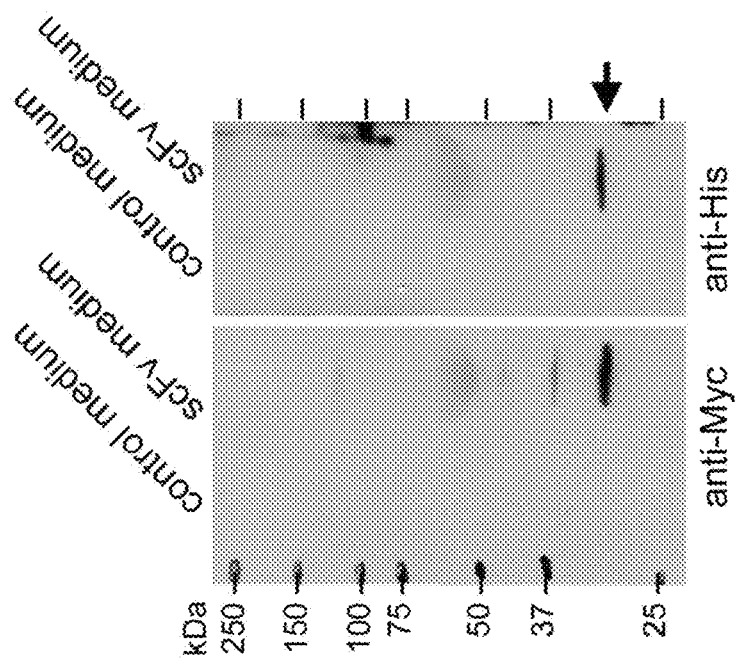
FIG. 26A
FIG. 26B

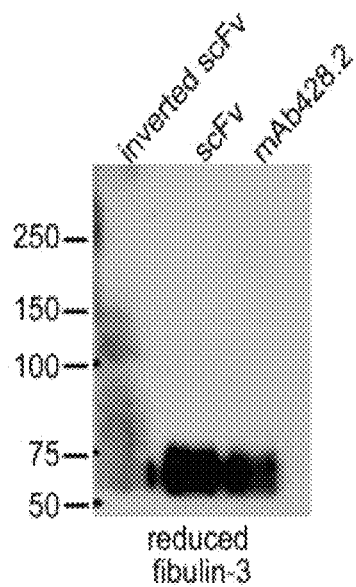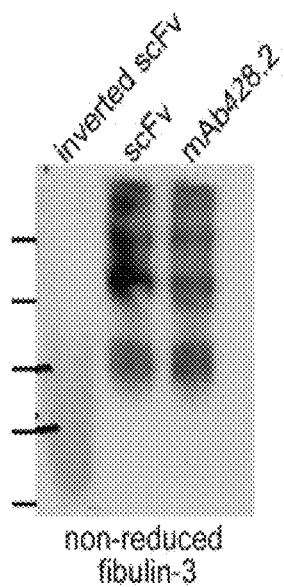
FIG. 27A  FIG. 27B
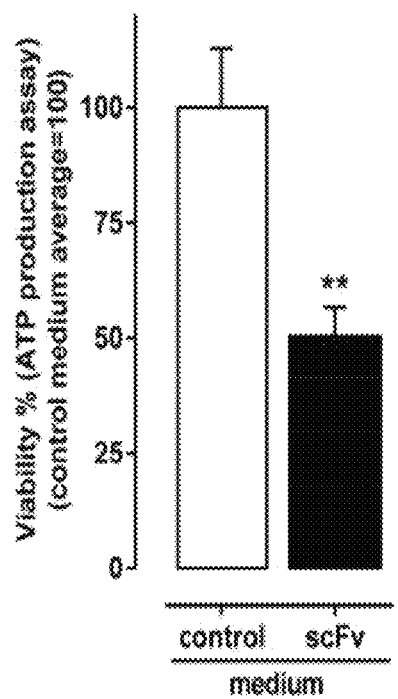
FIG. 27C
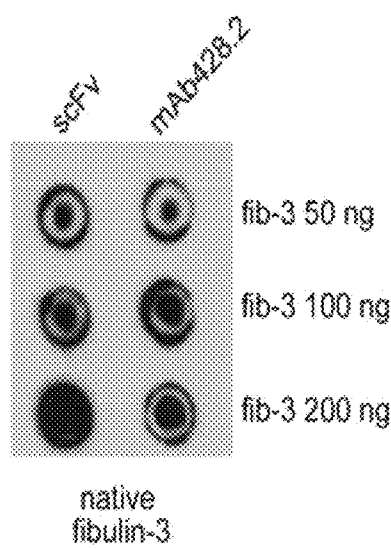

```
5' atgcaactcctgtcttgcattgcactaagtcttgcacttgtcacgaattc
                                                          50
3' tacgttgaggacagaacgtaacgtgattcagaacgtgaacagtgcttaag
                    IL2 signal peptide
    M  Q  L  L  S  C  I  A  L  S  L  A  L  V  T  N  S 5' agatatccagatgacccagtccccgagctcctgtccgcctctgtgggcg
                                                          100
3' tctataggtctactgggtcaggggctcgaggacaggcggagacacccgc
   |                Light chain human IgG1
    D  I  Q  M  T  Q  S  P  S  S  L  S  A  S  V  G 5' ataggtcaccatcacctgccgtgccagtcagtccgtgtccagcgctGAC
                                                          150
3' tatcccagtggtagtggacggcacggtcagtcaggcacaggtcgcgaCTG
              Light chain human IgG1              | VL
    D  R  V  T  I  T  C  R  A  S  Q  S  V  S  S  A  D 5' ATCAAGATGACCCAGTCTCCATCCTCCATGTATGCATCGCTGGGAGAGAG
                                                          200
3' TAGTTCTACTGGGTCAGAGGTAGGAGGTACATACGTAGCGACCCTCTCTC
                          VL
    I  K  M  T  Q  S  P  S  S  M  Y  A  S  L  G  E  R 5' AGTCACTATCACTTGCAAGGCGAGTCAGGACATTAAAAGCTATTTAAGCT
                                                          250
3' TCAGTGATAGTGAACGTTCCGCTCAGTCCTGTAATTTTCGATAAATTCGA
                          VL
    V  T  I  T  C  K  A  S  Q  D  I  K  S  Y  L  S 5' GGCACCAGCAGAAACCATGGAAATCTCCTAAGACCCTGATCTATTATGCA
                                                          300
3' CCGTGGTCGTCTTTGGTACCTTTAGAGGATTCTGGGACTAGATAATACGT
                          VL
    W  H  Q  Q  K  P  W  K  S  P  K  T  L  I  Y  Y  A 5' ACAAGCTTGGCAGATGGGGTCCCATCAAGATTCAGTGGCAGCGGATCTGG
                                                          350
3' TGTTCGAACCGTCTACCCCAGGGTAGTTCTAAGTCACCGTCGCCTAGACC
                          VL
    T  S  L  A  D  G  V  P  S  R  F  S  G  S  G  S  G
```

*FIG. 28*

```
5'  GCAAGATTATTCTCTAACCATCAGCAGCCTGGAGTCTGACGATACAGCAA
    ++++++++++++++++++++++++++++++++++++++++++++++++++  400
3'  CGTTCTAATAAGAGATTGGTAGTCGTCGGACCTCAGACTGCTATGTCGTT
                              VL
     Q  D  Y  S  L  T  I  S  S  L  E  S  D  D  T  A

5'  CTTATTACTGTCTACAGCATGGTAAGAGCCCGTACACGTTCGGAGGGGGG
    ++++++++++++++++++++++++++++++++++++++++++++++++++  450
3'  GAATAATGACAGATGTCGTACCATTCTCGGGCATGTGCAAGCCTCCCCCC
                              VL
     T  Y  Y  C  L  Q  H  G  K  S  P  Y  T  F  G  G

5'  ACCAAGCTGGAAATAAAAggtaccaaggtggagatcaaacgaactgtggc
    ++++++++++++++++++++++++++++++++++++++++++++++++++  500
3'  TGGTTCGACCTTTATTTTccatggttccacctctagtttgcttgacaccg
              VL          |     Light chain human IgG1
     T  K  L  E  I  K  G  T  K  V  E  I  K  R  T  V  A 5'  tgcaccatctgtcttcatcttccgccatctgattcacagttgaaatctg
    ++++++++++++++++++++++++++++++++++++++++++++++++++  550
3'  acgtggtagacagaagtagaaggcggtagactaagtgtcaactttagac
                        Light chain human IgG1
     A  P  S  V  F  I  F  P  P  S  D  S  Q  L  K  S 5'  gaactgcctctgttgtgtgcctgctgaataacttctatcccagagaggcc
    ++++++++++++++++++++++++++++++++++++++++++++++++++  600
3'  cttgacggagacaacacacggacgacttattgaagatagggtctctccgg
                        Light chain human IgG1
     G  T  A  S  V  V  C  L  L  N  N  F  Y  P  R  E  A 5'  aaagtacagtggaaggtggataacgcctccaatcgggtaactcccagga
    ++++++++++++++++++++++++++++++++++++++++++++++++++  650
3'  tttcatgtcaccttccacctattgcggaggttagcccattgagggtcct
                        Light chain human IgG1
     K  V  Q  W  K  V  D  N  A  L  Q  S  G  N  S  Q  E 5'  gagtgtcacagagcaggacagcaaggacagcacctacagcctcagcagca
    ++++++++++++++++++++++++++++++++++++++++++++++++++  700
3'  ctcacagtgtctcgtcctgtcgttcctgtcgtggatgtcggagtcgtcgt
                        Light chain human IgG1
     S  V  T  E  Q  D  S  K  D  S  T  Y  S  L  S  S
```

*FIG. 28 continued*

```
5' cctgacgctgagcaaagcagactacgaaaaacataaagtctacgcctgc
3' ggactgcgactcgtttcgtctgatgcttttgtattcagatgcggacg
                        Light chain human IgG1
    T  L  T  L  S  K  A  D  Y  E  K  H  K  V  Y  A  C
```
750

```
5' gaagtcacccatcagggcctgagctcgcccgtcacaaagagcttcaacag
3' cttcagtgggtagtcccggactcgagcgggcagtgtttctcgaagttgtc
                        Light chain human IgG1
    E  V  T  H  Q  G  L  S  S  P  V  T  K  S  F  N  R
```
800

```
5' gggagagtgttag
3' ccctctcacaatc
   Light c...an IgG1
    G  E  C  *
```
813

*FIG. 28 continued*

```
5'  xxatgtacaggatgcaactcctgtcttgcattgcactaagtcttgcactt
         [IL2 signal peptide]
    ├──┼──┼──┼──┼──┼──┼──┼──┼──┼──┼──┼──┼──┼──┼──┤ 50
3'   X  M  Y  R  M  Q  L  L  S  C  I  A  L  S  L  A  L 5'  gtcacgaattcggaggttcagctggtggagcagatccagttggtacagtc
    [IL2 sig..eptide][FAB hum..1gamma]      [Vh
    ├──┼──┼──┼──┼──┼──┼──┼──┼──┼──┼──┼──┼──┼──┼──┤ 100
3'    V  T  N  S  E  V  Q  L  V  E  Q  I  Q  L  V  Q  S 5'  tggacctgagttgaagaagcctggagagacagtcaagatctcctgcaagg
                          Vh
    ├──┼──┼──┼──┼──┼──┼──┼──┼──┼──┼──┼──┼──┼──┼──┤ 150
3'    Q  P  E  L  K  K  P  G  E  T  V  K  I  S  C  K 5'  cttctggatatagtttcacaacctatggaatgagctgggtgaaacaggct
                          Vh
    ├──┼──┼──┼──┼──┼──┼──┼──┼──┼──┼──┼──┼──┼──┼──┤ 200
3'    A  S  G  Y  S  F  T  T  Y  G  M  S  W  V  K  Q  A 5'  ccaggaaagggtttaaagtggatgggctggataaacacccactctggagt
                          Vh
    ├──┼──┼──┼──┼──┼──┼──┼──┼──┼──┼──┼──┼──┼──┼──┤ 250
3'    P  G  K  G  L  K  W  M  G  W  I  N  T  H  S  G  V 5'  gccaacatatgctgatgacttcaagggacggtttgccttcttttggaaa
                          Vh
    ├──┼──┼──┼──┼──┼──┼──┼──┼──┼──┼──┼──┼──┼──┼──┤ 300
3'    P  T  Y  A  D  D  F  K  G  R  F  A  F  F  L  E 5'  cctctgccagcactgcctatttgcagatcaataacctcaaaaatgaggac
                          Vh
    ├──┼──┼──┼──┼──┼──┼──┼──┼──┼──┼──┼──┼──┼──┼──┤ 350
3'    T  S  A  S  T  A  Y  L  Q  I  N  N  L  K  N  E  D 5'  acggctacatatttctgtgcaagatgggttgactactggggccaaggcac
                          Vh
    ├──┼──┼──┼──┼──┼──┼──┼──┼──┼──┼──┼──┼──┼──┼──┤ 400
3'    T  A  T  Y  F  C  A  R  W  V  D  Y  W  G  Q  G  T
```

FIG. 29

```
5'  cactctcacagtctcctcaggaaccctggtcaccgtctcctcggctcca
        |----- Vh -----|  |----- FAB human IgG1gamma -----
    +--+--+--+--+--+--+--+--+--+--+--+--+--+--+--+--+  450
3     T  L  T  V  S  S  G  T  L  V  T  V  S  S  A  S 5'  ccaagggtccatcggtcttccccctggcaccctcctccaagagcacctct
        ----- FAB human IgG1gamma -----
    +--+--+--+--+--+--+--+--+--+--+--+--+--+--+--+--+  500
3     T  K  G  P  S  V  F  P  L  A  P  S  K  S  T  S 5'  gggggcacagcggccctgggctgcctggtcaaggactacttccccgaacc
        ----- FAB human IgG1gamma -----
    +--+--+--+--+--+--+--+--+--+--+--+--+--+--+--+--+  550
3     G  G  T  A  A  L  G  C  L  V  K  D  Y  F  P  E  P 5'  ggtgacggtgtcgtggaactcaggcgccctgaccagcggcgtgcacacct
        ----- FAB human IgG1gamma -----
    +--+--+--+--+--+--+--+--+--+--+--+--+--+--+--+--+  600
3     V  T  V  S  W  N  S  G  A  L  T  S  G  V  H  T 5'  tcccggctgtcctacagtcctcaggactctactccctcagcagcgtggtg
        ----- FAB human IgG1gamma -----
    +--+--+--+--+--+--+--+--+--+--+--+--+--+--+--+--+  650
3     F  P  A  V  L  Q  S  S  G  L  Y  S  L  S  S  V  V 5'  accgtgccctccagcagcttgggcacccagacctacatctgcaacgtgaa
        ----- FAB human IgG1gamma -----
    +--+--+--+--+--+--+--+--+--+--+--+--+--+--+--+--+  700
3     T  V  P  S  S  S  L  G  T  Q  T  Y  I  C  N  V  N 5'  tcacaagcccagcaacaccaaggtcgacaagaaagttgagcccaaatctt
        ----- FAB human IgG1gamma -----| human hinge
    +--+--+--+--+--+--+--+--+--+--+--+--+--+--+--+--+  750
3     H  K  P  S  N  T  K  V  D  K  K  V  E  P  K  S 5'  gtgacaaaactcacacatgcccctccatgtccagcccctgaacttctggga
        ----- human hinge -----| mouse Fc
    +--+--+--+--+--+--+--+--+--+--+--+--+--+--+--+--+  800
3     C  D  K  T  H  T  C  P  P  C  P  A  P  E  L  L  G
```

*FIG. 29 continued*

```
5'  ggaccttctgtcttcatcttccccccaaagcccaaggatgtgctcacc at
                        mouse Fc
                                                        850
    G  P  S  V  F  I  P  P  P  K  P  K  D  V  L  T  I 5'  tactctgactcctaaggtcacgtgtgttgtggtagacatcagcaagga tg
                        mouse Fc
                                                        900
    T  L  T  P  K  V  T  C  V  V  V  D  I  S  K  D 5'  atcccgaggtccagttcagctggtttgtagatgatgtggaggtgcaca ca
                        mouse Fc
                                                        950
    D  P  E  V  Q  F  S  W  F  V  D  D  V  E  V  H  T 5'  gctcagacgcaacccggaggagcagttcaacagcactttccgctca gt
                        mouse Fc
                                                        1000
    A  Q  T  Q  P  R  E  E  Q  F  N  S  T  F  R  S  V 5'  cagtgaacttccatcatgcaccaggactggctcaatggcaaggagt tca
                        mouse Fc
                                                        1050
    S  E  L  P  I  M  H  Q  D  W  L  N  G  K  E  F 5'  aatgcagggtcaacagtgcagcttccctgcccccatcgagaaaac catc
                        mouse Fc
                                                        1100
    K  C  R  V  N  S  A  A  F  P  A  P  I  E  K  T  I 5'  tccaaaccaaaggcagaccgaaggctccacaggtgtacaccattcc acc
                        mouse Fc
                                                        1150
    S  K  T  K  G  R  P  K  A  P  Q  V  Y  T  I  P  P 5'  tcccaaggagcagatggccaaggataaagtcagtctgacctgcatga taa
                        mouse Fc
                                                        1200
    P  K  E  Q  M  A  K  D  K  V  S  L  T  C  M  I
```

*FIG. 29 continued*

```
5'      cagacttcttccctgaagacattactgtggagtggcagtggaatgggcag
                            mouse Fc
        ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  1250
3'       T  D  F  F  P  E  D  I  T  V  E  W  Q  W  N  G  Q 5'      ccagcggagaactacaagaacactcagcccatcatggacacagatggctc
                            mouse Fc
        ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  1300
3'       P  A  E  N  Y  K  N  T  Q  P  I  M  D  T  D  G  S 5'      ttacttcgtctacagcaagctcaatgtgcagaagagcaactgggaggcag
                            mouse Fc
        ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  1350
3'       Y  F  V  Y  S  K  L  N  V  Q  K  S  N  W  E  A 5'      gaaatactttacctgctctgtgttacatgagggcctgcacaaccaccat
                            mouse Fc
        ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  1400
3'       G  N  T  F  T  C  S  V  L  H  E  G  L  H  N  H  H 5'      actgagaagagcctctccactctctggtaaatga
                       mouse Fc
        ┼┼┼┼┼┼┼┼┼┼┼┼┼┼┼┼┼┼┼┼┼┼┼┼┼┼┼┼┼┼┼┼┼┼┼┼  1436
3'       T  E  K  S  L  S  H  S  P  G  K  .
```

*FIG. 29 continued*

```
5' atgaaatacctgctgccgaccgctgctgctggtctgctgctcctcgctgc
                                                         50
       pelB leader sequence
    M  K  Y  L  L  P  T  A  A  A  G  L  L  L  A  A 5' ccagccggcgatggccgatattaaaatgacgcagtctccgagcagtatgt
                                                         100
       pelB leader sequence  |        mAb428 VL
    Q  P  A  M  A  D  I  K  M  T  Q  S  P  S  S  M 5' acgcaagcctgggtgaacgtgtgacgattacctgtaaagcctctcaagat
                                                         150
                       mAb428 VL
    T  A  S  L  G  E  R  V  T  I  T  C  K  A  S  Q  D 5' atcaaatcctatctgtcatggcatcagcaaaaaccgtggaaaagcccgaa
                                                         200
                       mAb428 VL
    I  K  S  Y  L  S  W  H  Q  Q  K  P  W  K  S  P  K 5' aacctgatttattacgcaacgtcactggctgatggcgtgccgtcgcgtt
                                                         250
                       mAb428 VL
    T  L  I  Y  Y  A  T  S  L  A  D  G  V  P  S  R 5' tttcaggttcgggcagcggtcaggattatagcctgaccatcagctctctg
                                                         300
                       mAb428 VL
    F  S  G  S  G  S  G  Q  D  Y  S  L  T  I  S  S  L 5' gaatctgatgacaccgcgacgtattactgcctgcaacacggtaaaagccc
                                                         350
                       mAb428 VL
    E  S  D  D  T  A  T  Y  Y  C  L  Q  H  G  K  S  P 5' gtacaccttcggcggtggcacgaaactggaaattaaaggtggcggtggct
                                                         400
                       mAb428 VL              |  linker peptide
    Y  T  F  G  G  G  T  K  L  E  I  K  G  G  G
```

*FIG. 30*

```
5'  ctggtggcggtggcagtggtggcggtggctcccagatccaactggtccag
o   +----+----+----+----+----+----+----+----+----+----+  450
o         linker peptide              |      mAb428 VH
1    S  G  G  G  G  S  G  G  G  S  Q  I  Q  L  V  Q
o 5'  agtggccggaactgaaaaaaccgggtgaaaccgtgaaaatttctgtaa
o   +----+----+----+----+----+----+----+----+----+----+  500
o                            mAb428 VH
1    S  G  P  E  L  K  K  P  G  E  T  V  K  I  S  C  K
o 5'  agcgtcggctatagctttaccacgtacggtatgagttgggttaaacagg
o   +----+----+----+----+----+----+----+----+----+----+  550
o                            mAb428 VH
1    A  S  G  Y  S  F  T  T  Y  G  M  S  W  V  K  Q
o 5'  ccccgggcaaaggtctgaaatggatgggctggatcaacacctattctggt
o   +----+----+----+----+----+----+----+----+----+----+  600
o                            mAb428 VH
1    A  P  G  K  G  L  K  W  M  G  W  I  N  T  Y  S  G
o 5'  gtcccgacgtacgcagatgactttaaaggccgtttcgcgttttttctgga
o   +----+----+----+----+----+----+----+----+----+----+  650
o                            mAb428 VH
1    V  P  T  Y  A  D  D  F  K  G  R  F  A  F  F  E
o 5'  aacctctgcgagtacggcctatctgcagatcaacaacctgaaaaacgaag
o   +----+----+----+----+----+----+----+----+----+----+  700
o                            mAb428 VH
1    T  S  A  S  T  A  Y  L  Q  I  N  N  L  K  N  E
o 5'  ataccgcgacgtatttctgcgcacgttgggtggactactggggtcaaggt
o   +----+----+----+----+----+----+----+----+----+----+  750
o                            mAb428 VH
1    D  T  A  T  Y  F  C  A  R  W  V  D  Y  W  G  Q  G
o 5'  accacgctgaccgttagttccgaacaaaaactgattagtgaagaagacct
o   +----+----+----+----+----+----+----+----+----+----+  800
o             mAb428 VH                 |      Myc tag
1    T  T  L  T  V  S  S  E  Q  K  L  I  S  E  E  D  L
o 5'  gaatatgcacacggccaccaccaccaccaccattaa
o   +----+----+----+----+----+----+----+  837
o   ]              His tag
1    N  M  H  T  G  H  H  H  H  H  H  .
```

*FIG. 30 continued*

```
5' atggaaaccgatacactgctgctgtgggtcctgctgctgtgggtgcccgg
                                                        50
      signal peptide
   M  E  T  D  T  L  L  L  W  V  L  L  L  W  V  P  G 5' gtcaactggcgatgacatcaagatgacacagagtccctctagtatgtacg
                                                        100
      signal peptide  |           mAb428 VL
   S  Y  G  D  D  I  K  M  T  Q  S  P  S  S  M  Y 5' catcactgggcgagagggtgaccatcacatgtaaagcctctcaggatatt
                                                        150
                    mAb428 VL
   A  S  L  G  E  R  V  T  I  T  C  K  A  S  Q  D  I 5' aagagttatctgtcatggcaccagcagaagcctggaaaagccctaagac
                                                        200
                    mAb428 VL
   K  S  Y  L  S  W  H  Q  Q  K  P  W  K  S  P  K  T 5' actgatctactatgcaactagcctggcagacggagtcccatcccggttca
                                                        250
                    mAb428 VL
   L  I  Y  Y  A  T  S  L  A  D  G  V  P  S  R  F 5' gtgggtcaggaagcggccaggattactctctgaccatttcaagctggaa
                                                        300
                    mAb428 VL
   S  G  S  G  S  G  Q  D  Y  S  L  T  I  S  S  L  E 5' agtgacgatactgccacctactattgtctgcagcatggcaagagcctta
                                                        350
                    mAb428 VL
   S  D  D  T  A  T  Y  Y  C  L  Q  H  G  K  S  P  Y 5' tacctttggcggggaacaaaactggagatcaagggcggaggaggcagcg
                                                        400
                 mAb428 VL                |  linker peptide
   T  F  G  G  G  T  K  L  E  I  K  G  G  G  G  S
```

*FIG. 31*

```
5'  gaggaggagggtccggaggaggaggatctcagattcagctggtccagagc
                                                              450
         |linker peptide         |        mAb 428 VH
1    G  G  G  G  S  G  G  G  S  Q  I  Q  L  V  Q  S 5'  ggcccagagctgaagaaaccggggaaaccgtgaaaatcagctgcaaggc
                                                              500
                       mAb 428 VH
1    G  P  E  L  K  K  P  G  E  T  V  K  I  S  C  K  A 5'  ttccgggtactcttTcaccacatatggaatgtcctgggtcaagcaggca
                                                              550
                       mAb 428 VH
1    S  G  Y  S  F  T  T  Y  G  M  S  W  V  K  Q  A 5'  ctggcaaggggctgaaatggatgggctggattaacacttactccggggtg
                                                              600
                       mAb 428 VH
1    L  A  R  G  L  K  W  M  G  W  I  N  T  Y  S  G  V 5'  ccaacctatgccgacgatttcaaaggccggtttgctttctttctggagac
                                                              650
                       mAb 428 VH
1    P  T  Y  A  D  D  F  K  G  R  F  A  F  F  L  E  T 5'  atccgcctctactgcttacctgcagatcaacaatctgaagaatgaagaca
                                                              700
                       mAb 428 VH
1    S  A  S  T  A  Y  L  Q  I  N  N  L  K  N  E  D 5'  cagctacttactttgcgcaagatgggtggattattggggacagggaact
                                                              750
                       mAb 428 VH
1    T  A  T  Y  F  C  A  R  W  V  D  Y  W  G  Q  G  T 5'  accctgaccgtcagctccgaacagaaactgatttccgaggaggacctgaa
                                                              800
         |mAb 428 VH        |          Myc tag
1    T  L  T  V  S  S  E  Q  K  L  I  S  E  E  D  L  N 5'  catgcacactgggcaccaccaccaccactaa
                                                              834
                   His tag
1    M  H  T  G  H  H  H  H  H  H  .
```

*FIG. 31 continued* hEF1-HTLV Promoter tctgcgccgt tacagatcca agctgtgacc ggcgcctacc tgagatcacc ggcgaaggag
agacgcggca atgtctaggt tgacactgg ccgcggatgg actctagtgg ccgcttcctc

IL2sa
M Y R M Q L L S C I A L S L A L V T
ggccaccatg tacaggatgc aactcctgtc ttgcattgca ctaagtcttg cacttgtcac
ccggtggtac atgtcctacg ttgaggacag aacgtaacgt gattcagaac gtgaacagtg SacBI    AfeI    (SEQ ID NO: 38)                    SphI
                → (SEQ ID NO: 44)                   K V R S
gattggag gttcagc/gct ----SACB gene (2kb)---- gcatg/cctgg tcaccgtctc
ctaagcctc caagtcg/cga ---------------------- c/gtacggacc agtggcagag

FAB from human Ig gamma 1
S A S T K G P S V F P L A P S S K S T S
ctggcctcc accaagggtc catcggtctt cccctggca ccctcctca agagcacctc
gagccggagg tggttcccag gtagccagaa ggggaccgt gggaggaggt tctcgtggag G G T A A L G C L V K D Y F P E P V T V
tggggcaca gcggccctgg gctgcctggt caaggactac ttccccgaac cggtgacggt
accccgtgt cgccgggacc cgacggacca gttcctgatg aagggcttg gccactgcca S W N S G A L T S G V H T F P A V L Q S
gtcgtggaac tcaggcgccc tgaccagcgg cgtgcacacc ttcccggctg tcctacagtc
cagcaccttg agtccgcggg actggtcgcc gcacgtgtgg aagggccgac aggatgacag S G L Y S L S S V V T V P S S S L G T Q
ctcaggactc tactccctca gcagcgtggt gaccgtgccc tccagcagct gggcacca
gagtcctgag atgagggagt cgtcgcacca ctggcacggg aggtcgtcga cccgtggt T Y I C N V N H K P S N T K V D K K V E
gacctacatc tgcaacgtga atcacaagcc cagcaacacc aaggtcgaca agaaagttga
ctggatgtag acgttgcact tagtgttcgg gtcgttgtgg ttccagctgt ctttcaact

Human Hinge
P K S C D K T H T C P P C P A P E L L G
gcccaaatct tgtgacaaaa ctcacacatg cccaccgtgt ccagcccctg aactcctggg
cgggtttaga acactgtttt gagtgtgtac gggtggcaca ggtcggggac ttgaggaccc

Mouse FC
G P S V F I F P P K P K D V L T I T L T
aggacctcct gtcttcatct tccccccaaa gccaaggat gtgctcacca ttactctgac
tcctggaaga cagaagtaga aggggggtt cggttccta cacgagtggt aatgagactg P K V T C V V V D I S K D D P E V Q F S
tcctaaggtc acgtgtgttg tggtagacat cagcaaggat gatccgaggt ccagttcag
aggattccag tgcacacaac accatctgta gtcgttccta ctagggctcc agtcaagtc

*FIG. 32*

```
     W  F  V  D  D  V  E  V  H  T  A  Q  T  Q  P  R  E  E  Q  F
ctggtttgta gatgatgtgg aggtgcacac agctcagacg caacccggg aggagcagtt
gaccaaacat ctactacacc tccacgtgtg tcgagtctgc gttgggccc tcctcgtcaa N  S  T  F  R  S  V  S  E  L  P  I  M  H  Q  D  W  L  N  G
caacagcact tccgctcag tcagtgaact tccatcatg caccaggact ggctcaatgg
gttgtcgtga aaggcgagtc agtcacttga agggtagtac gtggtcctga ccgagttacc K  E  F  K  C  R  V  N  S  A  A  F  P  A  P  I  E  K  T  I
caaggagttc aaatgcaggg tcaacagtgc agctttccct gccccatcg agaaaaccat
gttcctcaag tttacgtccc agttgtcacg tcgaaaggga cggggtagc tctttggta S  K  T  K  G  R  P  K  A  P  Q  V  Y  T  I  P  P  P  K  E
ctccaaaacc aaaggcagac cgaaggctcc acaggtgtac accattccac ctcccaagga
gaggttttgg tttccgtctg gcttccgagg tgtccacatg tggtaaggtg gagggttcct Q  M  A  K  D  K  V  S  L  T  C  M  I  T  D  F  F  P  E  D
gcagatggcc aaggataaag tcagtctgac ctgcatgata acagacttct tcctgaaga
cgtctaccgg ttcctatttc agtcagactg gacgtactat tgtctgaaga agggacttct I  T  V  E  W  Q  W  N  G  Q  P  A  E  N  Y  K  N  T  Q  P
cattactgtg gagtggcagt ggaatgggca gccagcggag aactacaaga acactcagcc
gtaatgacac ctcaccgtca ccttacccgt cggtcgcctc ttgatgttct tgtgagtcgg I  M  D  T  D  G  S  Y  F  V  Y  S  K  L  N  V  Q  K  S  N
catcatggac acagatggct cttacttcgt ctacagcaag ctcaatgtgc agaagagcaa
gtagtacctg tgtctaccga gaatgaagca gatgtcgttc gagttacacg tcttctcgtt W  E  A  G  N  T  F  T  C  S  V  L  H  E  G  L  H  N  H  H
ctgggaggca ggaaatactt tcacctgctc tgtgttacat gagggcctgc acaaccacca
gaccctccgt cctttatgaa agtggacgag acacaatgta ctcccggacg tgttggtggt (SEQ ID NO: 39)
     T  E  K  S  L  S  H  S  P  G  K
tactgagaag agcctctccc actctcctgg taaatgatcc cagtgtccct agctggcag
atgactcttc tcggagaggg tgagaggacc atttactagg gtcacaggga tcgaccggtc SV40 polyA
acatgataag atacattgat gagtttggac aaaccacaac tagaatgcag tgaaaaaaat
tgtactattc tatgtaacta ctcaaacctg ttggtgttg atcttacgtc acttttttta (SEQ ID NO: 45)
```

*FIG. 32 continued* hEF1-HTLV Promoter

```
acgtctttgt ttcgttttct gttacagatc caagctgtga ccggcgccta cctgagatca
tgcagaaaca aagcaaaaga caatgtctag gttcgacact ggccgcggat ggactctagt
```

IL2ss                                                                EcoRI

M Y R M Q L L S C I A L S L A L V T N

```
acatgtacag gatgcaactc ctgtcttgca ttgcactaag tcttgcactt gtcacgaatt
tgtacatgtc ctacgttgag gacagaacgt aacgtgattc agaacgtgaa cagtgcttaa
```

S D I Q M T Q S P S S L S A S V G D R V

```
cagatatcca gatgacccag tcccctagct ccctgtccgc ctctgtgggc gatagggtca
gtctataggt ctactgggtc agggggatcga gggacaggcg gagacacccg ctatcccagt
```

AfeI

T I T C R A S Q S V S S A V A N I Q Q K

```
ccatcacctg ccgtgccagt cagtccgtgt ccagc/gctgt agcctggtat caacagaaac
ggtagtggac ggcacggtca gtcaggcaca ggtcg/cgaca tcggaccata gttgtcttg
```

(SEQ ID NO: 55)

HindIII    (SEQ ID NO: 53)                    KpnI

P G K A P K L                                     G T K V E I K

---- SACB gene (2kb) ---- g

```
gtccttttcg aggcttcgaa---------------------c/catggttcc acctctagtt
```

R T V A A P S V F I F P P S D S Q L K S

```
acgaactgtg gctgcaccat ctgtcttcat cttcccgcca tctgattcac agttgaaatc
tgcttgacac cgacgtggta gacagaagta gaaggggcgg agactaagtg tcaactttag
```

G T A S V V C L L N N F Y P R E A K V Q

```
tggaactgcc tctgttgtgt gcctgctgaa taacttctat cccagagagg ccaaagtaca
accttgacgg agacaacaca cggacgactt attgaagata gggtctctcc ggtttcatgt
```

N K V D N A L Q S G N S Q E S V T E Q D

```
gtggaaggtg gataacgcc tccaatcggg taactcccag gagagtgtca cagagcagga
cacctttccac ctattgcgg aggttagccc attgagggtc ctctcacagt gtctcgtcct
```

S K D S T Y S L S S T L T L S K A D Y E

```
cagcaaggac agcacctaca gcctcagcag caccctgacg ctgagcaaag cagactacga
gtcgttcctg tcgtggatgt cggagtcgtc gtggactgc gactcgtttc gtctgatgct
```

K H K V Y A C E V T H Q G L S S P V T K

```
aaaacataaa gtctacgcct gcgaagtcac ccatcagggc ctgagctcgc ccgtcacaaa
tttgtattt cagatgcgga cgcttcagtg ggtagtcccg gactcgagcg ggcagtgttt
```

S F N R G E C                 (SEQ ID NO: 48)       NheI    sv40 polyA

```
ga                           tgagaca aagtcctga gagctagctg gcagacatg
ctcgaagttg tccctctca aatctctgt ttccaggact ctcgatcgac cggtctgtac
```

(SEQ ID NO: 54)

*FIG. 33*

SEQUENCE LISTING

<160> NUMBER OF SEQ ID NOS: 56

<210> SEQ ID NO 1
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Thr Tyr Thr Gln Cys Thr Asp Gly Tyr Glu Trp Asp Pro Val Arg Gln
1               5                   10                  15

Gln Cys Lys Asp Ile Asp Glu
            20

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Thr Tyr Thr Gln Cys Thr Asp Gly Tyr Glu Trp Asp Pro Val Arg Gln
1               5                   10                  15

Gln Cys Arg Asp Ile Asp Glu
            20

<210> SEQ ID NO 3
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Ser Phe Thr Thr Tyr
            20                  25                  30

Gly Met Ser Trp Val Lys Gln Ala Pro Gly Lys Gly Leu Lys Trp Met
        35                  40                  45

Gly Trp Ile Asn Thr Tyr Ser Gly Val Pro Thr Tyr Ala Asp Asp Phe
            50                  55                  60

Lys Gly Arg Phe Ala Phe Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                85                  90                  95

Ala Arg Trp Val Asp Tyr Trp Gly Gln Gly Thr Thr Leu Thr Val Ser
            100                 105                 110

Ser

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Lys Met Thr Gln Ser Pro Ser Ser Met Tyr Ala Ser Leu Gly
 1               5                  10                  15

Glu Arg Val Thr Ile Thr Cys Lys Ala Ser Gln Asp Ile Lys Ser Tyr
                20                  25                  30

Leu Ser Trp His Gln Lys Pro Trp Lys Ser Pro Lys Thr Leu Ile
            35                  40                  45

Tyr Tyr Ala Thr Ser Leu Ala Asp Gly Val Pro Ser Arg Phe Ser Gly
        50                  55                  60

Ser Gly Ser Gly Gln Asp Tyr Ser Leu Thr Ile Ser Ser Leu Glu Ser
 65                 70                  75                  80

Asp Asp Thr Ala Thr Tyr Tyr Cys Leu Gln His Gly Lys Ser Pro Tyr
                85                  90                  95

Thr Phe Gly Gly Gly Thr Lys Leu Glu Ile Lys
            100                 105

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Tyr Ser Phe Thr Thr Tyr Gly Met Ser
 1               5                  10

<210> SEQ ID NO 6
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Trp Ile Asn Thr Tyr Ser Gly Val Pro Thr Tyr Ala Asp Asp Phe Lys
 1               5                  10                  15

Gly

<210> SEQ ID NO 7

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Trp Val Asp Tyr
1

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Lys Ala Ser Gln Asp Ile Lys Ser Tyr Leu Ser
1               5                  10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Tyr Ala Thr Ser Leu Ala Asp
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Leu Gln His Gly Lys Ser Pro Tyr Thr
1               5

<210> SEQ ID NO 11
<211> LENGTH: 339
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(339)

<400> SEQUENCE: 11 cag atc cag ttg gta cag tct gga cct gag ttg aag aag cct gga gag      48
Gln Ile Gln Leu Val Gln Ser Gly Pro Glu Leu Lys Lys Pro Gly Glu
1               5                  10                  15 aca gtc aag atc tcc tgc aag gct tct gga tat agt ttc aca acc tat      96
Thr Val Lys Ile Ser Cys Lys Ala Ser Gly Tyr Ser Phe Thr Thr Tyr
            20                  25                  30 gga atg agc tgg gtg aaa cag gct cca gga aag ggt tta aag tgg atg     144
Gly Met Ser Trp Val Lys Gln Ala Pro Gly Lys Gly Leu Lys Trp Met
        35                  40                  45
```

```
ggc tgg ata aac acc tac tct gga gtg cca aca tat gct gat gac ttc      192
Gly Trp Ile Asn Thr Tyr Ser Gly Val Pro Thr Tyr Ala Asp Asp Phe
    50                  55                  60 aag gga cgg ttt gcc ttc ttt ttg gaa acc tct gcc agc act gcc tat      240
Lys Gly Arg Phe Ala Phe Phe Leu Glu Thr Ser Ala Ser Thr Ala Tyr
65                  70                  75                  80 ttg cag atc aat aac ctc aaa aat gag gac acg gct aca tat ttc tgt      288
Leu Gln Ile Asn Asn Leu Lys Asn Glu Asp Thr Ala Thr Tyr Phe Cys
                85                  90                  95 gca aga tgg gtt gac tac tgg ggc caa ggc acc act ctc aca gtc tcc      336
Ala Arg Trp Val Asp Tyr Trp Gly Gln Gly Thr Thr Leu Thr Val Ser
            100                 105                 110 tca                                                                   339
Ser

<210> SEQ ID NO 12
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(321)

<400> SEQUENCE: 12 gac atc aag atg acc cag tct cca tcc tcc atg tat gca tcg ctg gga       48
Asp Ile Lys Met Thr Gln Ser Pro Ser Ser Met Tyr Ala Ser Leu Gly
1               5                   10                  15 gag aga gtc act atc act tgc aag gcg agt cag gac att aaa agc tat       96
Glu Arg Val Thr Ile Thr Cys Lys Ala Ser Gln Asp Ile Lys Ser Tyr
                20                  25                  30 tta agc tgg cac cag cag aaa cca tgg aaa tct cct aag acc ctg atc      144
Leu Ser Trp His Gln Gln Lys Pro Trp Lys Ser Pro Lys Thr Leu Ile
            35                  40                  45 tat tat gca aca agc ttg gca gat ggg gtc cca tca aga ttc agt ggc      192
Tyr Tyr Ala Thr Ser Leu Ala Asp Gly Val Pro Ser Arg Phe Ser Gly
        50                  55                  60 agc gga tct ggg caa gat tat tct cta acc atc agc agc ctg gag tct      240
Ser Gly Ser Gly Gln Asp Tyr Ser Leu Thr Ile Ser Ser Leu Glu Ser
65                  70                  75                  80 gac gat aca gca act tat tac tgt cta cag cat ggt aag agc ccg tac      288
Asp Asp Thr Ala Thr Tyr Tyr Cys Leu Gln His Gly Lys Ser Pro Tyr
                85                  90                  95 acg ttc gga ggg ggg acc aag ctg gaa ata aaa                          321
Thr Phe Gly Gly Gly Thr Lys Leu Glu Ile Lys
            100                 105

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ggatatagtt tcacaaccta tggaatgagc                                      30

<210> SEQ ID NO 14
<211> LENGTH: 51
<212> TYPE: DNA
```

<213> ORGANISM: Artificial Sequence
<220> FEATURE:
<223> OTHER INFORMATION: Description of Artificial Sequence: Synthetic
      oligonucleotide

<400> SEQUENCE: 14
tggataaaca cctactctgg agtgccaaca tatgctgatg acttcaaggg a            51

<210> SEQ ID NO 15
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tgggttgact ac                                                       12

<210> SEQ ID NO 16
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
tgcaaggcga gtcaggacat taaaagctat ttaagc                             36

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
tatgcaacaa gcttggcaga t                                             21

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
ctacagcatg gtaagagccc gtacacg                                       27

<210> SEQ ID NO 19
<211> LENGTH: 813
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19
atgcaactcc tgtcttgcat tgcactaagt cttgcacttg tcacgaattc agatatccag    60
atgacccagt ccccgagctc cctgtccgcc tctgtgggcg atagggtcac catcacctgc   120
cgtgccagtc agtccgtgtc cagcgctgac atcaagatga cccagtctcc atcctccatg   180
tatgcatcgc tgggagagag agtcactatc acttgcaagg cgagtcagga cattaaaagc   240

```
tatttaagct ggcaccagca gaaaccatgg aaatctccta agaccctgat ctattatgca    300
acaagcttgg cagatggggt cccatcaaga ttcagtggca gcggatctgg gcaagattat    360
tctctaacca tcagcagcct ggagtctgac gatacagcaa cttattactg tctacagcat    420
ggtaagagcc cgtacacgtt cggagggggg accaagctgg aaataaaagg taccaaggtg    480
gagatcaaac gaactgtggc tgcaccatct gtcttcatct tcccgccatc tgattcacag    540
ttgaaatctg gaactgcctc tgttgtgtgc ctgctgaata acttctatcc cagagaggcc    600
aaagtacagt ggaaggtgga taacgccctc caatcgggta actcccagga gagtgtcaca    660
gagcaggaca gcaaggacag cacctacagc ctcagcagca ccctgacgct gagcaaagca    720
gactacgaaa acataaagt ctacgcctgc gaagtcaccc atcagggcct gagctcgccc    780
gtcacaaaga gcttcaacag gggagagtgt tag                                 813

<210> SEQ ID NO 20
<211> LENGTH: 1434
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20
atgtacagga tgcaactcct gtcttgcatt gcactaagtc ttgcacttgt cacgaattcg     60
gaggttcagc tggtggagca gatccagttg gtacagtctg gacctgagtt gaagaagcct    120
ggagagacag tcaagatctc ctgcaaggct tctggatata gtttcacaac ctatggaatg    180
agctgggtga acaggctcc aggaaagggt ttaaagtgga tgggctggat aaacacccac    240
tctggagtgc caacatatgc tgatgacttc aagggacggt ttgccttctt tttggaaacc    300
tctgccagca ctgcctattt gcagatcaat aacctcaaaa atgaggacac ggctacatat    360
ttctgtgcaa gatgggttga ctactggggc caaggcacca ctctcacagt ctcctcagga    420
accctggtca ccgtctcctc ggcctccacc aagggtccat cggtcttccc cctggcaccc    480
tcctccaaga gcacctctgg gggcacagcg gccctgggct gcctggtcaa ggactacttc    540
cccgaaccgg tgacggtgtc gtggaactca ggcgccctga ccagcggcgt gcacaccttc    600
ccggctgtcc tacagtcctc aggactctac tccctcagca gcgtggtgac cgtgccctcc    660
agcagcttgg gcacccagac ctacatctgc aacgtgaatc acaagcccag caacaccaag    720
gtcgacaaga aagttgagcc caaatcttgt gacaaaactc acacatgccc tccatgtcca    780
gcccctgaac ttctgggagg accttctgtc ttcatcttcc ccccaaagcc caaggatgtg    840
ctcaccatta tctctgactcc taaggtcacg tgtgttgtgg tagacatcag caaggatgat    900
cccgaggtcc agttcagctg gtttgtagat gatgtggagg tgcacacagc tcagacgcaa    960
ccccgggagg agcagttcaa cagcactttc cgctcagtca gtgaacttcc catcatgcac   1020
caggactggc tcaatggcaa ggagttcaaa tgcagggtca acagtgcagc tttccctgcc   1080
cccatcgaga aaaccatctc caaaaccaaa ggcagaccga aggctccaca ggtgtacacc   1140
attccacctc ccaaggagca gatggccaag gataaagtca gtctgacctg catgataaca   1200
gacttcttcc ctgaagacat tactgtggag tggcagtgga atgggcagcc agcggagaac   1260
tacaagaaca ctcagcccat catggacaca gatggctctt acttcgtcta cagcaagctc   1320
aatgtgcaga gagcaactg ggaggcagga atactttca cctgctctgt gttacatgag   1380
ggcctgcaca accaccatac tgagaagagc ctctcccact ctcctggtaa atga         1434
```

<210> SEQ ID NO 21
<211> LENGTH: 837
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21

| atgaaatacc | tgctgccgac | cgctgctgct | ggtctgctgc | tcctcgctgc | ccagccggcg | 60 |
| atggccgata | ttaaaatgac | gcagtctccg | agcagtatgt | acgcaagcct | gggtgaacgt | 120 |
| gtgacgatta | cctgtaaagc | ctctcaagat | atcaaatcct | atctgtcatg | gcatcagcaa | 180 |
| aaaccgtgga | aaagcccgaa | aaccctgatt | tattacgcaa | cgtcactggc | tgatggcgtg | 240 |
| ccgtcgcgtt | tttcaggttc | gggcagcggt | caggattata | gcctgaccat | cagctctctg | 300 |
| gaatctgatg | acaccgcgac | gtattactgc | ctgcaacacg | gtaaaagccc | gtacaccttc | 360 |
| ggcggtggca | cgaaactgga | aattaaaggt | ggcggtggct | ctggtggcgg | tggcagtggt | 420 |
| ggcggtggct | cccagatcca | actggtccag | agtggcccgg | aactgaaaaa | accgggtgaa | 480 |
| accgtgaaaa | tttcctgtaa | agcgtcgggc | tatagcttta | ccacgtacgg | tatgagttgg | 540 |
| gttaaacagg | ccccgggcaa | aggtctgaaa | tggatgggct | ggatcaacac | ctattctggt | 600 |
| gtcccgacgt | acgcagatga | ctttaaaggc | cgtttcgcgt | ttttcctgga | aacctctgcg | 660 |
| agtacggcct | atctgcagat | caacaacctg | aaaaacgaag | ataccgcgac | gtatttctgc | 720 |
| gcacgttggg | tggactactg | gggtcaaggt | accacgctga | ccgttagttc | cgaacaaaaa | 780 |
| ctgattagtg | aagaagacct | gaatatgcac | acgggccacc | accaccaca | ccattaa | 837 |

<210> SEQ ID NO 22
<211> LENGTH: 834
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22

| atggaaaccg | atacactgct | gctgtgggtc | ctgctgctgt | gggtgcccgg | gtcaactggc | 60 |
| gatgacatca | gatgacaca | gagtccctct | agtatgtacg | catcactggg | cgagagggtg | 120 |
| accatcacat | gtaaagcctc | tcaggatatt | aagagttatc | tgtcatggca | ccagcagaag | 180 |
| ccctggaaaa | gccctaagac | actgatctac | tatgcaacta | gctggcagac | ggagtccca | 240 |
| tcccggttca | gtgggtcagg | aagcggccag | gattactctc | tgaccatttc | aagcctggaa | 300 |
| agtgacgata | ctgccaccta | ctattgtctg | cagcatggca | agagccctta | tacctttggc | 360 |
| gggggaacaa | aactggagat | caagggcgga | ggaggcagcg | gaggaggagg | gtccggagga | 420 |
| ggaggatctc | agattcagct | ggtccagagc | ggcccagagc | tgaagaaacc | cggggaaacc | 480 |
| gtgaaaatca | gctgcaaggc | ttccgggtac | tctttcacca | catatggaat | gtcctgggtc | 540 |
| aagcaggcac | ctggcaaggg | gctgaaatgg | atgggctgga | ttaacactta | ctccggggtg | 600 |
| ccaacctatg | ccgacgattt | caaaggccgg | tttgcttttc | ttctggagac | atccgcctct | 660 |
| actgcttacc | tgcagatcaa | caatctgaag | aatgaagaca | cagctactta | cttttgcgca | 720 |
| agatgggtgg | attattgggg | acagggaact | accctgaccg | tcagctccga | acagaaactg | 780 |
| atttccgagg | aggacctgaa | catgcacact | gggcaccacc | accaccacca | ctaa | 834 |

<210> SEQ ID NO 23
<211> LENGTH: 270
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

```
Met Gln Leu Leu Ser Cys Ile Ala Leu Ser Leu Ala Leu Val Thr Asn
1               5                   10                  15

Ser Asp Ile Gln Met Thr Gln Ser Pro Ser Ser Leu Ser Ala Ser Val
            20                  25                  30

Gly Asp Arg Val Thr Ile Thr Cys Arg Ala Ser Gln Ser Val Ser Ser
        35                  40                  45

Ala Asp Ile Lys Met Thr Gln Ser Pro Ser Ser Met Tyr Ala Ser Leu
    50                  55                  60

Gly Glu Arg Val Thr Ile Thr Cys Lys Ala Ser Gln Asp Ile Lys Ser
65                  70                  75                  80

Tyr Leu Ser Trp His Gln Gln Lys Pro Trp Lys Ser Pro Lys Thr Leu
                85                  90                  95

Ile Tyr Tyr Ala Thr Ser Leu Ala Asp Gly Val Pro Ser Arg Phe Ser
            100                 105                 110

Gly Ser Gly Ser Gly Gln Asp Tyr Ser Leu Thr Ile Ser Ser Leu Glu
        115                 120                 125

Ser Asp Asp Thr Ala Thr Tyr Tyr Cys Leu Gln His Gly Lys Ser Pro
    130                 135                 140

Tyr Thr Phe Gly Gly Gly Thr Lys Leu Glu Ile Lys Gly Thr Lys Val
145                 150                 155                 160

Glu Ile Lys Arg Thr Val Ala Ala Pro Ser Val Phe Ile Phe Pro Pro
                165                 170                 175

Ser Asp Ser Gln Leu Lys Ser Gly Thr Ala Ser Val Val Cys Leu Leu
            180                 185                 190

Asn Asn Phe Tyr Pro Arg Glu Ala Lys Val Gln Trp Lys Val Asp Asn
        195                 200                 205

Ala Leu Gln Ser Gly Asn Ser Gln Glu Ser Val Thr Glu Gln Asp Ser
    210                 215                 220

Lys Asp Ser Thr Tyr Ser Leu Ser Ser Thr Leu Thr Leu Ser Lys Ala
225                 230                 235                 240

Asp Tyr Glu Lys His Lys Val Tyr Ala Cys Glu Val Thr His Gln Gly
                245                 250                 255

Leu Ser Ser Pro Val Thr Lys Ser Phe Asn Arg Gly Glu Cys
            260                 265                 270
```

<210> SEQ ID NO 24
<211> LENGTH: 477
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 24

```
Met Tyr Arg Met Gln Leu Leu Ser Cys Ile Ala Leu Ser Leu Ala Leu
1               5                   10                  15

Val Thr Asn Ser Glu Val Gln Leu Val Glu Gln Ile Gln Leu Val Gln
            20                  25                  30
```

```
Ser Gly Pro Glu Leu Lys Lys Pro Gly Glu Thr Val Lys Ile Ser Cys
         35                  40                  45
Lys Ala Ser Gly Tyr Ser Phe Thr Thr Tyr Gly Met Ser Trp Val Lys
 50                  55                  60
Gln Ala Pro Gly Lys Gly Leu Lys Trp Met Gly Trp Ile Asn Thr His
 65                  70                  75                  80
Ser Gly Val Pro Thr Tyr Ala Asp Asp Phe Lys Gly Arg Phe Ala Phe
                 85                  90                  95
Phe Leu Glu Thr Ser Ala Ser Thr Ala Tyr Leu Gln Ile Asn Asn Leu
             100                 105                 110
Lys Asn Glu Asp Thr Ala Thr Tyr Phe Cys Ala Arg Trp Val Asp Tyr
             115                 120                 125
Trp Gly Gln Gly Thr Thr Leu Thr Val Ser Ser Gly Thr Leu Val Thr
130                 135                 140
Val Ser Ser Ala Ser Thr Lys Gly Pro Ser Val Phe Pro Leu Ala Pro
145                 150                 155                 160
Ser Ser Lys Ser Thr Ser Gly Gly Thr Ala Ala Leu Gly Cys Leu Val
                 165                 170                 175
Lys Asp Tyr Phe Pro Glu Pro Val Thr Val Ser Trp Asn Ser Gly Ala
             180                 185                 190
Leu Thr Ser Gly Val His Thr Phe Pro Ala Val Leu Gln Ser Ser Gly
             195                 200                 205
Leu Tyr Ser Leu Ser Ser Val Val Thr Val Pro Ser Ser Ser Leu Gly
             210                 215                 220
Thr Gln Thr Tyr Ile Cys Asn Val Asn His Lys Pro Ser Asn Thr Lys
225                 230                 235                 240
Val Asp Lys Lys Val Glu Pro Lys Ser Cys Asp Lys Thr His Thr Cys
                 245                 250                 255
Pro Pro Cys Pro Ala Pro Glu Leu Leu Gly Gly Pro Ser Val Phe Ile
             260                 265                 270
Phe Pro Pro Lys Pro Lys Asp Val Leu Thr Ile Thr Leu Thr Pro Lys
             275                 280                 285
Val Thr Cys Val Val Val Asp Ile Ser Lys Asp Asp Pro Glu Val Gln
290                 295                 300
Phe Ser Trp Phe Val Asp Asp Val Glu Val His Thr Ala Gln Thr Gln
305                 310                 315                 320
Pro Arg Glu Glu Gln Phe Asn Ser Thr Phe Arg Ser Val Ser Glu Leu
                 325                 330                 335
Pro Ile Met His Gln Asp Trp Leu Asn Gly Lys Glu Phe Lys Cys Arg
             340                 345                 350
Val Asn Ser Ala Ala Phe Pro Ala Pro Ile Glu Lys Thr Ile Ser Lys
             355                 360                 365
Thr Lys Gly Arg Pro Lys Ala Pro Gln Val Tyr Thr Ile Pro Pro Pro
             370                 375                 380
Lys Glu Gln Met Ala Lys Asp Lys Val Ser Leu Thr Cys Met Ile Thr
385                 390                 395                 400
Asp Phe Phe Pro Glu Asp Ile Thr Val Glu Trp Gln Trp Asn Gly Gln
                 405                 410                 415
Pro Ala Glu Asn Tyr Lys Asn Thr Gln Pro Ile Met Asp Thr Asp Gly
             420                 425                 430
Ser Tyr Phe Val Tyr Ser Lys Leu Asn Val Gln Lys Ser Asn Trp Glu
             435                 440                 445
Ala Gly Asn Thr Phe Thr Cys Ser Val Leu His Glu Gly Leu His Asn
```

```
                450                 455                 460
His His Thr Glu Lys Ser Leu Ser His Ser Pro Gly Lys
465                 470                 475

<210> SEQ ID NO 25
<211> LENGTH: 278
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Met Lys Tyr Leu Leu Pro Thr Ala Ala Ala Gly Leu Leu Leu Leu Ala
1               5                   10                  15

Ala Gln Pro Ala Met Ala Asp Ile Lys Met Thr Gln Ser Pro Ser Ser
                20                  25                  30

Met Tyr Ala Ser Leu Gly Glu Arg Val Thr Ile Thr Cys Lys Ala Ser
            35                  40                  45

Gln Asp Ile Lys Ser Tyr Leu Ser Trp His Gln Gln Lys Pro Trp Lys
        50                  55                  60

Ser Pro Lys Thr Leu Ile Tyr Tyr Ala Thr Ser Leu Ala Asp Gly Val
65                  70                  75                  80

Pro Ser Arg Phe Ser Gly Ser Gly Ser Gly Gln Asp Tyr Ser Leu Thr
                85                  90                  95

Ile Ser Ser Leu Glu Ser Asp Asp Thr Ala Thr Tyr Tyr Cys Leu Gln
            100                 105                 110

His Gly Lys Ser Pro Tyr Thr Phe Gly Gly Gly Thr Lys Leu Glu Ile
        115                 120                 125

Lys Gly Gly Gly Gly Ser Gly Gly Gly Gly Ser Gly Gly Gly Gly Ser
130                 135                 140

Gln Ile Gln Leu Val Gln Ser Gly Pro Glu Leu Lys Lys Pro Gly Glu
145                 150                 155                 160

Thr Val Lys Ile Ser Cys Lys Ala Ser Gly Tyr Ser Phe Thr Thr Tyr
                165                 170                 175

Gly Met Ser Trp Val Lys Gln Ala Pro Gly Lys Gly Leu Lys Trp Met
            180                 185                 190

Gly Trp Ile Asn Thr Tyr Ser Gly Val Pro Thr Tyr Ala Asp Asp Phe
        195                 200                 205

Lys Gly Arg Phe Ala Phe Phe Leu Glu Thr Ser Ala Ser Thr Ala Tyr
    210                 215                 220

Leu Gln Ile Asn Asn Leu Lys Asn Glu Asp Thr Ala Thr Tyr Phe Cys
225                 230                 235                 240

Ala Arg Trp Val Asp Tyr Trp Gly Gln Gly Thr Thr Leu Thr Val Ser
                245                 250                 255

Ser Glu Gln Lys Leu Ile Ser Glu Glu Asp Leu Asn Met His Thr Gly
            260                 265                 270

His His His His His His
        275

<210> SEQ ID NO 26
<211> LENGTH: 277
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 26

```
Met Glu Thr Asp Thr Leu Leu Leu Trp Val Leu Leu Leu Trp Val Pro
1               5                   10                  15
Gly Ser Thr Gly Asp Asp Ile Lys Met Thr Gln Ser Pro Ser Ser Met
            20                  25                  30
Tyr Ala Ser Leu Gly Glu Arg Val Thr Ile Thr Cys Lys Ala Ser Gln
        35                  40                  45
Asp Ile Lys Ser Tyr Leu Ser Trp His Gln Lys Pro Trp Lys Ser
    50                  55                  60
Pro Lys Thr Leu Ile Tyr Tyr Ala Thr Ser Leu Ala Asp Gly Val Pro
65                  70                  75                  80
Ser Arg Phe Ser Gly Ser Gly Ser Gly Gln Asp Tyr Ser Leu Thr Ile
                85                  90                  95
Ser Ser Leu Glu Ser Asp Asp Thr Ala Thr Tyr Tyr Cys Leu Gln His
            100                 105                 110
Gly Lys Ser Pro Tyr Thr Phe Gly Gly Gly Thr Lys Leu Glu Ile Lys
        115                 120                 125
Gly Gly Gly Gly Ser Gly Gly Gly Ser Gly Gly Gly Ser Gln
    130                 135                 140
Ile Gln Leu Val Gln Ser Gly Pro Glu Leu Lys Lys Pro Gly Glu Thr
145                 150                 155                 160
Val Lys Ile Ser Cys Lys Ala Ser Gly Tyr Ser Phe Thr Thr Tyr Gly
                165                 170                 175
Met Ser Trp Val Lys Gln Ala Pro Gly Lys Gly Leu Lys Trp Met Gly
            180                 185                 190
Trp Ile Asn Thr Tyr Ser Gly Val Pro Thr Tyr Ala Asp Asp Phe Lys
        195                 200                 205
Gly Arg Phe Ala Phe Phe Leu Glu Thr Ser Ala Ser Thr Ala Tyr Leu
    210                 215                 220
Gln Ile Asn Asn Leu Lys Asn Glu Asp Thr Ala Thr Tyr Phe Cys Ala
225                 230                 235                 240
Arg Trp Val Asp Tyr Trp Gly Gln Gly Thr Thr Leu Thr Val Ser Ser
                245                 250                 255
Glu Gln Lys Leu Ile Ser Glu Glu Asp Leu Asn Met His Thr Gly His
            260                 265                 270
His His His His His
        275
```

<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 27

```
His His His His His His
1               5
```

<210> SEQ ID NO 28
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 28

Gly Gly Gly Gly Ser Gly Gly Gly Ser Gly Gly Gly Gly Ser
1               5                   10                  15

<210> SEQ ID NO 29
<211> LENGTH: 45
<212> TYPE: PRT
<213> ORGANISM: Homo sapiens

<400> SEQUENCE: 29

Gln Asp Thr Glu Glu Thr Ile Thr Tyr Thr Gln Cys Thr Asp Gly Tyr
1               5                   10                  15

Glu Trp Asp Pro Val Arg Gln Gln Cys Lys Asp Ile Asp Glu Cys Asp
                20                  25                  30

Ile Val Pro Asp Ala Cys Lys Gly Gly Met Lys Cys Val
            35                  40                  45

<210> SEQ ID NO 30
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gln Asp Thr Glu Glu Thr Ile Cys Asp Ile Val Pro Asp Ala Cys Lys
1               5                   10                  15

Gly Gly Met Lys Cys Val
            20

<210> SEQ ID NO 31
<211> LENGTH: 33
<212> TYPE: PRT
<213> ORGANISM: Homo sapiens

<400> SEQUENCE: 31

Ile Thr Tyr Thr Gln Cys Thr Asp Gly Tyr Glu Trp Asp Pro Val Arg
1               5                   10                  15

Gln Gln Cys Lys Asp Ile Asp Glu Cys Asp Ile Val Pro Asp Ala Cys
                20                  25                  30

Lys

<210> SEQ ID NO 32
<211> LENGTH: 33
<212> TYPE: PRT
<213> ORGANISM: Rattus norvegicus

<400> SEQUENCE: 32

Ile Thr Tyr Thr Gln Cys Thr Asp Gly Tyr Glu Trp Asp Pro Val Arg
1               5                   10                  15

Gln Gln Cys Lys Asp Ile Asp Glu Cys Asp Ile Val Pro Asp Ala Cys
                20                  25                  30

Lys

<210> SEQ ID NO 33
<211> LENGTH: 33
<212> TYPE: PRT
<213> ORGANISM: Mus musculus

<400> SEQUENCE: 33
```

```
Ile Thr Tyr Thr Gln Cys Thr Asp Gly Tyr Glu Trp Asp Pro Ile Arg
1               5                   10                  15

Gln Gln Cys Lys Asp Ile Asp Glu Cys Asp Ile Val Pro Asp Ala Cys
            20                  25                  30

Lys

<210> SEQ ID NO 34
<211> LENGTH: 33
<212> TYPE: PRT
<213> ORGANISM: Bos taurus

<400> SEQUENCE: 34

Ile Thr Tyr Thr Gln Cys Thr Asp Gly Tyr Glu Trp Asp Pro Val Arg
1               5                   10                  15

Gln Gln Cys Lys Asp Ile Asp Glu Cys Asp Ile Val Pro Asp Ala Cys
            20                  25                  30

Lys

<210> SEQ ID NO 35
<211> LENGTH: 33
<212> TYPE: PRT
<213> ORGANISM: Canis familiaris

<400> SEQUENCE: 35

Ile Thr Tyr Thr Gln Cys Thr Asp Gly Tyr Glu Trp Asp Pro Val Arg
1               5                   10                  15

Gln Gln Cys Lys Asp Ile Asp Glu Cys Asp Ile Val Pro Asp Ala Cys
            20                  25                  30

Lys

<210> SEQ ID NO 36
<211> LENGTH: 23
<212> TYPE: PRT
<213> ORGANISM: Unknown
<220> FEATURE:
<223> OTHER INFORMATION: Description of Unknown: fibulin-3
      peptide

<400> SEQUENCE: 36

Thr Tyr Thr Gln Cys Thr Asp Gly Tyr Glu Trp Asp Pro Val Arg Gln
1               5                   10                  15

Gln Cys Lys Asp Ile Asp Glu
            20

<210> SEQ ID NO 37
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (6)..(19)
<223> OTHER INFORMATION: Cyclic
<220> FEATURE:
<223> OTHER INFORMATION: N-term amide

<400> SEQUENCE: 37

Lys Thr Tyr Thr Gln Cys Thr Asp Gly Tyr Glu Trp Asp Pro Val Arg
1               5                   10                  15

Gln Gln Cys Lys Asp Ile Asp Glu
            20
```

<210> SEQ ID NO 38
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 38

```
Met Tyr Arg Met Gln Leu Leu Ser Cys Ile Ala Leu Ser Leu Ala Leu
1               5                   10                  15

Val Thr Asn Ser Glu Val Gln
            20
```

<210> SEQ ID NO 39
<211> LENGTH: 336
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 39

```
Leu Val Thr Val Ser Ser Ala Ser Thr Lys Gly Pro Ser Val Phe Pro
1               5                   10                  15

Leu Ala Pro Ser Ser Lys Ser Thr Ser Gly Gly Thr Ala Ala Leu Gly
            20                  25                  30

Cys Leu Val Lys Asp Tyr Phe Pro Glu Pro Val Thr Val Ser Trp Asn
        35                  40                  45

Ser Gly Ala Leu Thr Ser Gly Val His Thr Phe Pro Ala Val Leu Gln
    50                  55                  60

Ser Ser Gly Leu Tyr Ser Leu Ser Val Val Thr Val Pro Ser Ser
65                  70                  75                  80

Ser Leu Gly Thr Gln Thr Tyr Ile Cys Asn Val Asn His Lys Pro Ser
                85                  90                  95

Asn Thr Lys Val Asp Lys Lys Val Glu Pro Lys Ser Cys Asp Lys Thr
            100                 105                 110

His Thr Cys Pro Pro Cys Pro Ala Pro Glu Leu Leu Gly Gly Pro Ser
        115                 120                 125

Val Phe Ile Phe Pro Pro Lys Pro Lys Asp Val Leu Thr Ile Thr Leu
    130                 135                 140

Thr Pro Lys Val Thr Cys Val Val Val Asp Ile Ser Lys Asp Asp Pro
145                 150                 155                 160

Glu Val Gln Phe Ser Trp Phe Val Asp Asp Val Glu Val His Thr Ala
                165                 170                 175

Gln Thr Gln Pro Arg Glu Glu Gln Phe Asn Ser Thr Phe Arg Ser Val
            180                 185                 190

Ser Glu Leu Pro Ile Met His Gln Asp Trp Leu Asn Gly Lys Glu Phe
        195                 200                 205

Lys Cys Arg Val Asn Ser Ala Ala Phe Pro Ala Pro Ile Glu Lys Thr
    210                 215                 220

Ile Ser Lys Thr Lys Gly Arg Pro Lys Ala Pro Gln Val Tyr Thr Ile
225                 230                 235                 240

Pro Pro Pro Lys Glu Gln Met Ala Lys Asp Lys Val Ser Leu Thr Cys
                245                 250                 255

Met Ile Thr Asp Phe Phe Pro Glu Asp Ile Thr Val Glu Trp Gln Trp
            260                 265                 270
```

Asn Gly Gln Pro Ala Glu Asn Tyr Lys Asn Thr Gln Pro Ile Met Asp
            275                 280                 285

Thr Asp Gly Ser Tyr Phe Val Tyr Ser Lys Leu Asn Val Gln Lys Ser
    290                 295                 300

Asn Trp Glu Ala Gly Asn Thr Phe Thr Cys Ser Val Leu His Glu Gly
305                 310                 315                 320

Leu His Asn His His Thr Glu Lys Ser Leu Ser His Ser Pro Gly Lys
                325                 330                 335

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
attcggaggt tcagctggtg gag                                              23

<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gagacggtga ccagggttc                                                   19

<210> SEQ ID NO 42
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
acagatccaa gctgtgacc                                                   19

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agtagtcctt gaccaggcag                                                  20

<210> SEQ ID NO 44
<211> LENGTH: 140
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (68)..(136)

<400> SEQUENCE: 44

-continued

```
tctgcgccgt tacagatcca agctgtgacc ggcgcctacc tgagatcacc ggcgaaggag      60 ggccacc atg tac agg atg caa ctc ctg tct tgc att gca cta agt ctt        109
        Met Tyr Arg Met Gln Leu Leu Ser Cys Ile Ala Leu Ser Leu
        1               5                   10 gca ctt gtc acg aat tcg gag gtt cag cgct                                140
Ala Leu Val Thr Asn Ser Glu Val Gln
15                  20

<210> SEQ ID NO 45
<211> LENGTH: 1100
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (7)..(1014)

<400> SEQUENCE: 45 gcatgc ctg gtc acc gtc tcc tcg gcc tcc acc aag ggt cca tcg gtc         48
       Leu Val Thr Val Ser Ser Ala Ser Thr Lys Gly Pro Ser Val
       1               5                   10 ttc ccc ctg gca ccc tcc tcc aag agc acc tct ggg ggc aca gcg gcc        96
Phe Pro Leu Ala Pro Ser Ser Lys Ser Thr Ser Gly Gly Thr Ala Ala
15                  20                  25                  30 ctg ggc tgc ctg gtc aag gac tac ttc ccc gaa ccg gtg acg gtg tcg        144
Leu Gly Cys Leu Val Lys Asp Tyr Phe Pro Glu Pro Val Thr Val Ser
                35                  40                  45 tgg aac tca ggc gcc ctg acc agc ggc gtg cac acc ttc ccg gct gtc        192
Trp Asn Ser Gly Ala Leu Thr Ser Gly Val His Thr Phe Pro Ala Val
            50                  55                  60 cta cag tcc tca gga ctc tac tcc ctc agc agc gtg gtg acc gtg ccc        240
Leu Gln Ser Ser Gly Leu Tyr Ser Leu Ser Ser Val Val Thr Val Pro
        65                  70                  75 tcc agc agc ttg ggc acc cag acc tac atc tgc aac gtg aat cac aag        288
Ser Ser Ser Leu Gly Thr Gln Thr Tyr Ile Cys Asn Val Asn His Lys
    80                  85                  90 ccc agc aac acc aag gtc gac aag aaa gtt gag ccc aaa tct tgt gac        336
Pro Ser Asn Thr Lys Val Asp Lys Lys Val Glu Pro Lys Ser Cys Asp
95                  100                 105                 110 aaa act cac aca tgc cct cca tgt cca gcc cct gaa ctt ctg gga gga        384
Lys Thr His Thr Cys Pro Pro Cys Pro Ala Pro Glu Leu Leu Gly Gly
                115                 120                 125 cct tct gtc ttc atc ttc ccc cca aag ccc aag gat gtg ctc acc att        432
Pro Ser Val Phe Ile Phe Pro Pro Lys Pro Lys Asp Val Leu Thr Ile
            130                 135                 140 act ctg act cct aag gtc acg tgt gtt gtg gta gac atc agc aag gat        480
Thr Leu Thr Pro Lys Val Thr Cys Val Val Val Asp Ile Ser Lys Asp
        145                 150                 155 gat ccc gag gtc cag ttc agc tgg ttt gta gat gat gtg gag gtg cac        528
Asp Pro Glu Val Gln Phe Ser Trp Phe Val Asp Asp Val Glu Val His
    160                 165                 170 aca gct cag acg caa ccc cgg gag gag cag ttc aac agc act ttc cgc        576
Thr Ala Gln Thr Gln Pro Arg Glu Glu Gln Phe Asn Ser Thr Phe Arg
175                 180                 185                 190 tca gtc agt gaa ctt ccc atc atg cac cag gac tgg ctc aat ggc aag        624
Ser Val Ser Glu Leu Pro Ile Met His Gln Asp Trp Leu Asn Gly Lys
                195                 200                 205 gag ttc aaa tgc agg gtc aac agt gca gct ttc cct gcc ccc atc gag        672
Glu Phe Lys Cys Arg Val Asn Ser Ala Ala Phe Pro Ala Pro Ile Glu
            210                 215                 220
```

```
aaa acc atc tcc aaa acc aaa ggc aga ccg aag gct cca cag gtg tac        720
Lys Thr Ile Ser Lys Thr Lys Gly Arg Pro Lys Ala Pro Gln Val Tyr
            225                 230                 235 acc att cca cct ccc aag gag cag atg gcc aag gat aaa gtc agt ctg        768
Thr Ile Pro Pro Pro Lys Glu Gln Met Ala Lys Asp Lys Val Ser Leu
        240                 245                 250 acc tgc atg ata aca gac ttc ttc cct gaa gac att act gtg gag tgg        816
Thr Cys Met Ile Thr Asp Phe Phe Pro Glu Asp Ile Thr Val Glu Trp
255                 260                 265                 270 cag tgg aat ggg cag cca gcg gag aac tac aag aac act cag ccc atc        864
Gln Trp Asn Gly Gln Pro Ala Glu Asn Tyr Lys Asn Thr Gln Pro Ile
            275                 280                 285 atg gac aca gat ggc tct tac ttc gtc tac agc aag ctc aat gtg cag        912
Met Asp Thr Asp Gly Ser Tyr Phe Val Tyr Ser Lys Leu Asn Val Gln
        290                 295                 300 aag agc aac tgg gag gca gga aat act ttc acc tgc tct gtg tta cat        960
Lys Ser Asn Trp Glu Ala Gly Asn Thr Phe Thr Cys Ser Val Leu His
305                 310                 315 gag ggc ctg cac aac cac cat act gag aag agc ctc tcc cac tct cct       1008
Glu Gly Leu His Asn His His Thr Glu Lys Ser Leu Ser His Ser Pro
            320                 325                 330 ggt aaa tgatcccagt gtccctagct ggccagacat gataagatac attgatgagt        1064
Gly Lys
335 ttggacaaac cacaactaga atgcagtgaa aaaaat                                1100

<210> SEQ ID NO 46
<211> LENGTH: 6510
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 46
ggatctgcga tcgctccggt gcccgtcagt gggcagagcg cacatcgccc acagtccccg       60
agaagttggg gggaggggtc ggcaattgaa cgggtgccta gagaaggtgg cgcggggtaa      120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc gcctcccgc ctgtggtgcc tcctgaactg      360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacctgaga tcaccggcga aggagggcca ccatgtacag gatgcaactc ctgtcttgca     600
ttgcactaag tcttgcactt gtcacgaatt cggaggttca gcgctctgaa agatccataa     660
cttcgtatag catacattat acgaagttat gcggccgcga cgtccacata tacctgccgt    720
tcactattat ttagtgaaat gagatattat gatattttct gaattgtgat taaaaggca     780 actttatgcc catgcaacag aaactataaa aaatacagag aatgaaaaga aacagataga    840
ttttttagtt ctttaggccc gtagtctgca aatcctttta tgattttcta tcaaacaaaa   900
gaggaaaata gaccagttgc aatccaaacg agagtctaat agaatgaggt cgaaaagtaa   960
atcgcgcggg tttgttactg ataaagcagg caagacctaa aatgtgtaaa gggcaaagtg  1020
```

```
tatactttgg cgtcacccct tacatatttt aggtcttttt ttattgtgcg taactaactt    1080
gccatcttca aacaggaggg ctggaagaag cagaccgcta acacagtaca taaaaaagga    1140
gacatgaacg atgaacatca aaagtttgc aaaacaagca acagtattaa cctttactac    1200
cgcactgctg gcaggaggcg caactcaagc gtttgcgaaa gaaacgaacc aaaagccata    1260
taaggaaaca tacggcattt cccatattac acgccatgat atgctgcaaa tccctgaaca    1320
gcaaaaaaat gaaaaatatc aagttcctga gttcgattcg tccacaatta aaatatctc    1380
ttctgcaaaa ggcctggacg tttgggacag ctggccatta caaaacgctg acggcactgt    1440
cgcaaactat cacggctacc acatcgtctt tgcattagcc ggagatccta aaaatgcgga    1500
tgacacatcg atttacatgt tctatcaaaa agtcggcgaa acttctattg acagctggaa    1560
aaacgctggc cgcgtcttta aagacagcga caaattcgat gcaaatgatt ctatcctaaa    1620
agaccaaaca caagaatggt caggttcagc cacatttaca tctgacggaa aaatccgttt    1680
attctacact gatttctccg gtaaacatta cggcaaacaa acactgacaa ctgcacaagt    1740
taacgtatca gcatcagaca gctctttgaa catcaacggt gtagaggatt ataaatcaat    1800
ctttgacggt gacggaaaaa cgtatcaaaa tgtacagcag ttcatcgatg aaggcaacta    1860
cagctcaggc gacaaccata cgctgagaga tcctcactac gtagaagata aaggccacaa    1920
atacttagta tttgaagcaa acactggaac tgaagatggc taccaaggcg aagaatcttt    1980
atttaacaaa gcatactatg gcaaaagcac atcattcttc cgtcaagaaa gtcaaaaact    2040
tctgcaaagc gataaaaaac gcacggctga gttagcaaac ggcgctctcg gtatgattga    2100
gctaaacgat gattacacac tgaaaaaagt gatgaaaccg ctgattgcat ctaacacagt    2160
aacagatgaa attgaacgcg cgaacgtctt taaaatgaac ggcaaatggt acctgttcac    2220
tgactcccgc ggatcaaaaa tgacgattga cggcattacg tctaacgata tttacatgct    2280
tggttatgtt tctaattctt taactggccc atacaagccg ctgaacaaaa ctggccttgt    2340
gttaaaaatg gatcttgatc ctaacgatgt aacctttact tactcacact cgctgtacc    2400
tcaagcgaaa ggaaacaatg tcgtgattac aagctatatg acaaacagag gattctacgc    2460
agacaaacaa tcaacgtttg cgcctagctt cctgctgaac atcaaaggca agaaaacatc    2520
tgttgtcaaa gacagcatcc ttgaacaagg acaattaaca gttaacaaat aaaaacgcaa    2580
aagaaaatgc cgatatccta ttggcattga cgtcaggtgg cacttttcgc atgcctggtc    2640
accgtctcct cggcctccac caagggtcca tcggtcttcc ccctggcacc ctcctccaag    2700
agcacctctg ggggcacagc ggccctgggc tgcctggtca aggactactt ccccgaaccg    2760
gtgacggtgt cgtggaactc aggcgccctg accagcggcg tgcacacctt cccggctgtc    2820
ctacagtcct caggactcta ctccctcagc agcgtggtga ccgtgccctc cagcagcttg    2880
ggcacccaga cctacatctg caacgtgaat cacaagccca gcaacaccaa ggtcgacaag    2940
aaagttgagc ccaaatcttg tgacaaaact cacacatgcc ctccatgtcc agcccctgaa    3000
cttctgggag gaccttctgt cttcatcttc ccccaaagc ccaaggatgt gctcaccatt    3060
actctgactc ctaaggtcac gtgtgttgtg gtagacatca gcaaggatga tcccgaggtc    3120
cagttcagct ggtttgtaga tgatgtggag gtgcacacag ctcagacgca accccgggag    3180
gagcagttca acagcacttt ccgctcagtc agtgaacttc ccatcatgca ccaggactgg    3240
ctcaatggca aggagttcaa atgcagggtc aacagtgcag cttttcctgc ccccatcgag    3300
aaaaccatct ccaaaaccaa aggcagaccg aaggctccac aggtgtacac cattccacct    3360
```

```
cccaaggagc agatggccaa ggataaagtc agtctgacct gcatgataac agacttcttc    3420
cctgaagaca ttactgtgga gtggcagtgg aatgggcagc cagcggagaa ctacaagaac    3480
actcagccca tcatggacac agatggctct tacttcgtct acagcaagct caatgtgcag    3540
aagagcaact gggaggcagg aaatactttc acctgctctg tgttacatga gggcctgcac    3600
aaccaccata ctgagaagag cctctcccac tctcctggta aatgatccca gtgtccctag    3660
ctggccagac atgataagat acattgatga gtttggacaa accacaacta gaatgcagtg    3720
aaaaaaatgc tttatttgtg aaatttgtga tgctattgct ttatttgtaa ccattataag    3780
ctgcaataaa caagttaaca acaacaattg cattcatttt atgtttcagg ttcagggggga    3840 ggtgtgggag gttttttaaa gcaagtaaaa cctctacaaa tgtggtatgg aattaattct    3900
aaaatacagc atagcaaaac tttaacctcc aaatcaagcc tctacttgaa tccttttctg    3960
agggatgaat aaggcatagg catcaggggc tgttgccaat gtgcattagc tgtttgcagc    4020
ctcaccttct ttcatggagt ttaagatata gtgtattttc ccaaggtttg aactagctct    4080
tcatttcttt atgttttaaa tgcactgacc tcccacattc ccttttttagt aaaatattca    4140 gaataatttt aaatacatca ttgcaatgaa aataaatgtt ttttattagg cagaatccag    4200
atgctcaagg cccttcataa tatcccccag tttagtagtt ggacttaggg aacaaaggaa    4260
cctttaatag aaattggaca gcaagaaagc gagcttctag cttatcctca gtcctgctcc    4320
tctgccacaa agtgcacgca gttgccggcc gggtcgcgca gggcgaactc ccgcccccac    4380
ggctgctcgc cgatctcggt catggccggc ccggaggcgt cccggaagtt cgtggacacg    4440
acctccgacc actcggcgta cagctcgtcc aggccgcgca cccacaccca ggccagggtg    4500
ttgtccggca ccacctggtc ctggaccgcg ctgatgaaca gggtcacgtc gtcccggacc    4560
acaccggcga agtcgtcctc cacgaagtcc cgggagaacc cgagccggtc ggtccagaac    4620
tcgaccgctc cggcgacgtc gcgcgcggtg agcaccggaa cggcactggt caacttggcc    4680
atgatggctc ctcctgtcag gagaggaaag agaagaaggt tagtacaatt gctatagtga    4740
gttgtattat actatgcaga tatactatgc caatgattaa ttgtcaaact agggctgcag    4800
ggttcatagt gccactttttc ctgcactgcc ccatctcctg cccacccttt ccaggcata    4860 gacagtcagt gacttaccaa actcacagga gggagaaggc agaagcttga gacagacccg    4920
cgggaccgcc gaactgcgag gggacgtggc tagggcggct tctttttatgg tgcgccggcc    4980 ctcggaggca gggcgctcgg ggaggcctag cggccaatct gcggtggcag gaggcggggc    5040
cgaaggccgt gcctgaccaa tccggagcac ataggagtct cagcccccg ccccaaagca    5100 aggggaagtc acgcgcctgt agcgccagcg tgttgtgaaa tgggggcttg gggggggttgg    5160 ggccctgact agtcaaaaca aactcccatt gacgtcaatg gggtggagac ttggaaatcc    5220
ccgtgagtca aaccgctatc cacgcccatt gatgtactgc caaaaccgca tcatcatggt    5280
aatagcgatg actaatacgt agatgtactg ccaagtagga aagtcccata aggtcatgta    5340
ctgggcataa tgccaggcgg gccatttacc gtcattgacg tcaataggggg gcgtacttgg    5400 catatgatac acttgatgta ctgccaagtg gcagtttac cgtaaatact ccacccattg    5460
acgtcaatgg aaagtcccta ttggcgttac tatgggaaca tacgtcatta ttgacgtcaa    5520
tgggcggggg tcgttgggcg gtcagccagg cgggccattt accgtaagtt atgtaacgcc    5580
tgcaggttaa ttaagaacat gtgagcaaaa ggccagcaaa aggccaggaa ccgtaaaaag    5640
gccgcgttgc tggcgttttt ccataggctc cgccccctg acgagcatca aaaaatcga    5700 cgctcaagtc agaggtggcg aaacccgaca ggactataaa gataccaggc gtttccccct    5760
```

```
ggaagctccc tcgtgcgctc tcctgttccg accctgccgc ttaccggata cctgtccgcc   5820
tttctcccct cgggaagcgt ggcgctttct catagctcac gctgtaggta tctcagttcg   5880
gtgtaggtcg ttcgctccaa gctgggctgt gtgcacgaac cccccgttca gcccgaccgc   5940
tgcgccttat ccggtaacta tcgtcttgag tccaacccgg taagacacga cttatcgcca   6000
ctggcagcag ccactggtaa caggattagc agagcgaggt atgtaggcgg tgctacagag   6060
ttcttgaagt ggtggcctaa ctacggctac actagaagaa cagtatttgg tatctgcgct   6120
ctgctgaagc cagttacctt cggaaaaaga gttggtagct cttgatccgg caaacaaacc   6180
accgctggta gcggtggttt ttttgtttgc aagcagcaga ttacgcgcag aaaaaaagga   6240
tctcaagaag atcctttgat cttttctacg gggtctgacg ctcagtggaa cgaaaactca   6300
cgttaaggga ttttggtcat ggctagttaa ttaacattta aatcagcggc cgcaataaaa   6360
tatctttatt ttcattacat ctgtgtgttg gttttttgtg tgaatcgtaa ctaacatacg   6420
ctctccatca aaacaaaacg aaacaaaaca aactagcaaa ataggctgtc cccagtgcaa   6480
gtgcaggtgc cagaacattt ctctatcgaa                                    6510
```

<210> SEQ ID NO 47
<211> LENGTH: 52
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 47

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Ser
        35                  40                  45

Val Ser Ser Ala
    50

<210> SEQ ID NO 48
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 48

Gly Thr Lys Val Glu Ile Lys Arg Thr Val Ala Ala Pro Ser Val Phe
1               5                   10                  15

Ile Phe Pro Pro Ser Asp Ser Gln Leu Lys Ser Gly Thr Ala Ser Val
            20                  25                  30

Val Cys Leu Leu Asn Asn Phe Tyr Pro Arg Glu Ala Lys Val Gln Trp
        35                  40                  45

Lys Val Asp Asn Ala Leu Gln Ser Gly Asn Ser Gln Glu Ser Val Thr
    50                  55                  60

Glu Gln Asp Ser Lys Asp Ser Thr Tyr Ser Leu Ser Ser Thr Leu Thr
65                  70                  75                  80

Leu Ser Lys Ala Asp Tyr Glu Lys His Lys Val Tyr Ala Cys Glu Val
                85                  90                  95

Thr His Gln Gly Leu Ser Ser Pro Val Thr Lys Ser Phe Asn Arg Gly
            100                 105                 110

Glu Cys

<210> SEQ ID NO 49
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
cagtccgtgt ccagcgctg                                                  19

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
tttgatctcc accttggtac                                                 20

<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
acagatccaa gctgtgacc                                                  19

<210> SEQ ID NO 52
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
accttccact gtactttgg                                                  19

<210> SEQ ID NO 53
<211> LENGTH: 260
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (63)..(260)

<400> SEQUENCE: 53
acgtctttgt tcgtttctct gttacagatc caagctgtga ccggcgccta cctgagatca    60 ac atg tac agg atg caa ctc ctg tct tgc att gca cta agt ctt gca      107
   Met Tyr Arg Met Gln Leu Leu Ser Cys Ile Ala Leu Ser Leu Ala
   1               5                   10                  15 ctt gtc acg aat tca gat atc cag atg acc cag tcc ccg agc tcc ctg    155
Leu Val Thr Asn Ser Asp Ile Gln Met Thr Gln Ser Pro Ser Ser Leu

```
                20                  25                  30
tcc gcc tct gtg ggc gat agg gtc acc atc acc tgc cgt gcc agt cag        203
Ser Ala Ser Val Gly Asp Arg Val Thr Ile Thr Cys Arg Ala Ser Gln
            35                  40                  45 tcc gtg tcc agc gct gta gcc tgg tat caa cag aaa cca gga aaa gct        251
Ser Val Ser Ser Ala Val Ala Trp Tyr Gln Gln Lys Pro Gly Lys Ala
        50                  55                  60 ccg aag ctt                                                            260
Pro Lys Leu
    65

<210> SEQ ID NO 54
<211> LENGTH: 380
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(342)

<400> SEQUENCE: 54 ggt acc aag gtg gag atc aaa cga act gtg gct gca cca tct gtc ttc         48
Gly Thr Lys Val Glu Ile Lys Arg Thr Val Ala Ala Pro Ser Val Phe
1               5                   10                  15 atc ttc ccg cca tct gat tca cag ttg aaa tct gga act gcc tct gtt         96
Ile Phe Pro Pro Ser Asp Ser Gln Leu Lys Ser Gly Thr Ala Ser Val
            20                  25                  30 gtg tgc ctg ctg aat aac ttc tat ccc aga gag gcc aaa gta cag tgg        144
Val Cys Leu Leu Asn Asn Phe Tyr Pro Arg Glu Ala Lys Val Gln Trp
        35                  40                  45 aag gtg gat aac gcc ctc caa tcg ggt aac tcc cag gag agt gtc aca        192
Lys Val Asp Asn Ala Leu Gln Ser Gly Asn Ser Gln Glu Ser Val Thr
    50                  55                  60 gag cag gac agc aag gac agc acc tac agc ctc agc agc acc ctg acg        240
Glu Gln Asp Ser Lys Asp Ser Thr Tyr Ser Leu Ser Ser Thr Leu Thr
65                  70                  75                  80 ctg agc aaa gca gac tac gaa aaa cat aaa gtc tac gcc tgc gaa gtc        288
Leu Ser Lys Ala Asp Tyr Glu Lys His Lys Val Tyr Ala Cys Glu Val
                85                  90                  95 acc cat cag ggc ctg agc tcg ccc gtc aca aag agc ttc aac agg gga        336
Thr His Gln Gly Leu Ser Ser Pro Val Thr Lys Ser Phe Asn Arg Gly
            100                 105                 110 gag tgt tagagacaaa ggtcctgaga gctagctggc cagacatg                      380
Glu Cys <210> SEQ ID NO 55
<211> LENGTH: 66
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 55

Met Tyr Arg Met Gln Leu Leu Ser Cys Ile Ala Leu Ser Leu Ala Leu
1               5                   10                  15

Val Thr Asn Ser Asp Ile Gln Met Thr Gln Ser Pro Ser Ser Leu Ser
            20                  25                  30

Ala Ser Val Gly Asp Arg Val Thr Ile Thr Cys Arg Ala Ser Gln Ser
        35                  40                  45
```

Val Ser Ser Ala Val Ala Trp Tyr Gln Gln Lys Pro Gly Lys Ala Pro
    50                  55                  60

Lys Leu
65

<210> SEQ ID NO 56
<211> LENGTH: 5983
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 56

```
ggatctgcga tcgctccggt gcccgtcagt gggcagagcg cacatcgccc acagtccccg     60
agaagttggg gggaggggtc ggcaattgaa cgggtgccta gagaaggtgg cgcggggtaa    120
actgggaaag tgatgtcgtg tactggctcc gccttttttcc cgagggtggg ggagaaccgt   180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc tgtggtgcc tcctgaactg     360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacctgaga tcaacatgta caggatgcaa ctcctgtctt gcattgcact aagtcttgca    600
cttgtcacga attcagatat ccagatgacc cagtccccga gctccctgtc cgcctctgtg    660
ggcgataggg tcaccatcac ctgccgtgcc agtcagtccg tgtccagcgc gtagcctgg    720
tatcaacaga accaggaaa agctccgaag cttctgaaag atccataact tcgtatagca    780
tacattatac gaagttatgc ggccgcgacg tccacatata cctgccgttc actattattt    840
agtgaaatga gatattatga tattttctga attgtgatta aaaaggcaac tttatgccca    900
tgcaacagaa actataaaaa atacagagaa tgaaaagaaa cagatagatt tttagttct   960
ttaggcccgt agtctgcaaa tccttttatg attttctatc aaacaaaga ggaaaataga   1020
ccagttgcaa tccaaacgag agtctaatag aatgaggtcg aaaagtaaat cgcgcgggtt   1080
tgttactgat aaagcaggca agacctaaaa tgtgtaaagg gcaaagtgta tactttggcg   1140
tcaccccta catattttag gtctttttttt attgtgcgta actaacttgc catcttcaaa   1200
caggagggct ggaagaagca gaccgctaac acagtacata aaaaggaga catgaacgat    1260
gaacatcaaa agtttgcaa aacaagcaac agtattaacc tttactaccg cactgctggc   1320
aggaggcgca actcaagcgt tgcgaaaga acgaaccaa aagccatata aggaaacata    1380
cggcatttcc catattacac gccatgatat gctgcaaatc cctgaacagc aaaaaatga    1440
aaaatatcaa gttcctgagt tcgattcgtc cacaattaaa aatatctctt ctgcaaaagg    1500
cctggacgtt tgggacagct ggccattaca aaacgctgac ggcactgtcg caaactatca    1560
cggctaccac atcgtctttg cattagccgg agatcctaaa aatgcggatg acacatcgat    1620
ttacatgttc tatcaaaaag tcggcgaaac ttcttattga cagctggaaaa acgctggccg    1680
cgtctttaaa gacagcgaca aattcgatgc aaatgattct atcctaaaag accaaacaca    1740
agaatggtca ggttcagcca catttacatc tgacggaaaa atccgtttat tctcactga    1800
tttctccggt aaacattacg gcaaacaaac actgacaact gcacaagtta acgtatcagc    1860
```

```
atcagacagc tctttgaaca tcaacggtgt agaggattat aaatcaatct tgacggtga    1920
cggaaaaacg tatcaaaatg tacagcagtt catcgatgaa ggcaactaca gctcaggcga   1980
caaccatacg ctgagagatc ctcactacgt agaagataaa ggccacaaat acttagtatt   2040
tgaagcaaac actggaactg aagatggcta ccaaggcgaa gaatctttat ttaacaaagc   2100
atactatggc aaaagcacat cattcttccg tcaagaaagt caaaaacttc tgcaaagcga   2160
taaaaaacgc acggctgagt tagcaaacgg cgctctcggt atgattgagc taaacgatga   2220
ttacacactg aaaaaagtga tgaaaccgct gattgcatct aacacagtaa cagatgaaat   2280
tgaacgcgcg aacgtcttta aaatgaacgg caaatggtac ctgttcactg actcccgcgg   2340
atcaaaaatg acgattgacg gcattacgtc taacgatatt tacatgcttg ttatgtttc    2400
taattcttta actggcccat acaagccgct gaacaaaact ggccttgtgt aaaaatgga    2460
tcttgatcct aacgatgtaa cctttactta ctcacacttc gctgtacctc aagcgaaagg   2520
aaacaatgtc gtgattacaa gctatatgac aaacagagga ttctacgcag acaaacaatc   2580
aacgtttgcg cctagcttcc tgctgaacat caaaggcaag aaaacatctg ttgtcaaaga   2640
cagcatcctt gaacaaggac aattaacagt taacaaataa aaacgcaaaa gaaaatgccg   2700
atatcctatt ggcattgacg tcaggtggca cttttcggta ccaaggtgga gatcaaacga   2760
actgtggctg caccatctgt cttcatcttc ccgccatctg attcacagtt gaaatctgga   2820
actgcctctg ttgtgtgcct gctgaataac ttctatccca gagaggccaa agtacagtgg   2880
aaggtggata cgccctccaa atcgggtaac tcccaggaga gtgtcacaga gcaggacagc   2940
aaggacagca cctacagcct cagcagcacc ctgacgctga gcaaagcaga ctacgaaaaa   3000
cataaagtct acgcctgcga agtcacccat cagggcctga gctcgcccgt cacaaagagc   3060
ttcaacaggg gagagtgtta gagacaaagg tcctgagagc tagctggcca gacatgataa   3120
gatacattga tgagtttgga caaccacaa ctagaatgca gtgaaaaaaa tgctttattt    3180
gtgaaatttg tgatgctatt gctttatttg taaccattat aagctgcaat aaacaagtta   3240
acaacaacaa ttgcattcat tttatgtttc aggttcaggg ggaggtgtgg gaggttttt    3300
aaagcaagta aaacctctac aaatgtggta tggaattaat tctaaaatac agcatagcaa   3360
aactttaacc tccaaatcaa gcctctactt gaatcctttt ctgagggatg aataaggcat   3420
aggcatcagg ggctgttgcc aatgtgcatt agctgtttgc agcctcacct tctttcatgg   3480
agtttaagat atagtgtatt ttcccaaggt ttgaactagc tcttcatttc tttatgtttt   3540
aaatgcactg acctcccaca ttcccttttt agtaaaatat tcagaaataa tttaaataca   3600
tcattgcaat gaaaataaat gttttttatt aggcagaatc cagatgctca aggcccttca   3660
taatatcccc cagtttagta gttggactta gggaacaaag gaacctttaa tagaaattgg   3720
acagcaagaa agcgagcttc tagctttagt tcctggtgta cttgagggggg atgagttcct   3780
caatggtggt tttgaccagc ttgccattca tctcaatgag cacaaagcag tcaggagcat   3840
agtcagagat gagctctctg cacatgccac aggggctgac cacctgatg gatctgtcca    3900
cctcatcaga gtaggggtgc ctgacagcca caatggtgtc aaagtccttc tgcccgttgc    3960
tcacagcaga cccaatggca atggcttcag cacagacagt gaccctgcca atgtaggcct   4020
caatgtggac agcagagatg atctccccag tcttggtcct gatggccgcc ccgacatggt   4080
```

```
gcttgttgtc ctcatagagc atggtgatct tctcagtggc gacctccacc agctccagat    4140
cctgctgaga gatgttgaag gtcttcatga tggctcctcc tgtcaggaga ggaaagagaa    4200
gaaggttagt acaattgcta tagtgagttg tattatacta tgcttatgat taattgtcaa    4260
actagggctg cagggttcat agtgccactt ttcctgcact gccccatctc ctgcccaccc    4320
tttcccaggc atagacagtc agtgacttac caaactcaca ggagggagaa ggcagaagct    4380
tgagacagac ccgcgggacc gccgaactgc gaggggacgt ggctagggcg gcttctttta    4440
tggtgcgccg gccctcggag gcagggcgct cggggaggcc tagcggccaa tctgcggtgg    4500
caggaggcgg ggccgaaggc cgtgcctgac caatccggag cacataggag tctcagcccc    4560
ccgccccaaa gcaagggaa gtcacgcgcc tgtagcgcca gcgtgttgtg aaatggggc     4620 ttgggggggt tggggccctg actagtcaaa acaaactccc attgacgtca atggggtgga    4680
gacttggaaa tccccgtgag tcaaaccgct atccacgccc attgatgtac tgccaaaacc    4740
gcatcatcat ggtaatagcg atgactaata cgtagatgta ctgccaagta ggaaagtccc    4800
ataaggtcat gtactgggca taatgccagg cgggccattt accgtcattg acgtcaatag    4860
ggggcgtact tggcatatga tacacttgat gtactgccaa gtgggcagtt taccgtaaat    4920
actccaccca ttgacgtcaa tggaaagtcc ctattggcgt tactatggga acatacgtca    4980
ttattgacgt caatgggcgg gggtcgttgg gcggtcagcc aggcgggcca tttaccgtaa    5040
gttatgtaac gcctgcaggt taattaagaa catgtgagca aaaggccagc aaaaggccag    5100
gaaccgtaaa aaggccgcgt tgctggcgtt tttccatagg ctccgccccc ctgacgagca    5160
tcacaaaaat cgacgctcaa gtcagaggtg gcgaaacccg acaggactat aaagatacca    5220
ggcgtttccc cctggaagct ccctcgtgcg ctctcctgtt ccgaccctgc cgcttaccgg    5280
atacctgtcc gcctttctcc cttcgggaag cgtggcgctt tctcatagct cacgctgtag    5340
gtatctcagt tcggtgtagg tcgttcgctc caagctgggc tgtgtgcacg aacccccgt    5400 tcagcccgac cgctgcgcct tatccggtaa ctatcgtctt gagtccaacc cggtaagaca    5460
cgacttatcg ccactggcag cagccactgg taacaggatt agcagagcga ggtatgtagg    5520
cggtgctaca gagttcttga agtggtggcc taactacggc tacactagaa gaacagtatt    5580
tggtatctgc gctctgctga agccagttac cttcggaaaa agagttggta gctcttgatc    5640
cggcaaacaa accaccgctg gtagcggtgg tttttttgtt tgcaagcagc agattacgcg    5700
cagaaaaaaa ggatctcaag aagatccttt gatcttttct acggggtctg acgctcagtg    5760
gaacgaaaac tcacgttaag ggattttggt catggctagt taattaacat ttaaatcagc    5820
ggccgcaata aaatatcttt attttcatta catctgtgtg ttggttttt gtgtgaatcg    5880 taactaacat acgctctcca tcaaaacaaa acgaaacaaa acaaactagc aaaataggct    5940
gtccccagtg caagtgcagg tgccagaaca tttctctatc gaa                     5983
```

ANTI-FIBULIN-3 ANTIBODIES AND USES THEREOF

CROSS REFERENCE TO RELATED APPLICATION

This application is a 35 U.S.C. § 371 National Phase Entry of the International Application No. PCT/US2015/019639 filed Mar. 10, 2015, which designates the U.S. and which claims benefit under 35 U.S.C. § 119(e) of the U.S. provisional application No. 61/950,410, filed Mar. 10, 2014, the contents of each of which is incorporated herein by reference in its entirety.

GOVERNMENT SUPPORT

This invention was made with Government support under Grant No.: ROI-CA152065 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Mar. 6, 2015, is named 043214-079111-PCT_SL.txt and is 64,823 bytes in size.

FIELD OF THE DISCLOSURE

This disclosure relates to specific anti-fibulin-3 antibodies and the treatment of malignant cancers and other conditions mediated by fibulin-3 activity.

BACKGROUND OF THE DISCLOSURE

Around 45% of all primary brain tumors are gliomas. The survival rate from having gliomas is varied. Factors contributing to this range of success of treating gliomas include the types (grade) of gliomas and stage of the glioma. In addition, the position of the tumor in the brain and the symptoms caused by the tumor are also very important factors. For example, brain stem gliomas are particularly difficult to treat, whatever their grade. The brain stem is a very complicated and delicate part of the brain and completely removing the tumor is often near impossible. Furthermore, high doses of radiotherapy are not recommended either because this may cause too much damage to the normal brain stem. Sometimes, conventional chemotherapy is often the last remaining therapies for such inoperable tumor.

SUMMARY OF THE DISCLOSURE

Embodiments of the present disclosure are based on the development of specific antibodies that target a short sequence of 23 amino acids in fibulin-3. This short sequence has been shown to be involved in activating the Notch signaling pathway in cells. The binding of the specific anti-fibulin-3 antibodies to this short 23 amino acid sequence induces cytotoxicity and apoptosis of glioma cancer cells but not normal cells, as well as inhibits the invasiveness of cancer cells. Furthermore, the anti-fibulin-3 antibodies worked synergistically with known glioma chemotherapeutic, temozolomide, to enhance the cytotoxicity effect of temozolomide. Therefore, specific anti-fibulin-3 antibodies that target the short 23 amino acid sequence in fibulin-3 are useful for promoting cytotoxicity and apoptosis in cancer cells, for inhibiting the invasiveness of cancer cells, and for the treatment of malignant cancers and other conditions mediated by fibulin-3 activity and/or promoted by the Notch signaling pathway.

Accordingly, it is the objective of this disclosure to provide anti-fibulin-3 antibodies that target specifically a short sequence of 23 amino acids in fibulin-3; the short sequence in fibulin-3 that is involved in activating the Notch signaling in cells. Embodied herein also include chimeric anti-fibulin-3 antibodies, single chain anti-fibulin-3 antibodies, and recombinant proteins having the antigen-binding regions of an anti-fibulin-3 antibody, e.g., chimeric antigen receptors (CARs). CARs can be expressed in transfected host T cells.

It is also the objective of this disclosure to provide methods of treatment of malignant cancers and other conditions mediated by fibulin-3 activity.

In one embodiment, this disclosure provides an isolated antibody that binds to an amino acid sequence of SEQ ID NO: 1 or 2. SEQ ID NO: 1, TYTQCTDGYEWD-PVRQQCKDIDE, is the peptide fragment derived from fibulin-3 and SEQ ID NO: 2, TYTQCTDGYEWD-PVRQQCRDIDE, is a modified peptide fragment derived from fibulin-3.

In another embodiment, this disclosure provides a single chain antibody comprising the variable domains of the heavy and light chains of a monoclonal antibody that specifically binds to a peptide fragment of fibulin-3 consisting of the amino acid sequence of SEQ ID NO: 1 or 2.

In one embodiment, this disclosure provides an isolated antibody comprising any sequence disclosed in FIG. 13 or the SEQ ID NOS: 3-10. This isolated antibody specifically binds to a peptide fragment of fibulin-3 consisting of the amino acid sequence of SEQ ID NO: 1 or 2. In one embodiment, this disclosure provides an isolated antibody comprising SEQ ID NOS: 23 and/or 24.

In one embodiment, this disclosure provides a single chain antibody comprising the variable domains of the heavy and light chains of a monoclonal antibody comprising any sequence disclosed in FIG. 13 or the SEQ ID NOS: 3-10. In one embodiment, this disclosure provides a single chain antibody comprising the variable domains of the heavy and light chains of a monoclonal antibody having SEQ ID NOS: 3 and 4. This single chain antibody specifically binds to a peptide fragment of fibulin-3 consisting of the amino acid sequence of SEQ ID NO: 1 or 2. In one embodiment, this disclosure provides a single chain antibody comprising SEQ ID NO: 25 or 26.

In another embodiment, this disclosure provides a recombinant protein comprising the antigen-binding region of a monoclonal antibody that specifically binds to an amino acid sequence of SEQ ID NO: 1 or 2. In one embodiment, this disclosure provides a recombinant protein comprising the antigen-binding region of a monoclonal antibody having SEQ ID NOS: 3 and 4. In one embodiment, this recombinant protein comprising SEQ ID NOS: 3 and/or 4. In one embodiment, this recombinant protein comprising SEQ ID NOS: 23, or 24 or 25 or 26. In one embodiment, the recombinant protein is a CAR.

In one embodiment, this disclosure provides a recombinant protein comprising any sequence disclosed in FIG. 13 or the SEQ ID NOS: 3-10, or comprising SEQ ID NOS: 23, or 24 or 25 or 26. This recombinant protein specifically binds to a peptide fragment of fibulin-3 consisting of the amino acid sequence of SEQ ID NO: 1 or 2.

In another embodiment, this disclosure provides a heavy chain of a monoclonal antibody that binds to an amino acid sequence of SEQ ID NO: 1 or 2. In one embodiment, the heavy chain consist essentially of SEQ ID NO: 3. In one embodiment, the heavy chain consist essentially of SEQ ID NO: 24.

In another embodiment, this disclosure provides a light chain of a monoclonal antibody that binds to an amino acid sequence of SEQ ID NO: 1 or 2. In one embodiment, the light chain consist essentially of SEQ ID NO: 4. In one embodiment, the light chain consist essentially of SEQ ID NO: 23.

In one embodiment, this disclosure provides a heavy chain of a monoclonal antibody comprising any sequence disclosed in FIG. 13 or the SEQ ID NOS: 3, 5-7, and 24.

In one embodiment, this disclosure provides a light chain of a monoclonal antibody comprising any sequence disclosed in FIG. 13 or the SEQ ID NOS: 4, 8-10, and 23.

In one embodiment, this disclosure provides a hybridoma producing a monoclonal antibody that binds to an amino acid sequence of SEQ ID NO: 1 or 2.

In one embodiment, this disclosure provides a hybridoma producing a monoclonal antibody comprising any sequence disclosed in FIG. 13 or the SEQ ID NOS: 3-10, or 23-26.

In one embodiment, this disclosure provides a cell line that produces an antibody that binds to an amino acid sequence of SEQ ID NO: 1 or 2, or an antibody that comprises any sequence disclosed in FIG. 13 or the SEQ ID NOS: 3-10, or 23-26.

In one embodiment, this disclosure provides an expression vector which expresses an antibody that binds to an amino acid sequence of SEQ ID NO: 1 or 2, or an antibody that comprises any sequence disclosed in FIG. 13 or the SEQ ID NOS: 3-10, or 23-26. In one embodiment, the expression vector expresses the antibody in eukaryotic cells. In another embodiment, the expression vector expresses the antibody in prokaryotic cells.

In one embodiment, this disclosure provides an expression vector which expresses a recombinant protein comprising any sequence disclosed in FIG. 13 or the SEQ ID NOS: 3-10, or 23-26. In one embodiment, the expression vector expresses the antibody in eukaryotic cells. In another embodiment, the expression vector expresses the antibody in prokaryotic cells.

In one embodiment, this disclosure provides a kit comprising an isolated antibody described, a single chain antibody described, a recombinant protein described, a light chain of a monoclonal antibody described, a heavy chain of a monoclonal antibody described, and/or a hybridoma described herein.

In one embodiment, this disclosure provides a composition comprising an isolated antibody described, a single chain antibody described, a recombinant protein described, a CAR, a light chain of a monoclonal antibody described, a heavy chain of a monoclonal antibody described, and/or a hybridoma described herein.

In one embodiment, this disclosure provides a pharmaceutical composition comprising an isolated antibody described, a single chain antibody described, a recombinant protein described, a CAR, a light chain of a monoclonal antibody described, a heavy chain of a monoclonal antibody described and a pharmaceutically acceptable excipient.

In one embodiment, this disclosure provides a method of inducing cytotoxicity or apoptosis, or inhibiting cancer cells, or reducing the invasiveness of cancer cells comprising contacting a cancer cell with an effective amount of an isolated antibody described herein, or with a composition described, or with a pharmaceutical composition described. In some embodiments, the method of inducing cytotoxicity or apoptosis, or inhibiting cancer cells, or reducing the invasiveness of cancer cells comprises contacting with a recombinant protein, a CAR and/or a single chain antibody or a chimeric antibody described herein.

In one embodiment, this disclosure provides a method of treating a condition mediated by fibulin-3 activity in a subject, the method comprising administering to the subject a composition comprising an effective amount of an isolated antibody described herein, or with a composition described, or with a pharmaceutical composition described. In some embodiments, the method of treating a condition mediated by fibulin-3 activity in a subject comprises administering a recombinant protein, a CAR and/or a single chain antibody or a chimeric antibody described herein.

In one embodiment, this disclosure provides a method for inhibiting aberrant angiogenesis in a subject, the method comprising administering a composition comprising an effective amount of an isolated antibody described herein, or with a composition described, or with a pharmaceutical composition described to the subject. In some embodiments, the method for inhibiting aberrant angiogenesis in a subject comprises administering a recombinant protein, a CAR and/or a single chain antibody or a chimeric antibody described herein.

In one embodiment, this disclosure provides a method of treatment of malignant cancer in a subject comprising administering a composition comprising an effective amount of an isolated antibody described herein, or with a composition described, or with a pharmaceutical composition described to the subject. In some embodiments, the method of treatment of malignant cancer in a subject comprises administering a recombinant protein, a CAR and/or a single chain antibody or a chimeric antibody described herein.

In one embodiment, this disclosure provides a method of enhancing the effectiveness of a cancer therapy comprising administering a composition comprising an effective amount of an isolated antibody described herein or a pharmaceutical composition comprising an antibody described herein to the subject in conjunction with the cancer therapy or during the cancer therapy. The cancer therapy is one that is conventional or known in the art and is currently used in practice. The cancer therapy does not comprise a composition comprising an effective amount of an isolated antibody that binds to an amino acid sequence of SEQ ID NO: 1 or 2. In some embodiments, the method of enhancing the effectiveness of a cancer therapy comprises administering a recombinant protein, a CAR and/or a single chain antibody or a chimeric antibody described herein.

In one embodiment, this disclosure provides a method of treatment of malignant cancer in a subject comprising administering (a) a composition comprising an effective amount of an isolated antibody described herein or a pharmaceutical composition comprising an antibody herein and; (b) at least one additional cancer therapy to the subject. The cancer therapy is one that is conventional or known in the art and is currently used in practice. The cancer therapy does not comprise a composition comprising an effective amount of an isolated antibody that binds to an amino acid sequence of SEQ ID NO: 1 or 2. In some embodiments, the method of treatment of malignant cancer in a subject comprises administering a recombinant protein, a CAR and/or a single chain antibody or a chimeric antibody described herein.

In one aspect, this disclosure provides a use of a composition comprising an isolated antibody described, a recombinant protein described, a CAR described, a light chain of the antibody described, and/or a heavy chain of the antibody described for inhibiting cancer cells or for reducing the invasiveness of cancer cells or for enhancing the effectiveness of a cancer therapy. The cancer therapy is one that is conventional or known in the art and is currently used in practice. The cancer therapy does not comprise a composition comprising an effective amount of an isolated antibody binds to an amino acid sequence of SEQ ID NO: 1 or 2.

In other aspect, this disclosure provides a use of a composition comprising an isolated antibody described, a recombinant protein described, a CAR described, a light chain of the antibody described, and/or a heavy chain of the antibody described for treating a condition mediated by fibulin-3 activity in a subject.

In other aspect, this disclosure provides a use of a composition comprising an isolated antibody described, a single chain antibody described, a recombinant protein described, a CAR described, a light chain of the antibody described, and/or a heavy chain of the antibody described for inhibiting aberrant angiogenesis in a subject.

In other aspect, this disclosure provides a use of a composition comprising an isolated antibody described, a single chain antibody described, a recombinant protein described, a CAR described, a light chain of the antibody described, and/or a heavy chain of the antibody described for treatment of malignant cancer in a subject.

In other aspect, this disclosure provides a use of a composition comprising an isolated antibody described, a single chain antibody described, a recombinant protein described, a CAR described, a light chain of the antibody described, and/or a heavy chain of the antibody described for the manufacture of medicament for treating a condition mediated by fibulin-3 activity in a subject.

In other aspect, this disclosure provides a use of a composition comprising an isolated antibody described, a single chain antibody described, a recombinant protein described, a CAR described, a light chain of the antibody described, and/or a heavy chain of the antibody described for the manufacture of medicament for inhibiting aberrant angiogenesis in a subject.

In other aspect, this disclosure provides a use of a composition comprising an isolated antibody described, a single chain antibody described, a recombinant protein described, a CAR described, a light chain of the antibody described, and/or a heavy chain of the antibody described for the manufacture of medicament for treatment of malignant cancer in a subject.

In other aspect, this disclosure provides a use of a composition comprising an isolated antibody described, a single chain antibody described, a recombinant protein described, a CAR described, a light chain of the antibody described, and/or a heavy chain of the antibody described for the manufacture of an adjuvant a cancer therapy used in the treatment of malignant cancer in a subject.

In one embodiment of this aspect and all other aspects described herein, the antibody prevents or inhibits the activation of the Notch signaling pathway in cells.

In one embodiment of this aspect and all other aspects described herein, the antibody is a monoclonal antibody.

In one embodiment of this aspect and all other aspects described herein, the monoclonal antibody is a human monoclonal antibody, a mouse monoclonal antibody, or a humanized mouse monoclonal antibody.

In one embodiment of this aspect and all other aspects described herein, the antibody is a single chain antibody.

In one embodiment of this aspect and all other aspects described herein, the antibody is a single chain Fv (scFv) fragment.

In one embodiment of this aspect and all other aspects described herein, the antibody is a Fab fragment.

In one embodiment of this aspect and all other aspects described herein, the antibody is a humanized antibody.

In one embodiment of this aspect and all other aspects described herein, the antibody is a chimeric antibody.

In one embodiment of this aspect and all other aspects described herein, the antibody is produced by a hybridoma cell line.

In one embodiment of this aspect and all other aspects described herein, the antibody or recombinant protein comprises the amino acid sequence SEQ ID NO: 3 or 4 or 23, 24, 25 or 26.

In one embodiment of this aspect and all other aspects described herein, the antibody or recombinant protein comprises at least one of the amino acid sequences SEQ ID NO: 5-10 and 23-26.

In one embodiment of this aspect and all other aspects described herein, the antibody or recombinant protein is labeled with at least one agent. In one embodiment, the agent labels the antibody or recombinant protein. In another embodiment, the agent is a therapeutic agent.

In one embodiment of this aspect and all other aspects described herein, the agent include but is not limited to the group consisting of a radioisotope, a fluorescent compound, a bioluminescent compound, a chemiluminescent compound, a metal chelator, and an enzyme.

In one embodiment of this aspect and all other aspects described herein, the agent is a cytotoxic or a therapeutic agent.

In one embodiment of this aspect and all other aspects described herein, the cytotoxic agent includes but is not limited to the group consisting of ricin, ricin A-chain, doxorubicin, daunorubicin, taxol, ethidium bromide, mitomycin, etoposide, teniposide, vincristine, vinblastine, colchicine, dihydroxy anthracenedione, actinomycin, diphtheria toxin, *Pseudomonas* exotoxin (PE) A, PE40, abrin, abrin A chain, modeccin A chain, alpha-sarcin, gelonin, mitogellin, phenomycin, enomycin, curicin, calicheamicin, *Saponaria officinalis* inhibitor, and glucocorticoid.

In one embodiment of this aspect and all other aspects described herein, the radioisotope includes but is not limited to the group consisting of $^{212}$Bi, $^{131}$I, $^{131}$In, $^{90}$Y, and $^{186}$Re.

In one embodiment of this aspect and all other aspects described herein, the antibody fragment is an Fab', F(ab')$_2$, or Fv.

In one embodiment of this aspect and all other aspects described herein, the antibody is a human antibody or a humanized antibody. In other words, a portion of the antibody comprises human antibody sequences, for example, the constant regions of the heavy chain of a human antibody.

In one embodiment of this aspect and all other aspects described herein, the antibody comprises a combination of non-human antibody antigen-binding region residues and human antibody residues. In other words, the antibody or fragment thereof is a chimeric polypeptide comprising human antibody sequences and non-human antibody sequences.

In one embodiment of this aspect and all other aspects described herein, the antibody comprises the constant regions of a light chain and/or a heavy chain of a human antibody.

In one embodiment of this aspect and all other aspects described herein, the antibody comprises the variable regions of a light chain and a heavy chain of a non-human antibody that specifically binds to an amino acid sequence of SEQ ID NO: 1 or SEQ ID NO: 2.

In one embodiment of this aspect and all other aspects described herein, the antibody comprises the variable regions of a light chain and a heavy chain of a non-human antibody comprises any sequence disclosed in FIG. 13 or the SEQ ID NOS: 3-10.

In one embodiment of this aspect and all other aspects described herein, the contacting of cancer cells is in vitro, in vivo or ex vivo.

In one embodiment of this aspect and all other aspects described herein, the cancer cells contacted are glioma cells.

In one embodiment of this aspect and all other aspects described herein, the cancer cells are also contacted with at least one additional cancer therapeutic. The additional cancer therapeutic does not comprise a composition comprising an effective amount of an antibody or a fragment thereof that binds to an amino acid sequence of SEQ ID NO: 1 or 2.

In one embodiment of this aspect and all other aspects described herein, the condition mediated by aberrant fibulin-3 activity is selected from malignant cancer, spontaneous maculopathies, inherited macular degeneration syndromes, and pterygium such as conjuctival hyperplasia.

In one embodiment of this aspect and all other aspects described herein, spontaneous maculopathy includes but is not limited to choroid hypervascularization or macular degeneration in the eye.

In one embodiment of this aspect and all other aspects described herein, inherited macular degeneration syndrome includes but is not limited to Doyne's Honeycomb retinal dystrophy or Malattia Levantinese.

In one embodiment of this aspect and all other aspects described herein, the cancer is glioma. In one embodiment of this aspect and all other aspects described herein, the cancer is astrocytomas.

In one embodiment of this aspect and all other aspects described herein, the treatment method further comprises administering at least one additional cancer therapy. The additional cancer therapy does not comprise a composition comprising an effective amount of an antibody thereof that binds to an amino acid sequence of SEQ ID NO: 1 or 2.

In one embodiment of this aspect and all other aspects described herein, the composition and the at least one additional cancer therapy are administered simultaneously or sequentially to the subject.

In one embodiment of this aspect and all other aspects described herein, the at least one additional cancer therapy is chemotherapy or radiation.

In one embodiment of this aspect and all other aspects described herein, the chemotherapy includes but is not limited to the temozolomide, carmustine, bevacizumab, procarbazine, lomustine (CCNU) and vincristine.

In one embodiment of this aspect and all other aspects described herein, the composition or pharmaceutical composition is administered by injection, infusion, or instillation.

In one embodiment of this aspect and all other aspects described herein, the antibody comprised in the pharmaceutical composition is linked to a therapeutic agent.

In one embodiment of this aspect and all other aspects described herein, the treatment method further comprises selecting a subject for treatment.

In one embodiment of this aspect and all other aspects described herein, the treatment methods further selecting a subject having malignant cancer.

In one embodiment of this aspect and all other aspects described herein, the methods of treating a condition mediated by fibulin-3 activity in a subject further comprises selecting a subject having a condition mediated by fibulin-3 activity.

In one embodiment of this aspect and all other aspects described herein, the selected a subject a condition mediated by fibulin-3 activity exhibits at least one symptom of at least one of the condition selected from the group consisting of malignant cancer, spontaneous maculopathies, inherited macular degeneration syndromes, and pterygium.

In one embodiment of this aspect and all other aspects described herein, the methods of inhibiting aberrant angiogenesis in a subject further comprises selecting a subject having aberrant angiogenesis.

BRIEF DESCRIPTION OF THE DRAWINGS

FIGS. 1A and 1B show that fibulin-3 protein is highly expressed in glioma tissue and cells.

FIG. 1A shows the Western Blots that were probed for anti-fibulin-3 antibody (arrow). The Western Blots contained total homogenates from nine high-grade gliomas (two grade 3 astrocytomas and seven grade 3 glioblastomas) and seven age-matched controls which are normal brain cells. The asterisk represents nonspecific cross-reactivity of the commercial anti-fibulin-3 antibody used. Notice that fibulin-3 expression is virtually absent in normal brain compared with gliomas.

FIG. 1B demonstrates the expression of fibulin-3 in the conditioned medium of glioma cell lines (U87, U251, and U373), primary cultures of glioma xenografts (X12 and X14), and cultured normal human astrocytes (NHA). The Western Blots of these different conditioned media were probed for anti-fibulin-3 antibody (arrow). This figure is adapted from reference [9].

FIGS. 2A-2C show that fibulin-3 activates the Notch signaling pathway in glioma cancer cells.

FIG. 2A is a schematic cartoon representing the protein structure of fibulin-3, which contains a calcium-binding domain with homology to epidermal growth factor (EGF), five EGF-like domains, and one domain that is common to all fibulins. Two deleted versions of fibulin-3 were generated by PCR, one without the N-terminal domain (fib3Δn, 90-amino acid deletion) and one without the C-terminal domain (fib3Δc, 115-amino acid deletion).

FIG. 2B shows the degree of Notch signaling pathway activation by the full length fibulin-3, fib3Δn and fib3Δc. CNS 1 glioma cells expressing a Notch-reporter luminescent system were left untreated or transfected with plasmids carrying cDNA for full-length fibulin-3 (fib-3), fib3Δn, fib3Δc, or a blank control. The results show that full-length fibulin-3 or fib3Δc can activate the Notch reporter but fib3Δn fails to do so. (***, $p<0.001$ by one-way ANOVA).

FIG. 2C shows the Western blot analysis of the same cells in FIG. 2B showing the detection of the Notch Intracellular Domain (NICD), a fragment of Notch that is detected when Notch pathway is activated. The results show again that fib3Δn fails to activate Notch, indicating that the N-terminal domain of fibulin-3 contains the activating sequence. This figure is adapted from reference [13].

FIG. 3A shows a new deletion construct of fibulin-3 created by PCR to remove the sequence from Thr25 to Glu48 (23-amino acid deletion), which has high homology to the DSL motif that is found in Notch-activating proteins.

The construct was named fib3ΔDSL. FIG. 3A discloses SEQ ID NOS: 29 and 30, respectively, in order of appearance.

FIG. 3B shows that the deletion construct of fibulin-3, fib3ΔDSL, failed to activate the Notch signaling pathway. CNS1 glioma cells carrying a Notch reporter system were transfected with a control plasmid, or plasmids carrying fibulin-3 or fib3ΔDSL cDNA.

FIG. 3C shows that the same cells were analyzed by quantitative RT-PCR to measure the relative expression of genes upregulated by fibulin-3, such as MMP2 (which is Notch-independent) and Hes5 (Notch-dependent). Cells transfected with fib3ΔDSL showed much lesser increase of MMP2 compared to cells transfected with fibulin-3, and did not have increase in Hes5.

FIG. 4 discloses SEQ ID NOS 31-37, respectively, in order of appearance.

FIG. 5A shows the Western blotting of purified fibulin-3 (100 ng/lane), probed with sequential dilutions of anti-Fib3/911 and anti-Fib3/912. The preimmune sera did not recognize the protein.

FIG. 5B shows the specificity of anti-Fib3/911 and anti-Fib3/912 to detect fibulin-3 in cells that overexpress this protein. CNSI glioma cells were transfected with fibulin-3 cDNA (fib3-OE cells) or a control plasmid (control cells) and cultured for 24 h in serum-free conditions. Conditioned medium was collected and probed by Western blotting with anti-Fib3/911 (911), anti-Fib3/912 (912), or their respective preimmune sera (antibodies and sera were used at 1/5000 dilution). As a positive control the same samples were probed with a commercial anti-fibulin-3 antibody (mAb3-5, Santa Cruz Biotechnology, 1/400 dilution).

FIG. 5C shows the specificity of the antibody for the desired peptide sequence in fibulin-3. Purified fibulin-3 (100 ng/lane) was probed by Western blotting with anti-Fib3/911 (1/1000 dilution) in presence of increasing concentrations of a competing peptide (i.e., the peptide used for immunizations).

FIG. 11 shows the detection of fibulin-3 by mAb428.3C11.

FIG. 12 shows the kinetics of mAb428.3C11 binding to fibulin-3.

FIG. 13 shows the sequence of CDR regions of mAb428.3C11.

FIG. 19 shows the cloning strategy for generating semi-humanized mAb428.2.

FIG. 20 summarizes the cross-reactivity profile of mAb428.2 against normal healthy human tissues.

FIG. 23 demonstrates in vivo validation that mAb428.2 inhibits Notch and NFkB signaling via fibulin-3 when mAb428.2 is injected intratumorally. FIG. 23A shows the Western blotting with antibodies against molecules representative of the major pathways activated by fibulin-3 (i.e., Notch pathway and NF-kB pathway). FIG. 23B shows the graphed values of integrated optical density (IOD) for all bands normalized to tubulin levels.

FIGS. 26A-26C shows an embodiment of the generation of a single chain anti-fibulin 3 antibody (scFv428.2) and detection of the recombinant protein. FIG. 26A discloses SEQ ID NOS: 28 and 27, respectively, in order of appearance.

FIGS. 27A-27C demonstrate the specificity of scFv428.2 for fibulin-3 by and cytotoxic effect of scFv428.2 in vitro.

FIG. 28 shows the cDNA sequence (SEQ. ID. NO: 19) and protein sequence (SEQ. ID. NO: 23) of the light chain of the chimeric humanized, semi-humanized mAb428.2 that was subcloned into pFUSE-LIGHT plasmid for expression. General cloning data sheet for the pFUSE-LIGHT plasmid is shown in Table 4 and the cloning site is shown in FIG. 32.

FIG. 29 shows the cDNA sequence (SEQ. ID. NO: 20) and protein sequence (SEQ. ID. NO: 24) of the heavy chain of the chimeric humanized, semi-humanized mAb428.2 that was subcloned into pFUSE-HEAVY plasmid for expression. General cloning data sheet for the pFUSE-HEAVY plasmid is shown in Table 3 and the cloning site is shown in FIG. 33.

FIG. 30 shows the cDNA sequence (SEQ. ID. NO: 21) and protein sequence (SEQ. ID. NO: 25) of the single chain scFv428 that was optimized and designed for prokaryotic expression.

FIG. 31 shows the cDNA sequence (SEQ. ID. NO: 22) and protein sequence (SEQ. ID. NO: 26) of the single chain scFv428 that was optimized and designed for eukaryotic expression.

FIG. 32 shows the Afe 1/Sph 1 cloning site of the pFUSE-HEAVY plasmid. FIG. 32 includes the nucleic acid sequences (SEQ ID NOS: 44 and 45 in order of appearance), the cloning site Afe 1/Sph 1 and the coded protein sequences; the IL-2 signal and the human FAB, SEQ ID NOS: 38 and 39 in order of appearances. DNA sequence of the pFUSE-HEAVY plasmid is SEQ ID NO: 46.

FIG. 33 shows the Afe 1/Sph 1 cloning site of the pFUSE-LIGHT plasmid. FIG. 33 includes the nucleic acid sequences (SEQ ID NOS: 53 and 54 in order of appearances), the cloning site Afe 1/Sph 1 and the coded protein sequences; the IL-2 signal and the human FAB, SEQ ID NO: 55 and 48 in order of appearances. DNA sequence of the pFUSE-HEAVY plasmid is SEQ ID NO: 56.

DETAILED DESCRIPTION

Definitions

Figures 3A, 3B, 3C:
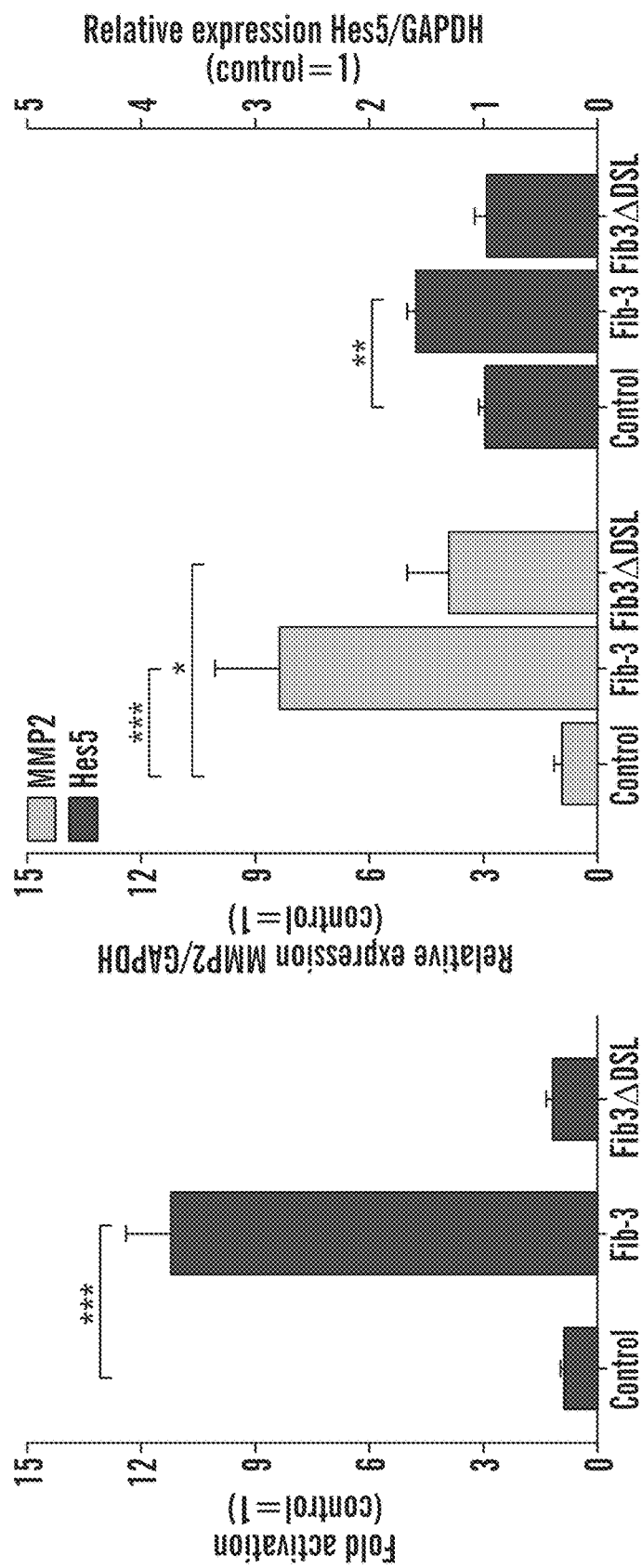
FIGS. 3A-3C show that an N-terminal sequence of fibulin-3 is required for Notch signaling pathway activation.

As used herein, the term "antibody" is used to mean immunoglobulin molecules and functional fragments thereof, regardless of the source or method of producing the fragment. As used herein, a "functional fragment" of an immunoglobulin is a portion of the immunoglobulin molecule that specifically binds to a binding target. Thus, the term "antibody" as used herein encompasses whole antibodies, such as antibodies with isotypes that include but are not limited to IgG, IgM, IgA, IgD, IgE and IgY, and even single-chain antibodies found in some animals e.g., camels, as well as fragments that specifically bind to target. Whole antibodies or fragments thereof may be monoclonal or polyclonal, and they may be humanized or chimeric. The term "monoclonal antibody" as used herein is not limited to antibodies produced through hybridoma technology. Rather, the term "monoclonal antibody" refers to an antibody that is derived from a single clone, including any eukaryotic, prokaryotic, or phage clone, and not the method by which it is produced. The term "antibody" also encompasses functional fragments of immunoglobulins, including but not limited to Fab fragments, Fab' fragments, F(ab')2 fragments and Fd fragments. "Antibody" also encompasses fragments of immunoglobulins that comprise at least a portion of a VL and/or VH domain, such as single chain antibodies, a single-chain Fv (scFv), disulfide-linked Fvs and the like.

As used herein, the term "isolated" is meant to describe a compound of interest (e.g., an antibody) that is in an environment different from that in which the compound naturally occurs. "Isolated" is meant to include compounds that are within samples that are substantially enriched for the compound of interest and/or in which the compound of interest is partially or substantially purified. "Isolated" as it relates to a polypeptide or nucleic acid molecule, is used to mean a polypeptide or nucleic acid molecule that has been removed from its native environment. For example, polypeptides that have been removed or purified from cells are considered isolated. In addition, recombinantly produced polypeptides molecules contained in host cells are considered isolated for the purposes of the present invention. Similarly, recombinant DNA molecules contained in a vector are considered isolated for the purposes of the present invention. Further examples of isolated DNA molecules include, but are not limited to, recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

As used herein, the term "substantially enriched" or "purified" when used in reference to a compound of interest refers to the compound being present in a sample in greater concentration than it is found in nature. That is, the term does not imply absolute purity. Nonetheless, a compound that is substantially enriched or purified in a sample is generally present, for example, as comprising at least 50% of the compound of interest. The sample can have anywhere from at least 50%, at least 60%, at least 70%, at least 80%, at least 90%, at least 99%, and all the percentages between 50% to 100% of the compound of interest.

As used herein, the term "humanized" immunoglobulin or "humanized" antibody refers to an immunoglobulin comprising a human framework, at least one complementarity determining regions (CDR) from a non-human antibody, and in which any constant region present is substantially identical to a human immunoglobulin constant region, i.e., at least about 85-90%, preferably at least 95% identical. Hence, all parts of a humanized immunoglobulin, except possibly the CDRs, are substantially identical to corresponding parts of one or more native human immunoglobulin sequences. For example, a humanized immunoglobulin would encompass a chimeric mouse variable region/human constant region antibody.

As used herein, the term "chimeric" antibody refers to an antibody whose heavy and light chains have been constructed, typically by genetic engineering, from immunoglobulin gene segments belonging to different species. For example, the variable (V) segments of the genes from a mouse monoclonal antibody can be joined to human constant (C) segments, such as gammal and/or gamma4. A typical therapeutic or diagnostic chimeric antibody is thus a hybrid protein comprising at least one V region (e.g., VH or VL) or the entire antigen-binding domain (i.e., VH and VL) from a mouse antibody and at least one C (effector) region (e.g., CH (CH1, CH2, CH3, or CH4) or CL or the entire C domain (i.e., CH and CL) from a human antibody, although other mammalian species can be used. In some embodiments, especially for use in the therapeutic methods of the antibodies should contain no CH2 domain.

As used herein, the term "fragments" of the antibodies include, for example, Fab, Fab', F(ab')2 and Fv. These fragments lack the Fc fragment of intact antibody, clear more rapidly from the circulation, and can have less non-specific tissue binding than an intact antibody (Wahl et al., J. Nucl. Med. 24:316-325 (1983)). These fragments are produced from intact antibodies using methods well known in the art, for example by proteolytic cleavage with enzymes such as papain (to produce Fab fragments) or pepsin (to produce F(ab')2 fragments).

The terms "antigen" is well understood in the art and refer to the portion of a macromolecule which is specifically recognized by a component of the immune system, e.g., an antibody or a T-cell antigen receptor. The term "antigen" includes any protein determinant capable of specific binding to an immunoglobulin. Antigenic determinants usually consist of chemically active surface groupings of molecules such as amino acids or sugar side chains and usually have specific three dimensional structural characteristics, as well as specific charge characteristics.

In one embodiment, the isolated antibodies of the present disclosure must bind an antigen comprising an amino acid sequence at least 80% identical to the amino acid sequence of SEQ ID NO:1 or 2. The terms "polypeptide" and "protein" are used interchangeably herein. And the terms "antigen" relate to the antibodies and the methods of use described herein. In other embodiments, the isolated antibodies of the present disclosure must bind an antigen comprising an amino acid sequence at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identical to the amino acid sequence of SEQ ID NO:1 or 2.

In specific embodiments, the antigen is a peptide of comprising an amino acid sequence at least 80%, 85%, 90%, 95%, 97%, 98%, 99% or 100% identical to the amino acid sequence of SEQ ID NO:1. In another specific embodiment, the antigen comprises an amino acid sequence at least 80% identical to the amino acid sequence of SEQ ID NO:2. In even more specific embodiments, the antigen is a peptide of comprising an amino acid sequence at least 80%, 85%, 90%, 95%, 97%, 98%, 99% or 100% identical to the amino acid sequence of SEQ ID NO:2.

As used herein, "identity" as it relates to amino acid sequence or polynucleotide sequences is a measure of the identity of nucleotide sequences or amino acid sequences compared to a reference nucleotide or amino acid sequence, usually a wild-type sequence. In general, the sequences are aligned so that the highest order match is obtained. "Identity" per se has an art-recognized meaning and can be calculated using published techniques. (See, e.g., Computational Molecular Biology, Lesk, A. M., ed., Oxford University Press, New York (1988); Biocomputing: Informatics And Genome Projects, Smith, D. W., ed., Academic Press, New York (1993); Computer Analysis of Sequence Data, Part I, Griffin, A. M., and Griffin, H. G., eds., Humana Press, New Jersey (1994); von Heinje, G., Sequence Analysis In Molecular Biology, Academic Press (1987); and Sequence Analysis Primer, Gribskov, M. and Devereux, J., eds., M Stockton Press, New York (1991)). While several methods exist to measure identity between two polynucleotide or polypeptide sequences, the term "identity" is well known in the art (Carillo, H. & Lipton, D., Siam J Applied Math 48:1073 (1988)). Methods commonly employed to determine identity or similarity between two sequences include, but are not limited to, those disclosed in Guide to Huge Computers, Martin J. Bishop, ed., Academic Press, San Diego (1994) and Carillo, H. & Lipton, D., Siam J Applied Math 48:1073 (1988). Computer programs may also contain methods and algorithms that calculate identity and similarity. Examples of computer program methods to determine identity and similarity between two sequences include, but are not limited to, GCS program package (Devereux, J., et al., Nucleic Acids Research 12(i):387 (1984)), BLASTP, BLASTN, FASTA (Atschul, S. F., et al., J Molec Biol 215:403 (1990)).

As used herein, the term "epitope" refers to a surface portion of an antigen capable of eliciting an immune response and also capable of binding specifically with the antibody produced to counter that response.

The term "functional variants" as used herein refers to the antibody or fragments thereof that have amino acids mutations in the protein and yet can still specifically bind to the antigen, here the antigen is a synthetic peptide consisting of 23-amino acid sequence SEQ ID NO:1 or 2.

As used herein, "chimeric antigen receptor" or "CAR" refers to an artificially constructed hybrid polypeptide comprising an antigen-binding domain (e.g. an antigen-binding portion of an antibody (e.g. a scFV)) linked to a cell signaling and/or cell activation domain. In some embodiments the cell-signaling domain can be a T-cell signaling domain. In some embodiments, the cell activation domain can be a T-cell activation domain. CARs have the ability to redirect the specificity and reactivity of T cells and other immune cells toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimerize with endogenous T-cell receptor (TCR) alpha and beta chains. Most commonly, the CAR's extracellular binding domain is composed of a single chain variable fragment (scFv) derived from fusing the variable heavy and light regions of a murine or humanized monoclonal antibody. Alternatively, scFvs may be used that are derived from Fabs (instead of from an antibody, e.g., obtained from Fab libraries), in various embodiments, this scFv is fused to a transmembrane domain and then to an intracellular signaling domain. "First-generation" CARs include those that solely provide CD3zeta signals upon antigen binding, "Second-generation" CARs include those that provide both costimulation (e.g. CD28 or CD 137) and activation (CD3Q. "Third-generation" CARs include those that provide multiple costimulation (e.g. CD28 and CD 137) and activation (CO3Q). In various embodiments, the CAR is selected to have high affinity or avidity for the antigen. Further discussion of CARs can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety. The chimeric antigen receptors (CARs) can be introduced into T cells, and other immune cells such as Natural Killer (NK) cells or Natural Killer T (NKT) cells permitting the transfected cells to recognize a desired antigen. This approach equips the transfected cells with an immune receptor that does not require recognition of the major histocompatibility complex (MHC), which tumors can modify to avoid immune recognition. Moreover, upon engagement of the antibody with the targeted cancer cells, the transfected cells (T cells, NK or NKT) get activated and their killing capabilities are enhanced.

In one embodiment, as used herein, the term "treat" or "treatment" refers to therapeutic treatment, wherein the object is to slow down (lessen) an undesired physiological change or disorder, such as reducing and ameliorating the symptoms associated with the disease or disorder. In another embodiment, the term "treat" or "treatment" refers to slowing the development or spread of cancer.

As used herein, the term "effective amount' or "therapeutically effective amount' refers to an amount that can inhibit cancer cell growth and proliferation and spread, and/or induce cytotoxicity or apoptosis in cancer cells, or inhibit and/or cure the disease or disorder. The therapeutically effective amount can also lessen or results in the disappearance of symptoms, or cause the disease to go into remission.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration.

As used herein, the terms "administering," refers to the placement of the isolated antibody of the present disclosure, and the compositions described herein into a subject by a method or route which results in at least partial localization of the agent at a desired site, the cancer cells or location of aberrant angiogenesis. The antibodies and the compositions described herein can be administered by any appropriate route which results in an effective treatment in the subject.

As used herein, the term "comprising" or "comprises" is used in reference to methods, and respective component(s) thereof, that are essential to the disclosure, yet open to the inclusion of unspecified elements, whether essential or not. The use of "comprising" indicates inclusion rather than limitation.

The term "vector" used herein refers to a nucleic acid sequence containing an origin of replication and which is designed for delivery to a host cell or transfer between different host cells. As used herein, a vector can be viral or non-viral. A vector can be a plasmid, cosmid, phagmid, virus, bacteriophage, bacterial artificial chromosome or yeast artificial chromosome. A vector can be a DNA or RNA vector. A vector can be either a self-replicating extrachromosomal vector or a vector which integrates into a host genome.

As used herein, the term "expression vector" or "vector for expression" refers to a vector that has the ability to express heterologous nucleic acid fragments in a cell. An expression vector can comprise additional elements, for example, the expression vector can have two replication systems, thus allowing it to be maintained in two organisms, for example in human cells for expression and in a prokaryotic host for cloning and amplification.

As used herein, the term "viral vector" refers to a nucleic acid vector construct that includes at least one element of viral origin and has the capacity to be packaged into a viral vector particle. The viral vector can contain the sequences disclosed herein or nucleic acid sequences in place of non-essential viral genes. The vector and/or particle can be utilized for the purpose of transferring nucleic acids into cells either in vitro or in vivo. Numerous forms of viral vectors are known in the art.

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present disclosure was performed using standard procedures known to one skilled in the art, for example, in Michael R. Green and Joseph Sambrook, Molecular Cloning: A Laboratory Manual, Cold Spring Harbor Laboratory Press, Cold Spring Harbor, N.Y., USA (2012); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al. ed., John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Meolcular Biology, Vo. 203, 2003, Transgenic Mouse, editored by Marten H. Hofker and Jan van Deursen, which are all herein incorporated by reference in their entireties.

It should be understood that this disclosure is not limited to the particular methodology, protocols, and reagents, etc., described herein and as such may vary. The terminology used herein is for the purpose of describing particular embodiments only, and is not intended to limit the scope of the present disclosure, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present disclosure. These publications are provided solely for their disclosure prior to the filing date of the present application. Nothing in this regard should be construed as an admission that the inventors are not entitled to antedate such disclosure by virtue of prior disclosure or for any other reason. All statements as to the date or representation as to the contents of these documents is based on the information available to the applicants and does not constitute any admission as to the correctness of the dates or contents of these documents.

The inventors demonstrated that (1) fibulin-3 is highly expressed in invasive or highly metastatic tumors compared to normal tissue; (2) increased levels of fibulin-3 promote growth and invasion in several tumor models; (3) fibulin-3 has a defined mechanism of action by activation of Notch signaling; and (4) suppression of fibulin-3 reduces tumor growth and sensitizes malignant cancer cells to death stimuli. Increased fibulin-3 expression is also found in a number of cancers and other diseases. For examples, in pancreas, cervical, ovarian, lung, nose, throat and bone cancers. See Table 1. Based in these results, the inventors decided to pursue the development of a novel antibody that could block fibulin-3 by specific inhibition of its molecular mechanism of action. In doing so, this blocking anti-fibulin-3 can be used as a therapeutic agent for the treatment of tumors, especially highly metastatic tumors.

The inventors selected a specific subclone (mAb428.2.3C11.H11.G3), hereafter named "mAb428.3C11" or "mAb428.2", for further testing and validation. The inventors demonstrated that mAb428.2 was able to recognize fibulin-3 in biochemical (Western blotting) and immunohistochemical procedures, and retained the original function-blocking ability sought for this antibody. The inventors also reported the sequences of the CDR regions of this antibody.

The inventors further tested mAb428.2 in vitro and in vivo. The mAb428.2 showed high affinity for fibulin-3 (Kd 5 nM) and no cross-reactivity against homologous fibulin-4 or -5. The antibody detected fibulin-3 in the stroma and capillaries of human GBM without cross-reactivity against normal brain. The mAb428.2 blocked fibulin-3-dependent Notch activation and caused significant GBM glioblastoma cell cytotoxicity, without effects on normal astrocytes. In vitro and in vivo studies indicate that mAb428.2 possess anti-tumor efficacy without toxicity. Direct intratumoral injection of mAb428.2 in a GBM glioblastoma stem cell model xenograft demonstrated Notch inhibition and caused 45% median volume reduction. Intravenous injection of mAb428.2 (8×30 mg/kg) in the same xenograft model caused significant delay in tumor growth and extended overall survival two-fold.

The inventors also generated of a single-chain variable fragment derived from mAb428.2 (named "scFv428.2") and analyzed its ability to detect fibulin-3 and induce cytotoxicity in glioblastoma cells. The culture media with scFv428.2 induce cytotoxicity in glioblastoma cells. See FIG. 27.

Accordingly, embodiments of the present disclosure are based on the development of specific antibodies that target a short sequence of 23 amino acids in fibulin-3. This short sequence of 23 amino acids in fibulin-3 is necessary and is involved in activating the Notch signaling pathway in cells. The binding of isolated antibodies to this short sequence of 23 amino acids in fibulin-3 induces cytotoxicity and apoptosis of glioma cancer cells but not normal cells, as well as inhibits the invasiveness of cancer cells. Furthermore, the anti-fibulin-3 antibodies worked synergistically with a known glioma chemotherapeutic, temozolomide, to enhance the cytotoxicity effect of temozolomide. Accordingly, the specific antibodies that target the short sequence of 23 amino acids in fibulin-3 are useful for promoting cytotoxicity and apoptosis in cancer cells, and for the treatment of malignant cancers and other conditions mediated by fibulin-3 activity.

This disclosure provides for novel biological reagents to be used singly for the treatment of malignant cancers or for adjuvant chemotherapy of malignant cancers. Specifically, provided herein is an isolated antibody directed against a newly identified "active site" of the extracellular protein fibulin-3, a 23-amino acid sequence that is highly conserved fibulin-3 found in several species.

The inventors generated and purified polyclonal antibodies against fibulin-3 by inoculation rabbits with a synthetic peptide consisting of 23-amino acid sequence SEQ ID NO:1 or 2. The antibodies have been validated to be specific against the fibulin-3 protein and have been shown to block fibulin-3 molecular function in vitro. In addition, the anti-fibulin-3 antibodies have been tested in cell culture and demonstrated significant cytotoxicity against brain cancer cells, both alone and also when combined with the chemotherapeutic drug temozolomide.

The inventors proceeded with the manufacture of monoclonal anti-fibulin-3 antibodies from these two polyclonal antibodies against fibulin-3, isolated and purified distinct monoclonal anti-fibulin-3 antibodies, validated the specific binding against the fibulin-3 protein and inhibition of fibulin-3 molecular function in vitro and against brain cancer cells.

Accordingly, this disclosure provides isolated anti-fibulin-3 antibodies that target a short sequence of 23 consecutive amino acids in fibulin-3 that is involved in activating the Notch signaling in cells. As used herein, the term "target" and "bind" are used interchangeable to indicate specific bind that is over and above that of background, non-specific binding in the absence of the short sequence.

In some embodiments, this disclosure provides compositions and methods of treatment of malignant cancers and other conditions mediated by fibulin-3 activity.

In one embodiment, this disclosure provides an isolated antibody that binds to a peptide sequence of fibulin-3 consisting of the amino acid sequence of SEQ ID NO: 1 or 2.

In one embodiment, this disclosure provides an isolated antibody that binds to an amino acid sequence of SEQ ID NO: 1 or 2.

In one embodiment, this disclosure provides an isolated antibody that binds to an amino acid sequence having at least 80% identity of SEQ ID NO: 1 or 2.

SEQ ID NO: 1 is TYTQCTDGYEWDPVRQQCKDIDE and SEQ ID NO: 2 is TYTQCTDGYEWDPVRQQCRDIDE.

In one embodiment, this isolated antibody is reactive, i.e., binds specifically, to the full-length fibulin-3 protein in an immune assay known in the art such as a Western Blot assay. This is because SEQ ID NO: 1 is encompassed within the full-length fibulin-3. In another embodiment, this isolated antibody is reactive to the peptide comprising of SEQ ID NO: 1 or 2, or to a peptide consisting of SEQ ID NO: 1 or 2. In another embodiment, this isolated antibody is reactive to the fusion chimeric polypeptide comprising of SEQ ID NO: 1 or 2. For example, fibulin-3 can be dot blotted on to a Western blot membrane or separated on a SDS-PAGE gel and then electro transferred on to a Western blot membrane. The Western blot membrane can then be tested with the isolated antibody described herein accord the standard Western blot technique known in the art. A positive signal on the blot at the position of fibulin-3 is located indicates specific reaction or reactivity of the isolated antibody or fragment against fibulin-3.

In one embodiment, this isolated antibody is reactive, i.e., binds specifically, to a peptide comprising the amino acid sequence of SEQ ID NO: 1 or 2 in an immune assay known in the art such as a Western Blot assay. The peptide fragment of fibulin-3 consisting of the amino acid sequence of SEQ ID NO: 1 or 2 is not a full-length fibulin-3. In one embodiment, the peptide fragment is a synthetic peptide comprising SEQ ID NO: 1 or 2 but is not a full-length fibulin-3.

In another embodiment, this disclosure provides a single chain antibody comprising the variable domains of the heavy and light chains of a monoclonal antibody that binds to an amino acid sequence of SEQ ID NO: 1 or 2. In another embodiment, the single chain antibody comprises at least one of SEQ ID NO: 3-10 or 25 or 26.

In another embodiment, this disclosure provides an isolated antibody comprising a heavy chain comprising SEQ ID NOs: 5, 6 and 7 and a light chain comprising SEQ ID NOs: 8, 9 and 10, wherein the antibody demonstrates a binding affinity for an amino acid sequence of SEQ ID NO: 1 or 2. In another embodiment, this disclosure provides an isolated antibody comprising SEQ ID NOS: 23 and/or 24.

In one embodiment of any one isolated antibody described herein, wherein the binding affinity for the amino acid sequence is at least $1 \times 10^{-7}$ M.

In one embodiment of any one isolated antibody described herein, wherein the binding affinity for the amino acid sequence is of less than or equal to $1 \times 10^{-7}$ M.

The specificity of the antibodies used in present disclosure may also be described or specified in terms their binding affinity towards the antigen (epitope) or of by their cross-reactivity. Specific examples of binding affinities encompassed in the present invention include but are not limited to those with a dissociation constant (Kd) less than $5 \times 10^{-2}$ M, $1 \times 10^{-2}$ M, $5 \times 10^{-3}$ M, $1 \times 10^{-3}$ M, $5 \times 10^{-4}$ M, $1 \times 10^{-4}$ M, $5 \times 10^{-5}$ M, $1 \times 10^{-5}$ M, $5 \times 10^{-6}$ M, $1 \times 10^{-6}$ M, $5 \times 10^{-7}$ M, $1 \times 10^{-7}$ M, $5 \times 10^{-8}$ M, $1 \times 10^{-8}$ M, $5 \times 10^{-9}$ M, $1 \times 10^{-9}$ M, $5 \times 10^{-10}$ M, $1 \times 10^{-10}$ M, $5 \times 10^{-11}$ M, $1 \times 10^{-11}$ M, $5 \times 10^{-12}$ M, $1 \times 10^{-12}$ M, $5 \times 10^{-13}$ M, $1 \times 10^{-13}$ M, $5 \times 10^{-14}$ M, $1 \times 10^{-14}$ M, $5 \times 10^{-15}$ M, or $1 \times 10^{-15}$ M.

In one embodiment of any one isolated antibody described herein, wherein the heavy chain comprises an amino acid sequence set forth in SEQ ID NO: 3 and the light chain comprises an amino acid sequence set forth in SEQ ID NO: 4. In one embodiment of any one isolated antibody described herein, wherein the heavy chain comprises an amino acid sequence set forth in SEQ ID NO: 24 and the light chain comprises an amino acid sequence set forth in SEQ ID NO: 23.

In another embodiment, this disclosure provides a recombinant protein comprising the antigen-binding region of a monoclonal antibody that specifically binds to an amino acid sequence of SEQ ID NO: 1 or 2. In another embodiment, the recombinant protein comprises at least one of SEQ ID NO: 3-10. The amino acid sequence of SEQ ID NO: 1 or 2 is derived from a peptide fragment of the human fibulin-3.

In one embodiment, the recombinant protein comprising the antigen-binding region of a monoclonal antibody that specifically binds to an amino acid sequence of SEQ ID NO: 1 or 2 is a chimeric antigen receptor (CAR). In one embodiment, the CAR comprises one or more sequences selected from the group consisting of SEQ ID NOS: 3-10, 23, 24, 25 and 26.

In another embodiment, this disclosure provides a heavy chain of a monoclonal antibody that specifically binds to a peptide fragment of fibulin-3 consisting of the amino acid sequence of SEQ ID NO: 1 or 2. In another embodiment, the heavy chain of a monoclonal antibody comprises at least one of SEQ ID NO: 3, 5-7.

In another embodiment, this disclosure provides a light chain of a monoclonal antibody that binds to an amino acid sequence of SEQ ID NO: 1 or 2. In another embodiment, the light chain of a monoclonal antibody comprises at least one of SEQ ID NO: 4, 8-10.

In one embodiment, this disclosure provides a hybridoma cell producing a monoclonal antibody that specifically binds to an amino acid sequence of SEQ ID NO: 1 or 2. In another embodiment, the monoclonal antibody produced by the hybridoma comprises at least one of SEQ ID NO: 3-10, and 23-26.

In one embodiment, this disclosure provides a cell line that produces an antibody that binds to an amino acid sequence of SEQ ID NO: 1 or 2, or an antibody that comprises any sequence disclosed in FIG. 13 or the SEQ ID NOS: 3-10 and 23-26.

Hybridomas are known in the art. In one embodiment, a hybridoma is a cell that is produced from the fusion of an antibody-producing lymphocyte and a non-antibody-producing cancer cell, such as a myeloma or lymphoma. The hybridoma thus formed then proliferates. The hybridoma and it progeny produce a continuous supply of a specific monoclonal antibody.

In one embodiment, this disclosure includes nucleic acids encoding the antibodies described herein. The nucleic acid molecules of this disclosure can be in the form of RNA, such as but not limited to mRNA, or in the form of DNA, including, for instance, cDNA and genomic DNA obtained by cloning or produced synthetically. The DNA may be, but is not limited to, double-stranded or single-stranded. Single-stranded DNA or RNA may be the coding strand, also known as the sense strand, or it may be the non-coding strand, also referred to as the anti-sense strand.

In one embodiment, the nucleic acids include nucleic acids that encode the recombinant protein that specifically binds to an amino acid sequence of SEQ ID NO: 1 or 2.

In one embodiment, the recombinant protein is a fusion or chimeric protein.

Using the information provided herein, a nucleic acid molecule of encoding an antibody or recombinant protein that specifically binds to an amino acid sequence of SEQ ID NO: 1 or 2 can be obtained using standard cloning and screening procedures, such as those for cloning cDNAs using mRNA as starting material.

In some embodiments, the nucleic acid molecules can include, but are not limited to those encoding the amino acid sequence of the polypeptide, by itself; the coding sequence for the polypeptide and additional sequences, such as those encoding a leader or secretory sequence, such as a pre-, or pro- or prepro-protein sequence; the coding sequence of the polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, e.g., ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide (SEQ ID NO: 27), such as the tag provided in a pQE vector (Qiagen, Inc.), among others, many of which are commercially available. As described in Gentz et al., Proc. Natl. Acad. Sci. USA 86:821-824 (1989), for instance, hexa-histidine (SEQ ID NO: 27) provides for convenient purification of the fusion protein. The "HA" tag is another peptide useful for purification which corresponds to an epitope derived from the influenza hemagglutinin protein, which has been described by Wilson et al., Cell 37:767 (1984).

In some embodiments, the nucleic acid molecules can include, but are not limited to those encoding the amino acid sequence of the polypeptide, comprises at least one of the nucleic acid sequences in FIG. 13 or SEQ ID NOS: 11-22.

In one embodiment of any one of the recombinant protein, the recombinant protein is a fusion protein. In one embodiment, the fusion protein comprises a heterologous region from immunoglobulin that is useful to solubilize proteins. For example, fusion proteins comprising various portions of constant region of immunoglobin molecules together with another human protein or part thereof are well known in the art. In many cases, the Fc portion of the fusion protein is thoroughly advantageous for use in therapy and diagnosis and thus results, for example, in improved pharmacokinetic properties. On the other hand, for some uses it would be desirable to be able to delete the Fc part after the fusion protein has been expressed, detected and purified in the advantageous manner described. This is the case when Fc portion proves to be a hindrance to use in therapy and diagnosis, for example when the fusion protein is to be used as antigen for immunizations. In drug discovery, for example, human proteins, such as, hIL-5-receptor has been fused with Fc portions for the purpose of high-throughput screening assays to identify antagonists of hIL-5. See, D. Bennett et al., Journal of Molecular Recognition, Vol. 8:52-58 (1995) and K. Johanson et al., The Journal of Biological Chemistry, Vol. 270, No. 16:9459-9471 (1995).

In one embodiment, the disclosure relates to variants of the nucleic acid molecules which encode portions, analogs or derivatives of the antibodies or recombinant proteins described herein. Variants may occur naturally, such as a natural allelic variant. By an "allelic variant" is intended one of several alternate forms of a gene occupying a given locus on a chromosome of an organism.

Non-naturally occurring variants may be produced using art-known mutagenesis techniques, which include, but are not limited to: oligonucleotide mediated mutagenesis, alanine scanning, PCR mutagenesis, site-directed mutagenesis (see, e.g., Carter et al., Nucl. Acids Res. 13:4331 (1986); and Zoller et al., Nucl. Acids Res. 10:6487 (1982)), cassette mutagenesis (see, e.g., Wells et al., Gene 34:315 (1985)), restriction selection mutagenesis (see, e.g., Wells et al., Philos. Trans. R. Soc. London Ser. A 317:415 (1986)).

Such variants include those produced by nucleotide substitutions, deletions or additions which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the antibodies. Also especially preferred in this regard are conservative substitutions.

In one embodiment, the disclosure also relates to vectors which include the isolated DNA molecules described herein, host cells which are genetically engineered with the recombinant vectors, and the production of antibodies or fragments thereof or recombinant proteins by recombinant techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, trp and tac promoters, the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

In one embodiment, this disclosure provides an expression vector which expresses an antibody that binds to an amino acid sequence of SEQ ID NO: 1 or 2, or an antibody that comprises any sequence disclosed in FIG. 13 or the SEQ ID NOS: 3-10, or 23-26. In one embodiment, the expression vector expresses the antibody in eukaryotic cells. In another embodiment, the expression vector expresses the antibody in prokaryotic cells.

In one embodiment, this disclosure provides an expression vector which expresses a recombinant protein comprising any sequence disclosed in FIG. 13 or the SEQ ID NOS: 3-10, or 23-26. In one embodiment, the expression vector expresses the antibody in eukaryotic cells. In another embodiment, the expression vector expresses the antibody in prokaryotic cells.

Examples of expression vectors for expressing an antibody that binds to an amino acid sequence of SEQ ID NO: 1 or 2, or an antibody that comprises any sequence disclosed in FIG. 13 or the SEQ ID NOS: 3-10, or 23-26 includes the pFUSE-HEAVY and the pFUSE-LIGHT plasmids shown in Table 3 and 4 respectively. The sequences of the pFUSE-HEAVY and the pFUSE-LIGHT plasmids shown in SEQ ID NOS: 46 and 56 respectively.

In one embodiment, the expression vector comprises at least one of SEQ. ID NOS: 19-22.

In one embodiment, this disclosure provides a kit comprising an isolated antibody or fragment thereof described, a single chain antibody described, a recombinant protein described, a light chain of a monoclonal antibody described, a heavy chain of a monoclonal antibody described and/or a hybridoma described herein.

In one embodiment, the disclosure also relates to administering the nucleic acids described herein or vectors comprising the nucleic acids to a subject for the treatment purposes, such as treating a condition mediated by fibulin-3 activity, for inhibiting aberrant angiogenesis, and for treating malignant cancer in the subject. The nucleic acids described herein or vectors comprising the nucleic acids would comprise at the minimum at least one of the nucleic acid sequences in FIG. 13 or SEQ ID NOS: 11-22.

In one embodiment, the disclosure also relates to administering the nucleic acids described herein or vectors comprising the nucleic acids to a subject for the treatment purposes, such as treating a condition mediated by fibulin-3 activity, for inhibiting aberrant angiogenesis, and for treating malignant cancer in the subject.

In one embodiment, provided herein is a method of treating a condition mediated by fibulin-3 activity, for inhibiting aberrant angiogenesis, and for treating malignant cancer in the subject, the method comprising administering an effective amount of the nucleic acids described herein or vectors comprising the nucleic acids described herein.

In one embodiment, the disclosure also relates to contacting the nucleic acids described herein or vectors comprising the nucleic acids with cancer cells for inducing cytotoxicity or apoptosis, inhibiting cancer cells, and/or reducing the invasiveness of the cancer cells.

In one embodiment, provided herein is a method of inducing cytotoxicity or apoptosis, inhibiting cancer cells, and/or reducing the invasiveness of the cancer cells, the met hod comprising contacting an effective amount of the nucleic acids described herein or vectors comprising the nucleic acids described herein with the cancer cells.

In one embodiment of the method described, the nucleic acids described herein or vectors comprising the nucleic acids would comprise at the minimum at least one of the nucleic acid sequences in FIG. 13 or SEQ ID NOS: 11-22. The vector is an artificially constructed vector or construct for expression of the nucleic acid in vivo in the subject or cancer cells. That is, the vector is design to express an antibody or a recombinant protein that binds to an amino acid sequence SEQ ID NO: 1 or 2, and the expressed antibody or recombinant protein have at least at least one amino acid sequence in FIG. 13 or SEQ ID NOS: 3-10, 23-26.

In some embodiment, the vector or construct for in vivo expression is a virus. For example, a lentivirus or adenovirus or retrovirus. Viral expression vectors include, but are not limited to reteroviruses, lentiviruses, Epstein Barr virus-, bovine papilloma virus, adenovirus- and adeno-associated-based vectors or hybrid virus of any of the above. In one embodiment, the vector is episomal. The use of a suitable episomal vector provides a means of maintaining the antagonist nucleic acid molecule in the subject in high copy number extra chromosomal DNA thereby eliminating potential effects of chromosomal integration.

In one embodiment, the expression vector can be a virus such as an adenovirus, an adeno-associated virus, or lentivirus, for example, MDH.xdna murine retroviral vector. Viral vectors provide an additional advantage of ease of transducing the HSPCs by viral infection. In another embodiment, the expression vector is a non-viral vector. Such vectors can be transfected into HSPCs using known transfection methods known in the art, such as cationic lipid transfection as disclosed herein.

In one embodiment, this disclosure provides a composition comprising an isolated antibody or fragment thereof described, a single chain antibody described, a recombinant protein described, a light chain of a monoclonal antibody described, a heavy chain of a monoclonal antibody described and/or a hybridoma described herein.

In one embodiment, this disclosure provides a pharmaceutical composition comprising an isolated antibody or fragment thereof described, a single chain antibody described, a recombinant protein described, a light chain of a monoclonal antibody described, a heavy chain of a monoclonal antibody described and a pharmaceutically acceptable excipient.

As used herein, in one embodiment, the phrase "binds to an amino acid sequence of SEQ ID NO: 1 or 2" refers to specific immune reactivity of the antibody or a recombinant protein to a peptide that at least have the amino acid sequence of SEQ ID NO: 1 or 2 as evaluated or tested in an immune assay known in the art or described herein. In one embodiment, the peptide having SEQ ID NO: 1 or 2 is not the full-length fibulin-3 polypeptide. Any conventional immune assay can be used to analyze and evaluate monoclonal antibodies during the production of the antibodies. For example, enzyme-linked immunosorbent assay (ELISA). In one embodiment, SEQ ID NOS 1 and 2 are contained at least one epitope of the anti-fibulin-3 antibody described herein.

Fibulins are proteins secreted by several cell types and accumulate in the extracellular space of tissues, where they contribute to forming the tissue scaffold known as extracellular matrix (1). The fibulin family is formed by seven members. Of these, fibulin-3, -4, and -5 form a subgroup of "small fibulins" that are highly homologous. These fibulins have been detected in several solid tumors and their role as pro-tumor agents has been established by the inventors. This is in part due to the fact that their molecular mechanisms are unknown or poorly understood (2, 3).

Fibulin-3 binds EGFR, the EGF receptor, induces EGFR autophosphorylation and the activation of downstream signaling pathways. Fibulin-3 also contributes to activation of the Notch signaling pathway. Fibulin-3 binds and inhibits the protease inhibitor TIMP3 and the Notch inhibitor DLL3; both molecular interactions contribute to the activation of the Notch signaling pathway.

Fibulin-3 is absent from epithelial tissues and localizes predominantly in some types of connective tissue and smooth muscle (4). Deletion of the fibulin-3 gene in mice causes symptoms similar to Marfan Syndrome, including early aging, loss of skin elasticity and multiple hernias of soft tissues (4, 5). On the other hand, pathological increase of fibulin-3 is a known factor associated with vascular proliferation in the retina, contributing to diseases such as Doyne's honeycomb retinal dystrophy and age-related macular degeneration, which are major causes of blindness in the elderly (6, 7).

The content of fibulin-3 is reduced in several types of solid tumors compared to their normal tissues and the protein was originally, and erroneously, proposed to have an anti-tumor role [8]. However, fibulin-3 had never been investigated in late-stage metastatic cancers nor in the highly invasive cancers of the brain (known as gliomas) before the original study published by the inventors in 2009. The inventors demonstrated that fibulin-3 was very highly expressed in gliomas compared to normal brain (FIG. 1) and proved that fibulin-3 promoted tumor invasion, therefore being a pro-tumor factor (9). Subsequent studies by other groups revised the expression of fibulin-3 in solid tumors and demonstrated that this protein was not increased in the initial stages (adenoma) but correlated instead with the advanced, metastatic stage, as shown with mesothelioma (10), pancreatic adenocarcinoma (11), ovarian and cervical cancer (12), lung cancers, and nose and throat cancers.

Further studies by the inventors demonstrated the molecular and cellular mechanisms of fibulin-3 in brain cancer (13). Specifically, these studies demonstrated that fibulin-3 activated the Notch signaling pathway, a signaling mechanism that is highly active in tumor cells and necessary for tumor cell survival. Analyses in culture and in animals implanted with gliomas lacking fibulin-3 demonstrated that this protein was necessary for tumor growth and that fibulin-3 suppression was sufficient to reduce Notch signaling in the tumors and decrease tumor development. In addition, the inventors demonstrated an excellent correlation between levels of fibulin-3 and activation of Notch mechanisms in human gliomas, suggesting that fibulin-3 may be a possible biomarker of Notch activity in the tumor.

The fibulin-3 is the gene product of the EFEMP1 gene. The alias for this gene product is EGF Containing Fibulin-Like Extracellular Matrix Protein, FBNL, DRAD, DHRD, MLVT, MTLV, Extracellular Protein S1-5, S1-5, FBLN3, fibulin-3, FIBL-3, fibrillin-like, and fibrillin-like protein. Massager RNA sequences in GENBANK™ NM_001039349.2 and NM_001039348.2.

In one embodiment of this aspect and all other aspects described herein, the antibody or fragment thereof prevents or inhibits the activation of the Notch signaling pathway in cells. In other words, this isolated antibody or fragment thereof blocks the Notch signaling pathway in cells when the cells are contacted with the antibody or fragment described. Any method known in the art can be used to assay and assess this blocking activity, for example, using the glioma cells expressing a Notch-reporter luminescent system as taught and described herein in the Examples section.

In one embodiment of this aspect and all other aspects described herein, the isolated anti-fibulin-3 antibody is a monoclonal antibody. In one embodiment of this aspect and all other aspects described herein, the monoclonal anti-fibulin-3 antibody is a human monoclonal antibody, a mouse monoclonal antibody, or a humanized mouse monoclonal antibody.

In one embodiment of this aspect and all other aspects described herein, the isolated antibody is a single chain antibody.

In one embodiment of this aspect and all other aspects described herein, the isolated antibody is a single chain Fv (scFv) fragment.

In one embodiment of this aspect and all other aspects described herein, the isolated antibody is a Fab fragment.

In one embodiment of this aspect and all other aspects described herein, the isolated antibody is produced by a hybridoma cell line.

In one embodiment of this aspect and all other aspects described herein, the isolated antibody comprises the amino acid sequence SEQ ID NO: 3 and/or 4. In other embodiments, the isolated antibody comprises the amino acid sequence SEQ ID NO: 23 and 24, or 25 or 26.

In one embodiment of this aspect and all other aspects described herein, the isolated antibody comprises at least one of the amino acid sequences SEQ ID NO: 5-10. In one embodiment of this aspect and all other aspects described herein, the isolated antibody comprises one or more of the amino acid sequences selected from the group of SEQ ID NO: 5-10.

In one embodiment of this aspect and all other aspects described herein, the isolated anti-fibulin-3 antibody is a chimeric antibody.

In one embodiment of this aspect and all other aspects described herein, the isolated anti-fibulin-3 antibody consists essentially of at least one of SEQ ID NOS: 3, 4, 23-26.

In another embodiment of this aspect and all other aspects described herein, the isolated anti-fibulin-3 antibodies include, but are not limited to multispecific, human, single chain antibodies, Fab fragments, F(ab)'2 fragments, fragments produced by a Fab expression library, domain-deleted antibodies (including, e.g., CH2 domain-deleted antibodies), anti-idiotypic (anti-Id) antibodies (including, e.g., anti-Id antibodies to antibodies of the invention), and epitope-binding fragments of any of the above. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule.

In one embodiment of any aspect described herein, the isolated anti-fibulin-3 antibodies also include, but are not limited to, engineered forms of antibodies and antibody fragments such as diabodies, triabodies, tetrabodies, and higher multimers of scFvs, single-domain antibodies, as well as minibodies, such as two scFv fragments joined by two constant (C) domains. See, e.g., Hudson, P. J. and Couriau, C., Nature Med. 9: 129-134 (2003); U.S. Publication No. 20030148409; U.S. Pat. No. 5,837,242 and these are incorporated hereby reference in their entirety.

In one embodiment of this aspect and all other aspects described herein, the antibody is a human antibody or a humanized antibody.

In one embodiment of this aspect and all other aspects described herein, the human antibody or a humanized antibody comprises SEQ ID NO 23 and/or 24.

In one embodiment of this aspect and all other aspects described herein, the antibody comprises non-human antibody antigen-binding region residues and human antibody residues.

In one embodiment of this aspect and all other aspects described herein, the antibody comprises the constant regions of a light chain and a heavy chain of a human antibody.

In one embodiment of this aspect and all other aspects described herein, the antibody comprises the variable regions of a light chain and a heavy chain of a non-human antibody that binds to an amino acid sequence of SEQ ID NO: 1 or SEQ ID NO: 2.

As used herein, in some embodiments, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, for example in, U.S. Pat. No. 5,939,598 by Kucherlapati et al, and this is incorporated hereby reference in its entirety.

In one embodiment, for example, for use in humans, the anti-fibulin-3 antibodies are human or humanized antigen-binding antibody fragments and include, but are not limited to, Fab, Fab and F(ab)'2, Fd, single-chain Fvs (scFv), single-domain antibodies, triabodies, tetrabodies, minibodies, domain-deleted antibodies, single-chain antibodies, disulfide-linked Fvs (sdFv) and fragments comprising either a variable light chain (VL) or variable heavy chain VH region. Antigen-binding antibody fragments, including single-chain antibodies, can comprise the variable region(s) alone or in combination with the entirety or a portion of the following: hinge region, CH1, CH2, and CH3 domains. Also included herein are antigen-binding fragments also comprising any combination of variable region(s) with a hinge region, CH1, CH2, and CH3 domains, the antigen being a peptide fragment of fibulin-3 consisting of the amino acid sequence of SEQ ID NO: 1 or SEQ ID NO: 2.

In one embodiment of this aspect and all other aspects described herein, the monoclonal anti-fibulin-3 antibody comprises a deletion of the CH2 domain.

In one embodiment of this aspect and all other aspects described herein, the isolated anti-fibulin-3 antibody described herein is a chimeric anti-fibulin-3 antibody.

In one embodiment of this aspect and all other aspects described herein, a chimeric anti-fibulin-3 antibody can contain at least the anti-fibulin-3 antigen binding Fab or F(ab)'2 region while a humanized antibody can contain at least the anti-fibulin-3 antigen binding Fv region fused to a human Fc region.

In one embodiment of this aspect and all other aspects described herein, the isolated anti-fibulin-3 antibody immunospecifically bind to an amino acid sequence of SEQ ID NO: 1 or 2 and do not cross-react with any other antigens.

The design of humanized immunoglobulins can be carried out as follows. When an amino acid falls under the following category, the framework amino acid of a human immunoglobulin to be used (acceptor immunoglobulin) is replaced by a framework amino acid from a CDR-providing non-human immunoglobulin (donor immunoglobulin): (a) the amino acid in the human framework region of the acceptor immunoglobulin is unusual for human immunoglobulins at that position, whereas the corresponding amino acid in the donor immunoglobulin is typical for human immunoglobulins in that position; (b) the position of the amino acid is immediately adjacent to one of the CDRs; or (c) the amino acid is capable of interacting with the CDRs (see, Queen et al. WO 92/11018., and Co et al., Proc. Natl. Acad. Sci. USA 88, 2869 (1991), respectively, both of which are incorporated herein by reference). For a detailed description of the production of humanized immunoglobulins see, Queen et al. and Co et al.

Usually the CDR regions in humanized antibodies and human antibody variants are substantially identical, and more usually, identical to the corresponding CDR regions in the mouse or human antibody from which they were derived. Although not usually desirable, it is sometimes possible to make one or more conservative amino acid substitutions of CDR residues without appreciably affecting the binding affinity of the resulting humanized immunoglobulin or human antibody variant. Occasionally, substitutions of CDR regions can enhance binding affinity.

Other than for the specific amino acid substitutions discussed above, the framework regions of humanized immunoglobulins and human antibody variants are usually substantially identical, and more usually, identical to the framework regions of the human antibodies from which they were derived (acceptor immunoglobulin). Of course, many of the amino acids in the framework region make little or no direct contribution to the specificity or affinity of an antibody. Thus, many individual conservative substitutions of framework residues can be tolerated without appreciable change of the specificity or affinity of the resulting humanized immunoglobulin or human antibody variants.

The variable segments of humanized antibodies or human antibody variants produced as described supra are typically linked to at least a portion of an immunoglobulin constant region (Fc), typically that of a human immunoglobulin Human constant region DNA sequences can be isolated in accordance with well-known procedures from a variety of human cells, such as immortalized B-cells (see Kabat et al., supra, and WO 87/02671). The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

The humanized antibody or human antibody variants include antibodies having all types of constant regions, including IgM, IgG, IgD, IgA and IgE, and any isotype, including IgG1, IgG2, IgG3 and IgG4. When it is desired that the humanized antibody or human antibody variants exhibit cytotoxic activity, the constant domain is usually a complement-fixing constant domain and the class is typically IgG1. When such cytotoxic activity is not desirable, the constant domain can be of the IgG2 class. The humanized antibody or human antibody variants can comprise sequences from more than one class or isotype.

In embodiment of this aspect and all other aspects described herein, the chimeric anti-fibulin-3 antibodies can comprise the VH region and/or VL region encoded by the nucleic acids of mouse or human anti-fibulin-3 antibody from selected hybridoma cell line described herein, and fused to the CH region and/or CL region of a another species, such as human or mouse or horse, etc. In other embodiments, a chimeric anti-fibulin-3 antibody comprises the VH and/or VL region fused to human C regions. The human CH2 domain can be deleted when antibodies are used in therapeutic purposes. Chimeric antibodies encompass antibody fragments, as described above.

In embodiment of this aspect and all other aspects described herein, the chimeric anti-fibulin-3 antibody comprises at least one of the amino acid sequences SEQ ID NO: 5-10.

In embodiment of this aspect and all other aspects described herein, the chimeric anti-fibulin-3 antibody comprises the VH region and/or VL region encoded by the nucleic acids comprising at least one of the nucleic acid sequences SEQ ID NO: 11-22.

The variable segments of chimeric antibodies are typically linked to at least a portion of an immunoglobulin constant region (Fc), typically that of a human immunoglobulin Human constant region DNA sequences can be isolated in accordance with well-known procedures from a variety of human cells, such as immortalized B-cells (see Kabat et al., supra, and WO 87/02671). The antibody can contain both light chain and heavy chain constant regions. The heavy chain constant region can include CH1, hinge, CH2, CH3, and, sometimes, CH4 regions. For therapeutic purposes, the CH2 domain can be deleted or omitted.

Chimeric antibodies include antibodies having all types of constant regions, including IgM, IgG, IgD, IgA and IgE, and any isotype, including IgG1, IgG2, IgG3 and IgG4. The chimeric antibody can comprise sequences from more than one class or isotype.

Many techniques developed for the production of chimeric antibodies are known in the art, for example, see Morrison et al., Proc. Natl. Acad. Sci. 81:851-855 (1984); Neuberger et al., Nature 312:604-608 (1984); Takeda et al., Nature 314:452-454 (1985) where splicing of genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine monoclonal antibody and a human immunoglobulin constant region, e.g., humanized antibodies.

A variety of methods are available for producing such immunoglobulins. Because of the degeneracy of the genetic code, a variety of nucleic acid sequences encode each immunoglobulin amino acid sequence. The desired nucleic acid sequences can be produced by de novo solid-phase DNA synthesis or by PCR mutagenesis of an earlier prepared variant of the desired polynucleotide. All nucleic acids encoding the antibodies described in this application are expressly included in the invention.

Once expressed, the whole antibodies, their dimers, individual light and heavy chains, or other immunoglobulin forms of the present invention can be purified according to standard procedures in the art, including ammonium sulfate precipitation, affinity columns, column chromatography, gel electrophoresis and the like (see, generally, Scopes, R., Protein Purification, Springer-Verlag, N.Y. (1982), which is incorporated herein by reference). Substantially pure immunoglobulins of at least about 90 to 95% homogeneity are preferred, and 98 to 99% or more homogeneity most preferred, for pharmaceutical uses.

In one embodiment of this aspect and all other aspects described herein, provided herein is a recombinant protein comprising the antigen binding region of an isolated antibody that immunospecifically binds an amino acid sequence of SEQ ID NO: 1 or SEQ ID NO: 2. This recombinant protein is hereby referred to as recombinant fibulin-3-binding protein.

In one embodiment, the recombinant protein comprising the antigen-binding region of a monoclonal antibody that specifically binds to an amino acid sequence of SEQ ID NO: 1 or 2 is a chimeric antigen receptor (CAR). In one embodiment, the CAR comprises one or more sequences selected from the group consisting of SEQ ID NOS: 3-10.

In one embodiment, the antigen binding region can include the Fab, F(ab)'2 or Fv fragment of any anti-fibulin-3 antibody. The non-antigen binding region of the protein can contain cysteine residues for the dimerization of the recombinant fibulin-3-binding protein. In another embodiment, the recombinant protein can be multivalent, having several antigen-binding regions in tandem in the polypeptide chain. The fibulin-3-binding recombinant protein can be conjugated to a detectable label, such as an enzyme, a fluorescent label, a luminescent label, or a bioluminescent label. The fibulin-3-binding recombinant protein can also be conjugated to a therapeutic or a liposome encapsulated with therapeutic agents, or a toxin e.g., a radioactive material.

In one embodiment, nucleic acid molecules encoding the anti-fibulin-3 antibodies, antibody fragments or variants thereof, and recombinant fibulin-3-binding proteins are included. In another embodiment, host cells comprising the nucleic acid molecules encoding the anti-fibulin-3 antibodies, antibody fragments or variants thereof, and recombinant fibulin-3-binding proteins are also included.

In one embodiment, a nucleic acid molecule encodes the isolated anti-fibulin-3 antibody described herein, including nucleic acid molecules that encode antibody fragments thereof. In one embodiment, the nucleic acid molecule comprises a VH region having an amino acid sequence of any one of the VH regions encoded by a nucleic acid an anti-fibulin-3 antibody and a VL region having an amino acid sequence of any one of the VL regions encoded by a nucleic acid of an anti-fibulin-3 antibody including a single chain antibody. For example, a nucleic acid selected from SEQ ID NO: 11-22.

Techniques for the production of single chain antibodies are also known in the art, for example, described in U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989), can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* can also be used (Skerra et al., Science 242:1038-1041 (1988)).

In one embodiment of this aspect and all other aspects described herein, the antibody is labeled with at least one agent.

In one embodiment of this aspect and all other aspects described herein, the agent include but is not limited to the group consisting of a radioisotope, a fluorescent compound, a bioluminescent compound, a chemiluminescent compound, a metal chelator, and an enzyme.

In one embodiment, the agent is a chemical compound or ion that possesses or comes to possess or is capable of generating a detectable signal. Examples of such agents includes, but are not limited to, radiolabels, such as, for example, 3H and 32P, that can be measured with radiation-counting devices; pigments, biotin, dyes or other chromogens that can be visually observed or measured with a spectrophotometer; spin labels that can be measured with a spin label analyzer; and fluorescent labels (fluorophores), where the output signal is generated by the excitation of a suitable molecular adduct and that can be visualized by excitation with light that is absorbed by the dye or can be measured with standard fluorometers or imaging systems. Examples of suitable radioisotopic labels include 111In, 125I, 131I, 35S, 14C, 51Cr, 57Co, 58Co, 59Fe, 75Se, 152Eu, 90Y, 67Cu, 217Ci, 211At, 212Pb, 47Sc, 109Pd etc. Examples of suitable non-radioactive isotopic labels include 157Gd, 55Mn, 162Dy, 52Tr, 56Fe etc.

Additional examples of agents for generating a detectable signal include, but are not limited to, a phosphorescent dye, a tandem dye and a particle. The label can be a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The term label also includes a "tag" or hapten that can bind selectively to a conjugated molecule such that the conjugated molecule, when added subsequently along with a substrate, is used to generate a detectable signal. For example, one can use biotin as a label and subsequently use an avidin or streptavidin conjugate of horseradish peroxidate (HRP) to bind to the biotin label, and then use a colorimetric substrate (e.g., tetramethylbenzidine (TMB)) or a fluorogenic substrate such as Amplex Red reagent (Molecular Probes, Inc.) to detect the presence of HRP. Numerous labels are known by those of skill in the art and include, but are not limited to, particles, fluorophores, haptens, enzymes and their colorimetric, fluorogenic and chemiluminescent substrates and other labels that are described in RICHARD P. HAUGLAND, MOLECULAR PROBES HANDBOOK OF FLUORESCENT PROBES AND RESEARCH PRODUCTS (9th edition, CD-ROM, (September 2002), which is herein incorporated by reference.

In one embodiment of this aspect and all other aspects described herein, the agent is a cytotoxic or a therapeutic agent.

In one embodiment of this aspect and all other aspects described herein, the cytotoxic agent includes but is not limited to the group consisting of ricin, ricin A-chain, doxorubicin, daunorubicin, taxol, ethidium bromide, mitomycin, etoposide, teniposide, vincristine, vinblastine, colchicine, dihydroxy anthracenedione, actinomycin, diphtheria toxin, *Pseudomonas* exotoxin (PE) A, PE40, abrin, abrin A chain, modeccin A chain, alpha-sarcin, gelonin, mitogellin, phenomycin, enomycin, curicin, calicheamicin, *Saponaria officinalis* inhibitor, and glucocorticoid.

In one embodiment of this aspect and all other aspects described herein, the radioisotope includes but is not limited to the group consisting of $^{212}$Bi, $^{131}$I, $^{131}$In, $^{90}$Y, and $^{186}$Re.

In one embodiment of this aspect and all other aspects described herein, the isolated anti-fibulin-3 antibody fragment is an Fab', F(ab')$_2$, or Fv. In one embodiment of this aspect and all other aspects described herein, the fragments or variants described herein exhibit immunospecific binding to the peptide fragment of fibulin-3 consisting of the amino acid sequence of SEQ ID NO: 1 or 2.

In one embodiment of this aspect and all other aspects described herein, the isolated anti-fibulin-3 antibody described here that comprise, or alternatively consist of, functional variants (including derivatives) of the antibody molecules (e.g., the VH regions and/or VL regions) described herein, the antibodies specifically binds a peptide fragment of fibulin-3 consisting of the amino acid sequence of SEQ ID NO: 1 or 2. Standard techniques known to those of skill in the art can be used to introduce mutations in the nucleotide sequence encoding a molecule of the invention, including, for example, site-directed mutagenesis and PCR-mediated mutagenesis which result in amino acid substitutions. Preferably, the variants (including derivatives) encode less than 50 amino acid substitutions, less than 40 amino acid substitutions, less than 30 amino acid substitutions, less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the reference VH region, VHCDR1, VHCDR2, VHCDR3, VL region, VLCDR1, VLCDR2, or VLCDR3. A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., the ability to immunospecifically bind to the peptide fragment of fibulin-3 consisting of the amino acid sequence of SEQ ID NO: 1 or 2).

For example, it is possible to introduce mutations only in framework regions or only in CDR regions of an antibody molecule. Introduced mutations can be silent or neutral missense mutations, i.e., have no, or little, effect on an antibody's ability to bind antigen. These types of mutations can be useful to optimize codon usage, or improve a hybridoma's antibody production. Alternatively, non-neutral missense mutations can alter an antibody's ability to bind antigen. The location of most silent and neutral missense mutations is likely to be in the framework regions, while the location of most non-neutral missense mutations is likely to be in CDR, though this is not an absolute requirement. One of skill in the art would be able to design and test mutant molecules with desired properties such as no alteration in antigen binding activity or alteration in binding activity (e.g., improvements in antigen binding activity or change in antibody specificity). Following mutagenesis, the encoded protein can routinely be expressed and the functional and/or biological activity of the encoded protein, (e.g., ability to immunospecifically binds the peptide fragment of fibulin-3 consisting of the amino acid sequence of SEQ ID NO: 1 or 2) can be determined using techniques described herein or by routinely modifying techniques known in the art.

Generation of Anti-Fibulin-3 Antibodies
Recombinant Expression Anti-Fibulin-3 Antibodies The antibodies and fragments that bind specifically to a peptide of fibulin-3 comprising or consisting of the amino acid sequence of SEQ ID NO: 1 or 2 can be produced by any method known in the art, for example, methods for the synthesis of antibodies, in particular, by chemical synthesis or preferably, by recombinant expression techniques.

The recombinant proteins described herein that specifically to a peptide of fibulin-3 comprising or consisting of the amino acid sequence of SEQ ID NO: 1 or 2 can be produced by any method known in the art for the expression and purification of recombinant proteins.

Recombinant expression of an antibody of the invention, or fragment, derivative or analog thereof, (e.g., a heavy or light chain of an antibody of the invention or a single chain antibody of the invention), including a recombinant protein derived from the antibody antigen-binding region, requires construction of an expression vector containing a polynucleotide that encodes the antibody. Once a polynucleotide encoding an antibody molecule or a heavy or light chain of an antibody or portion thereof (preferably containing the heavy or light chain variable domain) of the invention has been obtained, the vector for the production of the antibody molecule can be produced by recombinant DNA technology using techniques well known in the art. Thus, methods for preparing a protein by expressing a polynucleotide containing an antibody-encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors can include the nucleotide sequence encoding the constant region of the antibody molecule (see, e.g., PCT publication WO 86/05807; PCT publication WO 89/01036; and U.S. Pat. No. 5,122,464) and the variable domain of the antibody can be cloned into such a vector for expression of the entire heavy or light chain. Methods for generating multivalent and bispecific antibody fragments are described by Tomlinson I. and Holliger P. (2000) Methods Enzymol, 326, 461-479 and the engineering of antibody fragments and the rise of single-domain antibodies is described by Holliger P. (2005) Nat. Biotechnol. September; 23(9):1126-36, and are both hereby incorporated by reference.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains can be co-expressed in the host cell for expression of the entire immunoglobulin molecule, as detailed below.

A variety of host-expression vector systems can be utilized to express the antibody molecules of the invention. Such host-expression systems represent vehicles by which the coding sequences of interest can be produced and subsequently purified, but also represent cells which can, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene, 45:101 (1986); Cockett et al., BioTechnology, 8:2 (1990)).

In bacterial systems, a number of expression vectors can be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified can be desirable. Such vectors include, but are not limited to, the *E. coli* expression vector pUR278 (Ruther et al., EMBO J., 2:1791 (1983)), in which the antibody coding sequence can be ligated individually into the vector in frame with the lacZ coding region so that a fusion protein is produced; pIN vectors (Inouye & Inouye, Nucleic Acids Res., 13:3101-3109 (1985); Van Heeke & Schuster, J. Biol. Chem., 24:5503-5509 (1989)); and the like pGEX vectors can also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety. Expression of antibody fragments in Pichia pastoris is described by Holliger, P. (2002) Meth. Mol. Biol., 178: 349-57, and is hereby incorporated by reference in its entirety.

In an insect system, *Autographa californica* nuclear polyhedrosis virus (AcNPV) is used as a vector to express foreign genes. The virus grows in *Spodoptera frugiperda* cells. The antibody coding sequence can be cloned individually into non-essential regions (for example the polyhedrin gene) of the virus and placed under control of an AcNPV promoter (for example the polyhedrin promoter).

Advances in the large scale expression of heterologous proteins in the algae *Chlamydomonas reinhardtii* are described by Griesbeck C. et. al. 2006 Mol. Biotechnol. 34:213-33; Manuell A L et. al. 2007 Plant Biotechnol J. Eprint; Franklin S E and Mayfield S P, 2005, Expert Opin Biol Ther. February; 5(2):225-35; Mayfield S P and Franklin S E, 2005 Vaccine March 7; 23(15):1828-32; and Fuhrmann M. 2004, Methods Mol Med. 94:191-5. Foreign heterologous coding sequences are inserted into the genome of the nucleus, chloroplast and mitochodria by homologous recombination. The chloroplast expression vector p64 carrying the most versatile chloroplast selectable marker aminoglycoside adenyl transferase (aadA), which confers resistance to spectinomycin or streptomycin, can be used to express foreign protein in the chloroplast. Biolistic gene gun method is used to introduce the vector in the algae. Upon its entry into chloroplasts, the foreign DNA is released from the gene gun particles and integrates into the chloroplast genome through homologous recombination. Similarly, antibody productions in engineered Tobacco plants have been described by L. Both, et al, 2013, The FASEB J. Vol. 27, and by Lai H et al., Proc Natl Acad Sci USA. 2010, 107(6):2419-24. These references are hereby incorporated by reference in their entirety.

In mammalian host cells, a number of viral-based expression systems can be utilized. In cases where an adenovirus is used as an expression vector, the antibody coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. See, e.g., Logan & Shenk, Proc. Natl. Acad. Sci. USA, 81:355-359 (1984). Specific initiation signals can also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see, Bittner et al., Methods in Enzymol., 153:51-544 (1987)).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERY, BHK, Hela, COS, MDCK, NSO, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the antibody molecule. Such engineered cell lines can be particularly useful in screening and evaluation of compounds that interact directly or indirectly with the antibody molecule.

A number of selection systems can be used, including but not limited to the herpes simplex virus thymidine kinase (Wigler et al., Cell, 11:223 (1977)), hypoxanthine-guanine phosphoribosyltransferase (Szybalska & Szybalski, Proc. Natl. Acad. Sci. USA, 48:202 (1992)), and adenine phosphoribosyltransferase (Lowy et al., Cell, 22:817 (1980)) genes can be employed in tk-, hgprt- or aprt-cells, respectively. Also, anti-metabolite resistance can be used as the basis of selection for the following genes: dhfr, which confers resistance to methotrexate (Wigler et al., Proc. Natl. Acad. Sci. USA, 77:357 (1980); O'Hare et al., Proc. Natl. Acad. Sci. USA, 78:1527 (1981)); gpt, which confers resistance to mycophenolic acid (Mulligan & Berg, Proc. Natl. Acad. Sci. USA, 78:2072 (1981)); neo, which confers resistance to the aminoglycoside G-418; Wu and Wu, Biotherapy, 3:87-95 (1991); Tolstoshev, Ann Rev. Pharmacol. Toxicol., 32:573-596 (1993); Mulligan, Science, 260:926-932 (1993); and Morgan and Anderson, Ann. Rev. Biochem., 62:191-217 (1993); Can, 1993, TIB TECH 11(5):155-215); and hygro, which confers resistance to hygromycin (Santerre et al., Gene, 30:147 (1984)). Methods commonly known in the art of recombinant DNA technology can be routinely applied to select the desired recombinant clone, and such methods are described, for example, in Current Protocols in Molecular Biology, Ausubel et al., eds. (John Wiley & Sons, NY 1993); Kriegler, Gene Transfer and Expression, A Laboratory Manual (Stockton Press, NY 1990); and Current Protocols in Human Genetics, Dracopoli et al., eds. (John Wiley & Sons, NY 1994), Chapters 12 and 13; Colberre-Garapin et al., J. Mol. Biol., 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol., 3:257 (1983)).

The host cell can be co-transfected with two expression vectors of the invention, the first vector encoding a heavy chain derived polypeptide and the second vector encoding a light chain derived polypeptide. The two vectors can contain identical selectable markers which enable equal expression of heavy and light chain polypeptides. Alternatively, a single vector can be used which encodes, and is capable of expressing, both heavy and light chain polypeptides. In such situations, the light chain should be placed before the heavy chain to avoid an excess of toxic free heavy chain (Proudfoot, Nature, 322:52 (1986); Kohler, Proc. Natl. Acad. Sci. USA, 77:2197 (1980)). The coding sequences for the heavy and light chains can comprise cDNA or genomic DNA.

Once an antibody molecule of the invention has been produced by an animal or recombinantly expressed, it can be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

Antibody Production Using Hybridomas

Methods of producing monoclonal antibodies are known in the act. Such antibodies can be produced by hybridoma or recombinant techniques known in the art. As a starting point, polyclonal antibodies immunoreactive against a peptide of fibulin-3 comprising or consisting of the amino acid sequence of SEQ ID NO: 1 or 2 are needed. This is typically produced by inoculating or immunizing a mammal with the peptide of fibulin-3 comprising or consisting of the amino acid sequence of SEQ ID NO: 1 or 2 which serves as the antigen.

The processes of immunization to elicit antibody production in a mammal, the generation of hybridomas to produce monoclonal antibodies, and the purification of antibodies can be performed by described in "Current Protocols in Immunology" (CPI) (John Wiley and Sons, Inc.) and Antibodies: A Laboratory Manual (Edward A. Greenfield editor, Cold Spring Harbor Laboratory Press 2014, 2$^{nd}$ Edition) which are both incorporated by reference herein in their entireties.

The step of immunizing an animal for eliciting antibodies can include injecting the antigen directly into the animal. The animal can be a non-human mammal such as goats, mouse, donkey, sheep, and rabbit. For example, the antigen can be injected into a mouse to elicit polyclonal antibodies, or monoclonal antibodies by using a hybridoma technology. The animal can be a natural animal, a transgenic animal that has been genetically modified to produce human antibodies, such as XENOMOUSE™ and HuMab Mouse, or a transchromosome (TC) mouse.

Optionally, the step of immunizing the animal can include transfecting the animal with an expression vector encoding the antigen. For example, DNA sequence encoding the antigen can be inserted into a mammalian expression vector or a viral vector (e.g., retroviral, adenoviral, and adeno-associated viral vectors) and the resulting expression vector can be injected into the animal where the expression of the antigen by the vector elicits immune responses to the antigen. Antibodies can then be isolated from the serum of the animal and used to target the membrane protein for therapeutic or diagnostic purposes.

For example, naïve BALB/c mice are immunized with a peptide comprising SEQ ID NO:1 or 2 in complete Freund's adjuvant, where the peptide is not the full-length fibulin-3 polypeptide. Alternatively, a transgenic animal that has been genetically modified to produce human antibodies, such as XENOMOUSE™ and HuMab mouse, or a transchromosome (TC) mouse, can be immunized to generate anti-fibulin-3 polyclonal antibodies.

Hybridoma cell lines, specific for fibulin-3, can then be prepared using hybridoma technology. (Kohler et al., Nature 256:495 (1975); Kohler et al., Eur. J. Immunol 6511 (1976); Kohler et al., Eur. J. Immunol 6292 (1976); Hammerling et al., in: Monoclonal Antibodies and T-Cell Hybridomas, Elsevier, N.Y., pp. 571-681 (1981)). Briefly, hybridoma cell lines were generated using standard PEG fusion of the non-secreting myeloma cells to splenocytes overexpressing anti-fibulin-3 antibodies at a ratio 1:3 and selected in Hat (hypoxanthin, aminopterin, and thymidine) media in 96 well plates. After two weeks, individual supernatants were tested for reactivity with fibulin-3 by ELISA, Western blot, and immunohistochemistry. Positive hybridomas colonies were subcloned and screened for reactivity twice to ensure clonality. Antibodies were isolated from hybridoma supernatants by protein G affinity purification using standard methods.

From the hybridoma cell lines producing anti-fibulin-3 specific antibodies, the polynucleotides encoding the VL and VH regions of these antibodies can be cloned into cloning vectors such as TOPO vectors (e.g. INVITROGEN™ Inc.) and used for further molecular biology manipulations to generate other chimeric and humanized antibodies, variant forms of anti-fibulin-3 antibodies, and recombinant anti-fibulin-3 proteins by any method known in the art, such as those described in Michael R. Green and Joseph Sambrook, Molecular Cloning: A Laboratory Manual, Cold Spring Harbor Laboratory Press, Cold Spring Harbor, N.Y., USA (2012) and DNA Cloning Vols I, II, and III (D. Glover ed., IRL Press Ltd.), Sambrook et. al., (1989, Molecular Cloning, A Laboratory Manual; Cold Spring Harbor Laboratory Press, NY, USA), Current Protocols in Molecular Biology (CPMB) (Fred M. Ausubel, et al. ed., John Wiley and Sons, Inc.) and Current Protocols in Protein Science (CPPS) (John E. Coligan, et. al., ed., John Wiley and Sons, Inc.) which are all incorporated by reference herein in their entireties.

The nucleic acids corresponding to the VH and VL regions of the selected anti-fibulin-3 antibody are cloned by PCR cloning into one or more suitable expression vectors. By way of non-limiting example, PCR primers including VH or VL nucleotide sequences, a restriction site, and a flanking sequence to protect the restriction site can be used to amplify the VH or VL sequences. Utilizing cloning techniques known to those of skill in the art, the PCR amplified VH regions can be cloned into vectors expressing the appropriate immunoglobulin constant region, e.g., the human IgG1 or IgG4 constant region for VH regions, and the human kappa or lambda constant regions for kappa and lambda VL regions, respectively. Preferably, the vectors for expressing the VH or VL regions comprise a promoter suitable to direct expression of the heavy and light chains in the chosen expression system, a secretion signal, a cloning site for the immunoglobulin variable domain, immunoglobulin constant domains, and a selection marker such as neomycin. The VH and VL regions can also be cloned into a single vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art (See, for example, Guo et al., J. Clin. Endocrinol. Metab. 82:925-31 (1997), and Ames et al., J. Immunol Methods 184:177-86 (1995) which are herein incorporated in their entireties by reference).

The nucleic acid sequences encoding the anti-fibulin-3 antibodies can be used for transformation of a suitable mammalian or non-mammalian host cells or to generate phage display libraries, for example. Additionally, polypeptide antibodies can be chemically synthesized or produced through the use of recombinant expression systems that are known in the art.

Alternatively, murine antibodies which can be used in the preparation of the anti-fibulin-3 antibodies can be prepared by methods described in Rubin et al., EP 0218868 (published Apr. 22, 1987); Yone et al., EP 0288088 (published Oct. 26, 1988); Liang, et al., Biochem. Biophys. Res. Comm. 137:847-854 (1986); Meager, et al., Hybridoma 6:305-311 (1987); Fendly et al., Hybridoma 6:359-369 (1987); Bringman, et al., Hybridoma 6:489-507 (1987); Hirai, et al., J. Immunol. Meth. 96:57-62 (1987); Möller, et al., Cytokine 2:162-169 (1990).

The cell fusions are accomplished by standard procedures well known to those skilled in the field of immunology. Fusion partner cell lines and methods for fusing and selecting hybridomas and screening for mAbs are well known in the art. See, e.g., Ausubel infra, Harlow infra, and Colligan infra, the contents of which references are incorporated entirely herein by reference.

The anti-fibulin-3 murine monoclonal antibody (mAb) can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a hybridoma (e.g., rat or human), hybridoma cells are preferably grown in irradiated or athymic nude mice. alternatively, the antibodies can be produced by culturing hybridoma or transfectoma cells in vitro and isolating secreted mAb from the cell culture medium or recombinantly, in eukaryotic or prokaryotic cells.

Uses of Anti-Fibulin-3 Antibodies

In one embodiment, this disclosure provides a method of inducing cytotoxicity or apoptosis or inhibiting cancer cells comprising contacting a cancer cell with an effective amount of an antibody or a fragment thereof described herein, or recombinant protein described, or with a composition described or with a pharmaceutical composition described.

In one embodiment, as used in this context, "inducing cytotoxicity or apoptosis or inhibiting cancer cells" means to an increase cell death of cancer cells that have been contacted with an anti-fibulin-3 antibody, fragment, variant, and the composition described herein by at least 10% compared to the absence of any similar contacting.

In another embodiment, as used in this context, "inducing cytotoxicity or apoptosis or inhibiting cancer cells" means to a reduction of cell proliferation or spreading of the contacted cancer cell by at least 10% compared to the absence of any similar contacting.

In some embodiments, the inducing cytotoxicity or apoptosis or inhibiting cancer cells occurs in vitro or ex vivo, such is in tissue or cell culture experiments. For example, in vitro or ex vivo experiments can be conducted for the purpose of determining the dosage and efficacy of the various anti-fibulin-3 antibodies, fragments, variants, and the compositions described herein. In other embodiments, the anti-fibulin-3 antibodies, fragments, variants, the recombinant protein described, and/or the compositions described herein are contacted in vivo to induce cytotoxicity or apoptosis or inhibit cancer cells in a subject. For example, the anti-fibulin-3 antibodies, fragments, variants, and the compositions described herein are directly injected into a tumor, or into an organ, e.g., the liver via intravenous delivery to the hepatic portal vein.

In one embodiment, this disclosure provides a method of treating a condition mediated by fibulin-3 activity in a subject, the method comprising administering a composition comprising an effective amount of an antibody or a fragment thereof described herein, or recombinant protein described, or with a composition described or with a pharmaceutical composition described to the subject.

In one embodiment, this disclosure provides a method for inhibiting aberrant angiogenesis in a subject, the method comprising administering a composition comprising an effective amount of an antibody or a fragment thereof described herein, or recombinant protein described, or with a composition described or with a pharmaceutical composition described to the subject.

In some embodiments, the inhibiting aberrant angiogenesis occurs in vitro or ex vivo, such is in tissue or cell culture experiments. For example, in vitro or ex vivo experiments can be conducted for the purpose of determining the dosage and efficacy of the various anti-fibulin-3 antibodies, fragments, variants, recombinant protein described, and/or the compositions described herein. In other embodiments, the anti-fibulin-3 antibodies, fragments, variants, recombinant protein described, and/or the compositions described herein are contacted in vivo to inhibiting aberrant angiogenesis in a subject. For example, the anti-fibulin-3 antibodies, fragments, variants, recombinant protein described, and/or the compositions described herein are directly injected into a tumor, or into an organ, e.g., the liver via intravenous delivery to the hepatic portal vein.

In one embodiment, this disclosure provides a method of treatment of malignant cancer in a subject comprising administering a composition comprising an effective amount of an antibody or a fragment thereof described herein, or recombinant protein described, or with a composition described or with a pharmaceutical composition described to the subject. In one embodiment, treatment includes increase in the life span or prolong survival of the subject having cancer. In one embodiment, the increase can be about 10% longer over the average survival for the respective cancer in subjects. In some embodiments, the increase can be about 20%, 30%, 40%, 50%, 60% or more longer over the average survival for the respective cancer in subjects. In one embodiment, treatment includes decrease in the growth of tumors in the subject having cancer. In one embodiment, the decrease can be about 10% over the average rate of tumor growth for the respective cancer in subjects. In some embodiments, the decrease can be about 20%, 30%, 40%, 50%, 60% or more over the average rate of tumor growth for the respective cancer in subjects.

In one embodiment, this disclosure provides a method of enhancing the effectiveness of a cancer therapy comprising administering a composition comprising an effective amount of an antibody or a fragment thereof described herein, or recombinant protein described, or a pharmaceutical composition comprising an antibody or a fragment thereof described herein to the subject in conjunction with the cancer therapy or during the cancer therapy. In other word, the subject can be one who is already receiving or undergoing a cancer therapy that does not include the anti-fibulin-3 antibodies, fragments, variants, recombinant protein described, and/or the compositions described herein. To this subject, an anti-fibulin-3 antibody, fragment, variant, and/or the composition described herein is administered in addition to the subject's anti-cancer therapy for the purpose of enhancing the effectiveness of that cancer therapy. For example, the subject is currently being treated with temozolomide. An anti-fibulin-3 antibody, fragment, variant, or the composition described herein is administered in addition to the subject's temozolomide chemotherapy. The anti-fibulin-3 antibody, fragment, variant, recombinant protein described, and/or the composition described herein can be administered simultaneously or sequentially with temozolomide. In one embodiment, the administration of an anti-fibulin-3 antibody, fragment, variant, and/or the composition described herein and temozolomide in alternating, i.e., one administration of an anti-fibulin-3 antibody, fragment, variant, and/or the composition described herein followed by temozolomide and then next with an anti-fibulin-3 antibody, fragment, variant, recombinant protein described, and/or the composition described herein and so forth.

The cancer therapy is one that in conventional or know in the art and is currently used in practice. The cancer therapy does not comprise a composition comprising an effective amount of an antibody or a fragment thereof that binds to a peptide fragment consisting of the amino acid sequence of SEQ ID NO: 1 or 2.

In one embodiment, the method of enhancing the effectiveness of a cancer therapy further comprises selecting a subject who currently is already receiving or undergoing a cancer therapy that does not include the anti-fibulin-3 antibodies, fragments, variants, and the compositions described herein. In some embodiments, the selected subject has been receiving or undergoing a cancer therapy less than 1 week, less than two weeks, less than three weeks, less than four weeks, less than one month, not more than one month, not more than one week, not more than, not more than two weeks, not more than three weeks, not more than four weeks, not more than five weeks, not more than five weeks, not more than six weeks, not more than seven weeks, not more than eight weeks, and not more than two months.

In one embodiment, the method of enhancing the effectiveness of a cancer therapy further comprises selecting a subject who has previously complete at least one cancer therapy regime, and is about to start another cancer therapy regime. In one embodiment, the cancer in the selected subject has relapse and therefore is need of another cancer therapy.

In one embodiment, this disclosure provides a method of enhancing the effectiveness of a cancer therapy comprising selecting a subject who currently is already receiving or undergoing a cancer therapy or selecting a subject who has previously complete at least one cancer therapy regime, and is about to start another cancer therapy regime, and administering a composition comprising an effective amount of an antibody or a fragment thereof described herein or a pharmaceutical composition comprising an antibody or a fragment thereof described herein to the subject in conjunction with the cancer therapy or during the cancer therapy, wherein undergoing a cancer therapy that does not include the anti-fibulin-3 antibodies, fragments, variants, recombinant protein described, and the compositions described herein.

In one embodiment, this disclosure provides a method of treatment of malignant cancer in a subject comprising administering (a) a composition comprising an effective amount of an antibody or a fragment thereof described herein, or recombinant protein described, or a pharmaceutical composition comprising an antibody or a fragment thereof described herein and; (b) at least one additional cancer therapy to the subject. The cancer therapy is one that in conventional or know in the art and is currently used in practice. The cancer therapy does not comprise a composition comprising an effective amount of an antibody or a fragment thereof, or recombinant protein described, that binds to a peptide fragment consisting of the amino acid sequence of SEQ ID NO: 1 or 2.

In one embodiment, the method of treatment of malignant cancer in a subject further comprises selecting a subject who currently is already receiving or undergoing a cancer therapy that does not include the anti-fibulin-3 antibodies, fragments, variants, and the compositions described herein. In some embodiments, the selected subject has been receiving or undergoing a cancer therapy less than 1 week, less than two weeks, less than three weeks, less than four weeks, less than one month, not more than one month, not more than one week, not more than, not more than two weeks, not more than three weeks, not more than four weeks, not more than five weeks, not more than five weeks, not more than six weeks, not more than seven weeks, not more than eight weeks, and not more than two months.

In one embodiment, the method of treatment of malignant cancer in a subject further comprises selecting a subject who has been diagnosed of a malignant cancer.

In one embodiment, the method of treatment of malignant cancer in a subject further comprises selecting a subject who has previously complete at least one cancer therapy regime, and is about to start another cancer therapy regime. In one embodiment, the cancer in the selected subject has relapse and therefore is need of another cancer therapy.

In one aspect of any method described herein, the method comprises administering an antibody or recombinant protein comprising any one or more of SEQ ID NOS: 3-10, 23-26.

In one aspect of any method described herein, the method comprises administering an antibody or recombinant protein consisting essentially of any one or more of SEQ ID NOS: 3-10, 23-26.

In one aspect, this disclosure provides a use of a composition comprising the antibody or fragment thereof described, a recombinant protein described, a light chain of the antibody described, a heavy chain of the antibody described for inhibiting cancer cells.

In other aspect, this disclosure provides a use of a composition comprising the antibody or fragment thereof described, a recombinant protein described, a light chain of the antibody described, and/or a heavy chain of the antibody described for treating a condition mediated by fibulin-3 activity in a subject.

In other aspect, this disclosure provides a use of a composition comprising the antibody or fragment thereof described, a single chain antibody described, a recombinant protein described, a light chain of the antibody described, and/or a heavy chain of the antibody described for inhibiting aberrant angiogenesis in a subject.

In other aspect, this disclosure provides a use of a composition comprising the antibody or fragment thereof described, a single chain antibody described, a recombinant protein described, a light chain of the antibody described, and/or a heavy chain of the antibody described for treatment of malignant cancer in a subject.

In other aspect, this disclosure provides a use of a composition comprising the antibody or fragment thereof described, a single chain antibody described, a recombinant protein described, a light chain of the antibody described, and/or a heavy chain of the antibody described for the manufacture of medicament for treating a condition mediated by fibulin-3 activity in a subject.

In other aspect, this disclosure provides a use of a composition comprising the antibody or fragment thereof described, a single chain antibody described, a recombinant protein described, a light chain of the antibody described, and/or a heavy chain of the antibody described for the manufacture of medicament for inhibiting aberrant angiogenesis in a subject.

In other aspect, this disclosure provides a use of a composition comprising the antibody or fragment thereof described, a single chain antibody described, a recombinant protein described, a light chain of the antibody described, and/or a heavy chain of the antibody described for the manufacture of medicament for treatment of malignant cancer in a subject.

In other aspect, this disclosure provides a use of a composition comprising the antibody or fragment thereof described, a single chain antibody described, a recombinant protein described, a light chain of the antibody described, and/or a heavy chain of the antibody described for the manufacture of an adjuvant a cancer therapy used in the treatment of malignant cancer in a subject.

In one embodiment of this aspect and all other aspects described herein, the treatment methods further selecting a subject having malignant cancer.

In one embodiment of this aspect and all other aspects described herein, the methods of treating a condition mediated by fibulin-3 activity in a subject further comprises selecting a subject having a condition mediated by fibulin-3 activity.

In one embodiment of this aspect and all other aspects described herein, the selected a subject a condition mediated by fibulin-3 activity exhibits at least one symptom of at least one of the condition selected from the group consisting of malignant cancer, spontaneous maculopathies, inherited macular degeneration syndromes, and pterygium.

In one embodiment of this aspect and all other aspects described herein, the methods described herein further comprises selecting a subject diagnosed of having a malignant cancer, a spontaneous maculopathies, an inherited macular degeneration syndromes, or pterygium.

In one embodiment of this aspect and all other aspects described herein, the methods of inhibiting aberrant angiogenesis in a subject further comprises selecting a subject having aberrant angiogenesis.

In one embodiment of this aspect and all other aspects described herein, the contacting of cells is in vitro, in vivo or ex vivo.

In one embodiment of this aspect and all other aspects described herein, the cancer cells contacted are glioma cells. In other embodiments, the cancer cells contacted are pancreatic, cervical, ovarian, lung, nose, throat and bone cancer cells. In other embodiments, the contacted cells are cancer cells identified in the cancers shown in Table 1.

In one embodiment of this aspect and all other aspects described herein, the cancer cells are also contacted with at least one additional cancer therapeutic.

In one embodiment of this aspect and all other aspects described herein, the condition mediated by aberrant fibulin-3 activity is selected from malignant cancer, spontaneous maculopathies, inherited macular degeneration syndromes, and pterygium such as conjuctival hyperplasia.

In one embodiment of this aspect and all other aspects described herein, spontaneous maculopathy includes but is not limited to choroid hypervascularization or macular degeneration in the eye.

In one embodiment of this aspect and all other aspects described herein, inherited macular degeneration syndrome includes but is not limited to Doyne's Honeycomb retinal dystrophy or Malattia Levantinese.

In one embodiment of this aspect and all other aspects described herein, the cancer is glioma. In one embodiment of this aspect and all other aspects described herein, the cancer is astrocytomas. In other embodiments, the cancer is pancreatic, cervical, ovarian, lung, nose, throat and bone cancer. In other embodiments, the cancer is that identified in Table 1.

In one embodiment of this aspect and all other aspects described herein, the treatment method further comprises administering at least one other cancer therapy.

In one embodiment of this aspect and all other aspects described herein, the composition and the at least one other cancer therapy are administered simultaneously or sequentially to the subject.

In one embodiment of this aspect and all other aspects described herein, the at least one other cancer therapy is chemotherapy or radiation.

In one embodiment of this aspect and all other aspects described herein, the chemotherapy includes but is not limited to the temozolomide, carmustine, bevacizumab, procarbazine, lomustine (CCNU) and vincristine.

In one embodiment of this aspect and all other aspects described herein, the composition or pharmaceutical composition is administered by injection, infusion, or instillation.

In one embodiment of this aspect and all other aspects described herein, the antibody comprised in the pharmaceutical composition is linked to a therapeutic agent.

In one embodiment of this aspect and all other aspects described herein, the treatment method further comprises selecting an individual for treatment.

In some embodiments, the methods described herein relate to CAR-immune cell therapies such as CAR-T therapy. CAR-T and related therapies relate to adoptive cell transfer of immune cells (e.g. T cells) expressing a CAR that binds specifically to a targeted cell type (e.g. cancer cells) to treat a subject. In some embodiments, the cells administered as part of the therapy can be autologous to the subject. In some embodiments, the cells administered as part of the therapy are not autologous to the subject. In some embodiments, the cells are engineered and/or genetically modified to express the CAR. Further discussion of CAR-T therapies can be found, e.g., in Maus et al. Blood 2014 123:2624-35; Reardon et al. Neuro-Oncology 2014 16:1441-1458; Hoyos et al. Haematologica 2012 97:1622; Byrd et al. J Clin Oncol 2014 32:3039-47; Maher et al. Cancer Res 2009 69:4559-4562; and Tamada et al. Clin Cancer Res 2012 18:6436-6445; each of which is incorporated by reference herein in its entirety.

Formulation and Administration

The anti-fibulin-3 antibodies, fragments, variants, recombinant proteins described, and the compositions described herein can be used as a medicament or used to formulate a pharmaceutical composition with one or more of the utilities disclosed herein. They can be administered in vitro to cells in culture, or in vivo to cells in the body, or in vivo administration to a subject.

The anti-fibulin-3 antibodies, fragments, variants, recombinant proteins described, and the compositions described herein can be used to produce a medicament or other pharmaceutical compositions. Use of The anti-fibulin-3 antibodies, fragments, variants, and the compositions described herein further comprise a pharmaceutically acceptable carrier and the compositions which further comprise components useful for delivering the composition to a subject are known in the art. Addition of such carriers and other components to the anti-fibulin-3 antibodies, fragments, variants described herein as disclosed herein is well within the level of skill in this art.

In some embodiments, the anti-fibulin-3 antibodies, fragments, variants, and the therapeutic compositions described herein are formulated to contain a physiologically tolerable carrier together with an active agent as described herein, dissolved or dispersed therein as an active ingredient. In a preferred embodiment, the therapeutic composition is not immunogenic when administered to a mammal or human patient for therapeutic purposes. The therapeutic combinations described herein comprise the anti-fibulin-3 antibodies, fragments, and/or variants, described herein. In other embodiments, the therapeutic compositions described herein is a combination composition consisting of at least one chemotherapy drug such as temozolomide, carmustine, bevacizumab, procarbazine, lomustine (CCNU) and vincristine, in combination with at least one anti-fibulin-3 antibodies, fragments, or variants, or recombinant protein described herein. The compositions can have more than one chemotherapy drug and/or more than one anti-fibulin-3 antibodies, fragments, and/or variants described herein.

As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Typically such compositions are prepared as injectable either as liquid solutions or suspensions, however, solid forms suitable for solution, or suspensions, in liquid prior to use can also be prepared. The preparation can also be emulsified or presented as a liposome composition. The active ingredient can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition of the present invention can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of an active agent used in the methods described herein that will be effective in the treatment of a particular disorder or condition will depend on the nature of the disorder or condition, and can be determined by standard clinical techniques. Suitable pharmaceutical carriers are described in Remington's Pharmaceutical Sciences, A. Osol, a standard reference text in this field of art. For example, a parenteral composition suitable for administration by injection is prepared by dissolving 1.5% by weight of active ingredient in 0.9% sodium chloride solution.

In one embodiment, the "pharmaceutically acceptable" carrier does not include in vitro cell culture media.

Therapeutic compositions or pharmaceutical compositions can be formulated for passage through the blood-brain barrier or direct contact with the endothelium. In some embodiments, the compositions can be formulated for systemic delivery. In some embodiments, the compositions can be formulated for delivery to specific organs, for example but not limited to the liver, spleen, the bone marrow, and the skin. Therapeutic compositions or pharmaceutical compositions can be formulated for aerosol application by inhalation the lung. Alternatively, the therapeutic compositions or pharmaceutical compositions can also be formulated for a transdermal delivery, e.g. a skin patch. Therapeutic compositions or pharmaceutical compositions can be enteric coated and formulated for oral delivery. Therapeutic compositions or pharmaceutical compositions can be encapsulated in liposomes or nanoparticles and formulated for slow sustained delivery in vivo. Alternatively, the therapeutic compositions or pharmaceutical compositions is be formulated for targeted delivery, e.g., encapsulated in liposomes or nanoparticles that are designed and feature targeting moiety to on the liposomes or nanoparticles.

The anti-fibulin-3 antibodies, fragments, variants, recombinant proteins, chemotherapy drugs such as temozolomide, carmustine, bevacizumab, procarbazine, lomustine (CCNU) and vincristine, and the compositions described herein can be administered by any known route. By way of example, the anti-fibulin-3 antibodies, fragments, variants, and the compositions described herein can be administered by a mucosal, pulmonary, topical, or other localized or systemic route (e.g., enteral and parenteral). Routes of administration include, but are not limited to aerosol, direct injection, intradermal, transdermal (e.g., in slow release polymers), intravitreal, intramuscular, intraperitoneal, intravenous, subcutaneous, intranasal, epidural, topical, oral, transmucosal, buccal, rectal, vaginal, transdermal, intranasal and parenteral routes. "Parenteral" refers to a route of administration that is generally associated with injection, including but not limited to intraorbital, infusion, intraarterial, intracapsular, intracardiac, intradermal, intrahepatic, intrarogan, intramuscular, intraperitoneal, intrapulmonary, intraspinal, intrasternal, intrathecal, intrauterine, intravenous, subarachnoid, subcapsular, subcutaneous, transmucosal, or transtracheal. Any other therapeutically efficacious route of administration can be used, for example, infusion or bolus injection, absorption through epithelial or mucocutaneous linings, or by gene therapy wherein a DNA molecule encoding the therapeutic protein or peptide is administered to the patient, e.g., via a vector, which causes the protein or peptide to be expressed and secreted at therapeutic levels in vivo. In various embodiments, administration can be inhaled in to the lung via aerosol administration, e.g. with nebulization. Administration also can be systemic or local.

For example, the therapeutic compositions or pharmaceutical compositions can be administered as a formulation adapted for passage through the blood-brain barrier or direct contact with the endothelium. In some embodiments, the compositions can be administered as a formulation adapted for systemic delivery. In some embodiments, the compositions can be administered as a formulation adapted for delivery to specific organs, for example but not limited to the liver, spleen, the bone marrow, and the skin.

In addition, the anti-fibulin-3 antibodies, fragments, variants, recombinant protein, chemotherapy drugs such as temozolomide, carmustine, bevacizumab, procarbazine, lomustine (CCNU) and vincristine, and the compositions described herein can be administered together with other components of biologically active agents, such as pharmaceutically acceptable surfactants (e.g., glycerides), excipients (e.g., lactose), carriers, diluents and vehicles.

The anti-fibulin-3 antibodies, fragments, variants, recombinant proteins, and the compositions described herein can be administered therapeutically to a subject prior to, simultaneously with (in the same or different compositions) or sequentially with the administration of at least one other cancer therapy. For example, the addition cancer therapy is radiation or chemotherapy or proton therapy. The anti-fibulin-3 antibodies, fragments, variants, and the compositions described herein antagonists can be administered as adjunctive and/or concomitant therapy to a cancer therapy.

For parenteral (e.g., intravenous, subcutaneous, intramuscular) administration, anti-fibulin-3 antibodies, fragments, variants, recombinant proteins, and the compositions described herein can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and nonaqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques.

In one embodiment, it may be desirable to administer the isolated antibody or pharmaceutical compounds or compositions described herein locally to the area in need of treatment; this may be achieved by, for example, and not by way of limitation, local infusion during surgery, topical application, e.g., in conjunction with a wound dressing after surgery, by injection, by means of a catheter; by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the isolated antibody or composition described herein can be delivered in a vesicle, in particular a liposome. (see Langer, 1990, Science 249:1527-1533; Treat et al., in Liposomes in the Therapy of Infectious Disease and Cancer, Lopez-Berestein and Fidler (eds.), Liss, New York, (1989).

In another embodiment, the isolated antibody or composition described herein can be delivered in a controlled release system. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574).

Other controlled release systems are discussed in the review by Langer (1990, Science 249:1527-1533). The compositions of the invention are also suitably administered by sustained-release systems. Suitable examples of sustained-release compositions include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly (2-hydroxyethyl methacrylate) (R. Langer et al., J. Biomed Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988).

Sustained-release compositions also include liposomally entrapped compositions of the invention (see generally, Langer, Science 249:1527-1533 (1990); Treat et al., in Liposomes in the Therapy of Infectious Disease and Cancer, Lopez-Berestein and Fidler (eds.), Liss, New York, pp. 317-327 and 353-365 (1989)). Liposomes containing DR5 polypeptide my be prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal DR5 polypeptide therapy.

In one embodiment where the nucleic acid encoding a protein is administered, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

In yet an additional embodiment, the isolated antibody, recombinant proteins, nucleic acids or compositions described are delivered by way of a pump (see Langer, supra; Sefton, CRC Crit. Ref Biomed. Eng. 14:201 (1987); Buchwald et al., Surgery 88:507 (1980); Saudek et al., N. Engl. J. Med. 321:574 (1989)).

The anti-fibulin-3 antibodies, fragments, variants, recombinant proteins, and the compositions described herein are administered in therapeutically effective amounts. As used herein, a "therapeutically effective amount" is such that administration results in the inhibition of aberrant angiogenesis or inhibition of cancer cells (i.e. growth, proliferation, spread, and metastasis) or promotion of cytotoxicity relative to the absence of any anti-fibulin-3 antibodies, fragments, variants, and the compositions described herein administered. A therapeutically effective amount is preferably an amount of anti-fibulin-3 antibodies, fragments, variants, recombinant proteins, and the compositions described herein that is necessary to significantly reduce or eliminate signs and symptoms associated with a condition mediated by fibulin-3 activity, for example, malignant cancer, spontaneous maculopathies, inherited macular degeneration syndromes, and pterygium. In one embodiment, a therapeutically effective amount is not necessarily an amount such that administration of the any anti-fibulin-3 antibodies, fragments, variants, recombinant proteins, or compositions thereof alone must necessarily result in inhibition of aberrant angiogenesis or inhibition of cancer cells or significantly reduce or eliminate signs and symptoms associated with a condition mediated by fibulin-3 activity.

Once a therapeutically effective amount has been administered, a maintenance amount of anti-fibulin-3 antibodies, fragments, variants, recombinant proteins, and the composition thereof alone, or of a combination of anti-fibulin-3 antibodies, fragments, variants, recombinant proteins, and an additional cancer therapy can be administered to the subject. For example, the cancer therapy is a chemotherapy drug such as temozolomide. A maintenance amount is the amount of anti-fibulin-3 antibodies, fragments, variants, or combination of anti-fibulin-3 antibodies, fragments, variants, and the composition thereof and an additional cancer therapy necessary to maintain the reduction or elimination of the signs and symptoms associated with a condition mediated by fibulin-3 activity, for example, malignant cancer, spontaneous maculopathies, inherited macular degeneration syndromes, and pterygium, achieved by the therapeutically effective dose. The maintenance amount can be administered in the form of a single dose, or a series or doses separated by intervals of days or weeks.

The dosage administered to a subject will vary depending upon a variety of factors, including the pharmacodynamic characteristics of the particular antagonists, and its mode and route of administration; size, age, sex, health, body weight and diet of the recipient; nature and extent of symptoms of the disease being treated, kind of concurrent treatment, frequency of treatment, and the effect desired.

Usually a daily dosage of active ingredient can be about 0.01 to 500 milligrams per kilogram of body weight. Ordinarily 1 to 40 milligrams per kilogram per day given in divided doses 1 to 6 times a day or in sustained release form is effective to obtain desired results. The active ingredient will ordinarily be present in an amount of about 0.5-95% by weight based on the total weight of the composition. Second or subsequent administrations can be administered at a dosage which is the same, less than or greater than the initial or previous dose administered to the individual.

A second or subsequent administration is preferably during or immediately prior to relapse or a flare-up of the disease or symptoms of the disease. For example, second and subsequent administrations can be given between about one day to 30 weeks from the previous administration. Two, three, four or more total administrations can be delivered to the individual, as needed.

The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

Efficacy testing can be performed during the course of treatment using the methods described herein. Measurements of the degree of severity of a number of symptoms associated with a particular ailment are noted prior to the start of a treatment and then at later specific time period after the start of the treatment.

In vitro and in vivo methods of determining the inhibition of aberrant angiogenesis or inhibition of cancer cells or promotion of cytotoxicity in an individual are well known to those of skill in the art. Such in vitro assays can include a cytotoxicity assay (e.g., the WEHI assay or a radioimmunoassay, ELISA). In vivo methods can include rodent lethality assays and/or primate pathology model systems (Mathison et al., J. Clin. Invest., 81:1925-1937 (1988); Beutler et al., Science 229:869-871 (1985); Tracey et al., Nature 330: 662-664 (1987); Shimamoto et al., Imunol. Lett. 17:311-318 (1988); Silva et al., J. Infect. Dis. 162:421-427 (1990); Opal et al., J. Infect. Dis. 161:1148-1152 (1990); Hinshaw et al., Circ. Shock 30:279-292 (1990)).

The anti-fibulin-3 antibodies, fragments, variants, recombinant proteins, and the compositions described herein can be administered in single or multiple doses depending upon factors such as nature and extent of symptoms, kind of concurrent treatment and the effect desired. In addition, other therapeutic regimens or agents (e.g., multiple drug regimens) can be used in combination with the therapeutic co-administration of anti-fibulin-3 antibodies, fragments, variants, and the compositions described herein. In a particular embodiment, the anti-fibulin-3 antibody, fragment, variant, or the composition described herein is administered in multiple doses, with or without an additional cancer therapy such as temozolomide. In another embodiment, the anti-fibulin-3 antibodies, fragments, variants described herein are administered in the form of a series of low doses separated by intervals of days or weeks. In one embodiment, the anti-fibulin-3 antibodies, fragments, variants described herein are administered first, followed by temozolomide in the form of a series of low doses separated by intervals of days or weeks. Adjustment and manipulation of established dosage ranges are well within the ability of those skilled in the art.

The present invention can be defined in any of the following numbered paragraphs:

[1] An isolated antibody that binds to an amino acid sequence of SEQ ID NO: 1 or 2.
[2] The antibody of paragraph 1, wherein the antibody is monoclonal antibody.
[3] The antibody of paragraph 1, wherein said antibody is a single chain antibody.
[4] The antibody of paragraph 1, wherein said antibody is a single chain Fv (scFv) fragment.
[5] The antibody of paragraph 1, wherein said antibody is a Fab fragment.
[6] The antibody of paragraph 1, wherein said antibody is a humanized antibody.
[7] The antibody of paragraph 1, wherein said antibody is a chimeric antibody.
[8] The antibody of paragraph 1, wherein said antibody is produced by a hybridoma cell line.
[9] The antibody of paragraph 1, wherein said antibody comprises the amino acid sequence SEQ ID NO: 3 or 4.
[10] The antibody of paragraph 1, wherein said antibody comprises at least one of the amino acid sequences SEQ ID NO: 5-10.
[11] The antibody of paragraph 1, wherein said antibody is labeled with an agent.
[12] The antibody of paragraph 11, wherein the agent is selected from the group consisting of a radioisotope, fluorescent compound, bioluminescent compound, chemiluminescent compound, metal chelator, and enzyme.
[13] The antibody of paragraph 11, wherein the agent is a cytotoxic or a therapeutic agent.
[14] The antibody of paragraph 13, wherein the cytotoxic agent is selected from the group consisting of ricin, ricin A-chain, doxorubicin, daunorubicin, taxol, ethidium bromide, mitomycin, etoposide, teniposide, vincristine, vinblastine, colchicine, dihydroxy anthracenedione, actinomycin, diphtheria toxin, *Pseudomonas* exotoxin (PE) A, PE40, abrin, abrin A chain, modeccin A chain, alpha-sarcin, gelonin, mitogellin, phenomycin, enomycin, curicin, calicheamicin, *Saponaria officinalis* inhibitor, and glucocorticoid.
[15] The antibody of paragraph 12, wherein the radioisotope is selected from the group consisting of $^{212}$Bi, $^{131}$I, $^{131}$In, $^{90}$Y, and $^{186}$Re.
[16] A recombinant protein comprising the antigen-binding region of a monoclonal antibody of paragraph 2.
[17] A heavy chain of the antibody of paragraph 2.
[18] A light chain of the antibody of paragraph 2.
[19] A hybridoma producing a monoclonal antibody of paragraph 2.
[20] A cell line producing the antibody of paragraph 2.
[21] A kit comprising an antibody according to any one of paragraphs 1-15, a protein of paragraphs 16-18, a hybridoma of paragraph 19, and/or a cell line of paragraph 20.
[22] A composition comprising the antibody according to any one of paragraphs 1-15 or a protein of paragraphs 16-18.
[23] A pharmaceutical composition comprising the antibody according to any one of paragraphs 1-15 and/or a protein of paragraphs 16-18, and a pharmaceutically acceptable excipient.
[24] The pharmaceutical composition of paragraph 23, wherein the antibody is linked to a therapeutic agent.
[25] A method of inducing cytotoxicity or apoptosis, of inhibiting cancer cells, or reducing invasiveness of cancer cells comprising contacting a cancer cell with an effective amount of an antibody of paragraphs 1-15, or with a composition of paragraph 22 or with a pharmaceutical composition of paragraphs 23-24.

[26] The method of paragraph 25, wherein the contacting is in vitro, in vivo or ex vivo.

[27] The method of paragraph 25, wherein the cancer cells are glioma cells.

[28] The method of paragraph 25, wherein the cancer cells are also contacted with at least one additional cancer therapeutic.

[29] A method of treating a condition mediated by fibulin-3 activity in a subject, the method comprising administering a composition comprising an effective amount of an antibody of paragraphs 1-15 or with a composition of paragraph 22 or with a pharmaceutical composition of paragraphs 23-24 to the subject.

[30] The method of paragraph 29, wherein the condition mediated by aberrant fibulin-3 activity is selected from malignant cancer, spontaneous maculopathies, inherited macular degeneration syndromes, and pterygium.

[31] A method for inhibiting aberrant angiogenesis in a subject, the method comprising administering a composition comprising an effective amount of an antibody of paragraphs 1-15, or with a composition of paragraph 22 or with a pharmaceutical composition of paragraphs 23-24 to the subject.

[32] A method of treatment of malignant cancer in a subject comprising administering a composition comprising an effective amount of an antibody of paragraphs 1-15, or with a composition of paragraph 22 or with a pharmaceutical composition of paragraphs 20-21 to the subject.

[33] The method of paragraph 32, wherein the cancer is glioma (astrocytomas).

[34] The method of paragraph 32 further comprising administering at least one additional cancer therapy.

[35] The method of paragraph 34, wherein the composition and the at least one additional cancer therapy are administered simultaneously or sequentially to the subject.

[36] The method of paragraph 35, the at least one additional cancer therapy is chemotherapy or radiation.

[37] The method of paragraph 36, wherein the chemotherapy is temozolomide, carmustine, bevacizumab, procarbazine, lomustine (CCNU) and vincristine.

[38] The method of paragraphs 29-37, wherein the composition or pharmaceutical composition is administered by injection, infusion, or instillation.

[39] The methods of paragraph 31 further selecting a subject having a condition mediated by fibulin-3 activity.

[40] The methods of paragraph 39, wherein the selected a subject a condition mediated by fibulin-3 activity exhibits at least one symptom of at least one of the condition selected from the group consisting of malignant cancer, spontaneous maculopathies, inherited macular degeneration syndromes, and pterygium.

[41] The methods of paragraph 29 further selecting a subject having aberrant angiogenesis.

[42] The methods of paragraph 32 further selecting a subject having malignant cancer.

[43] Use of a composition comprising the antibody according to any one of paragraphs 1-15 and/or a protein of paragraphs 16-18 for inhibiting cancer cells.

[44] Use of a composition comprising the antibody according to any one of paragraphs 1-15 and/or a protein of paragraphs 16-18 for treating a condition mediated by fibulin-3 activity in a subject.

[45] Use of a composition comprising the antibody according to any one of paragraphs 1-15 and/or a protein of paragraphs 16-18 for inhibiting aberrant angiogenesis in a subject.

[46] Use of a composition comprising the antibody according to any one of paragraphs 1-15 and/or a protein of paragraphs 16-18 for treatment of malignant cancer in a subject.

[47] Use of a composition comprising the antibody according to any one of paragraphs 1-15 and/or a protein of paragraphs 16-18 for the manufacture of medicament for treating a condition mediated by fibulin-3 activity in a subject.

[48] Use of a composition comprising the antibody according to any one of paragraphs 1-15 and/or a protein of paragraphs 16-18 for the manufacture of medicament for inhibiting aberrant angiogenesis in a subject.

[49] Use of a composition comprising the antibody according to any one of paragraphs 1-15 and/or a protein of paragraphs 16-18 for the manufacture of medicament for treatment of malignant cancer in a subject.

This disclosure is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the disclosure described herein. Such equivalents are intended to be encompassed by the following claims.

Example

The region of fibulin-3 that activates Notch signaling is restricted to a short sequence in the protein.

Figure 4:
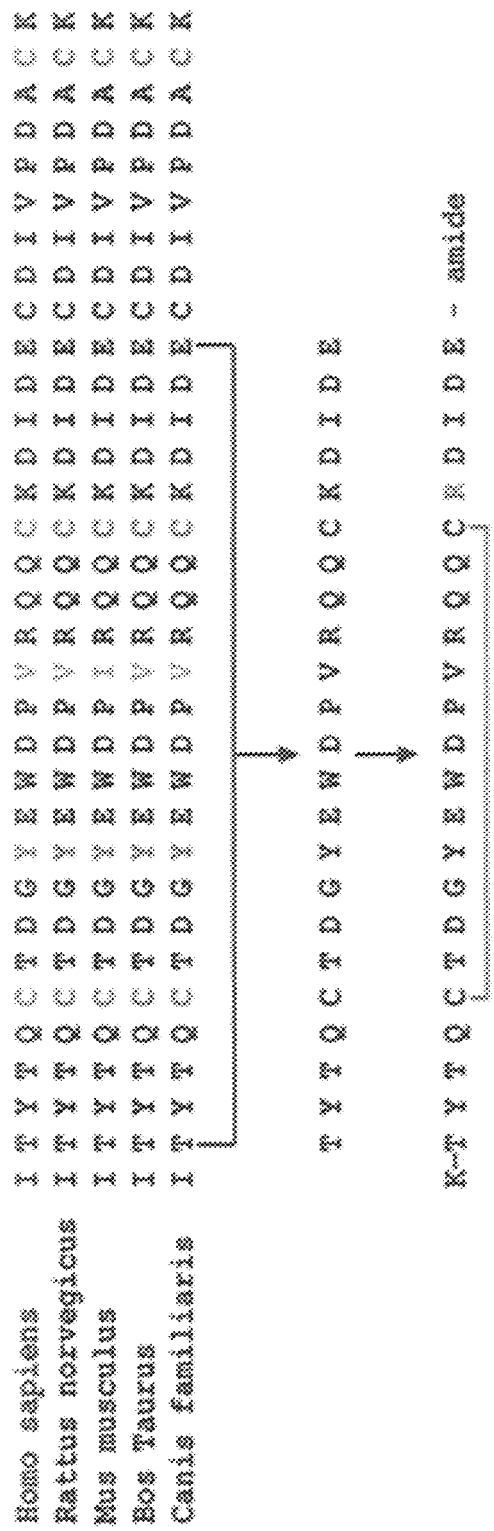
FIG. 4 shows the design of the immunizing peptide to generate anti-fibulin-3 antibodies.

Using deletion constructs, the inventors showed that the N-terminal domain of fibulin-3 was necessary to activate the Notch signaling pathway in glioma cells (FIG. 2). Further refinement of this strategy revealed a short sequence of 23 amino acids in fibulin-3 that was necessary to activate the Notch signaling pathway (FIG. 3). This sequence is highly conserved in different species (FIG. 4). The peptide sequence ranging from Thr25 to Cys70 in fibulin-3 is highly conserved among mammalian species. This sequence has high homology to sequences in other Notch-activating proteins and contains most of the Cys residues that form the Notch-activating DSL motif (13). Deletion of the sequence Thr25-Glu48 was demonstrated to abolish fibulin-3 functionality (FIG. 3) and therefore this sequence was chosen to generate an immunizing peptide. The sequence includes a Cys-Cys bond that generates a three-dimensional epitope. To retain that bond, an additional Lys was added to the synthetic peptide for conjugation to an immunizing protein, in order to avoid the commercial techniques that use Cys residues for conjugation (FIG. 4). Subsequently, a Lys residue in the peptide had to be changed to Arg to maintain conformation and avoid incorrect conjugation. The sequence shown at the bottom of the figure is the final sequence of the immunizing peptide (FIG. 4). Therefore, a synthetic peptide was made that represented this conserved and necessary short sequence of 23 amino acids.

Antibodies against fibulin-3 are highly specific

Figure 5A:
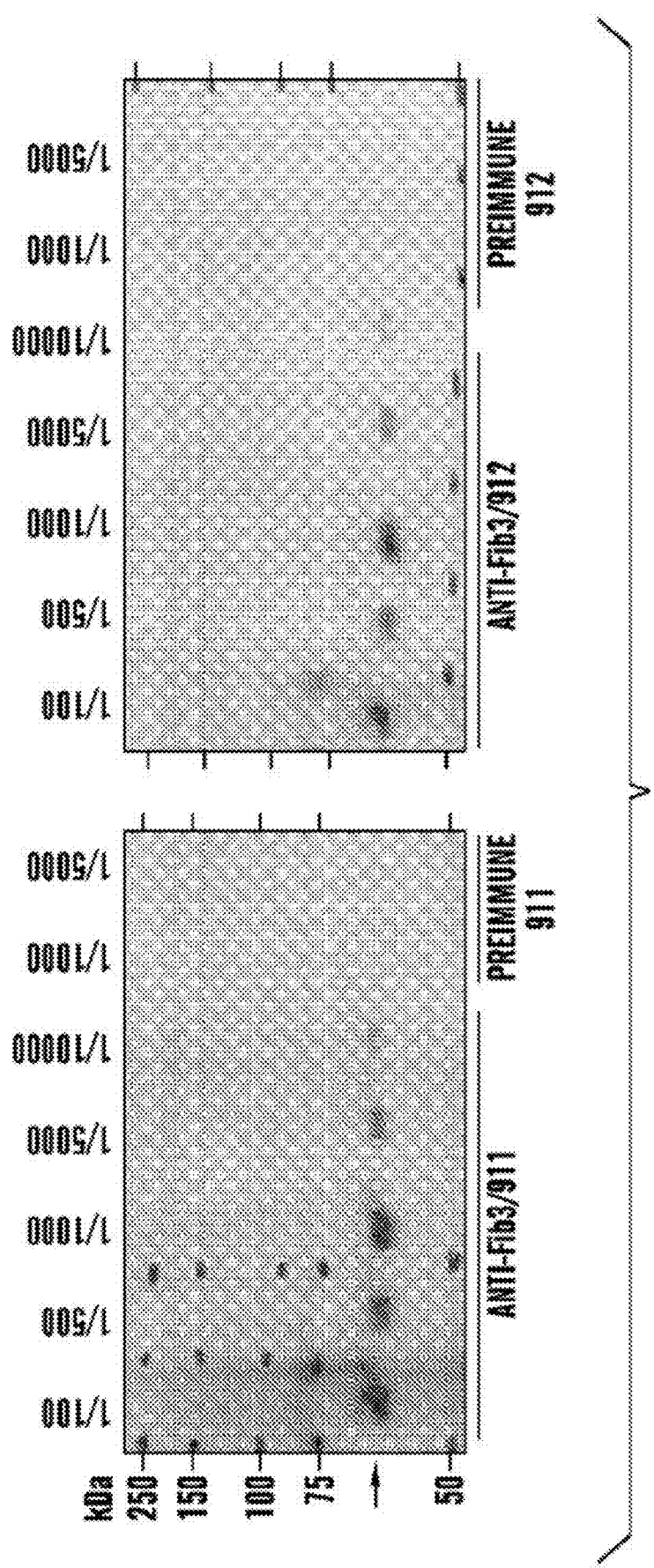
FIGS. 5A-5C show the validation of two polyclonal antibodies against fibulin-3. The peptide described in FIG. 4 was used to immunize two rabbits and obtain polyclonal antibodies against fibulin-3. The antibodies (anti-Fib3/911 and anti-Fib3/912) were affinity purified and dialyzed against PBS before use.
Figure 5B:
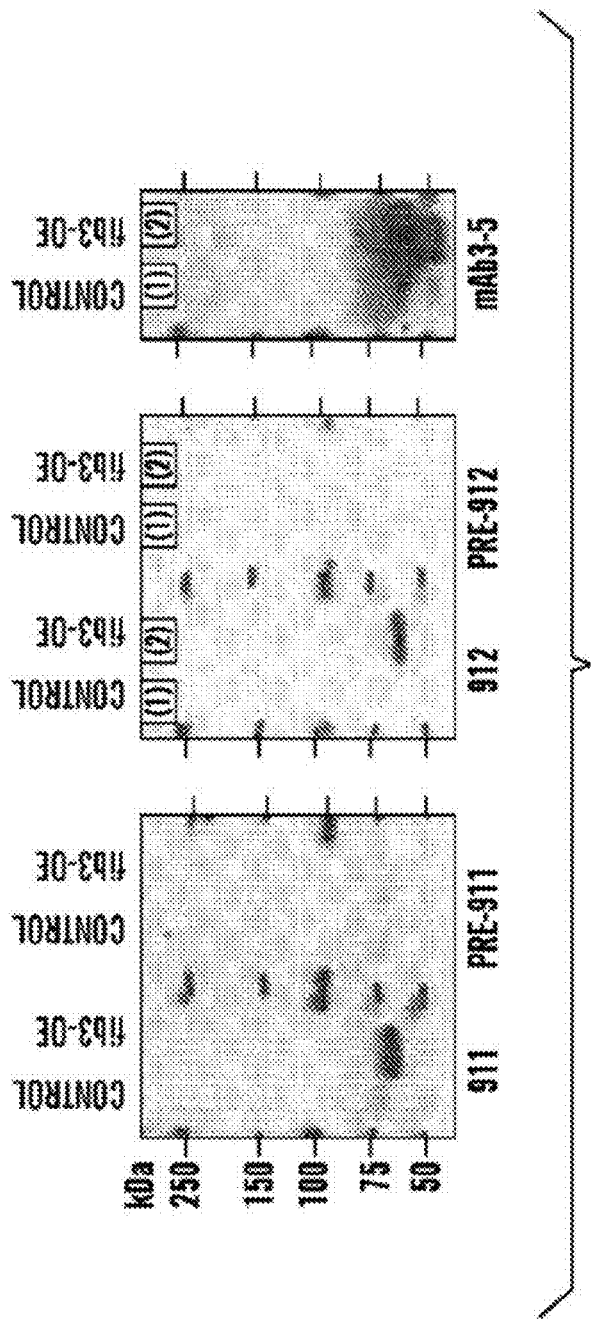
Figure 5C:
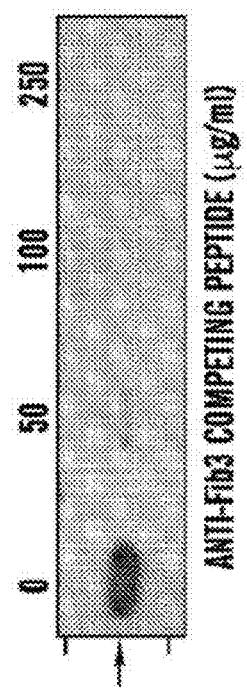

Two rabbit polyclonal antibodies were commissioned against the 23-amino acid peptide sequence of fibulin-3 involved in Notch activation. The peptide was minimally modified to facilitate the formation of a disulfide bridge necessary to form a conformational, tri-dimensional epitope (FIG. 4). Antibodies against fibulin-3 ("anti-Fib3/911" and "anti-Fib3/912") were purified by affinity chromatography, aliquoted, and prepared in phosphate-buffered saline (PBS) solution for all subsequent tests. Results with both antibodies demonstrated specific detection of purified fibulin-3 as well as fibulin-3 secreted by cultured glioma cells (FIGS. 5A-5B). Detection of fibulin-3 was lost when the antibodies were tested in presence of excess of the immunizing peptide, showing specificity of the antibodies by the target protein (FIG. 5C).

Antibodies against fibulin-3 induce cytotoxicity in a dose-dependent manner.

Figure 6:
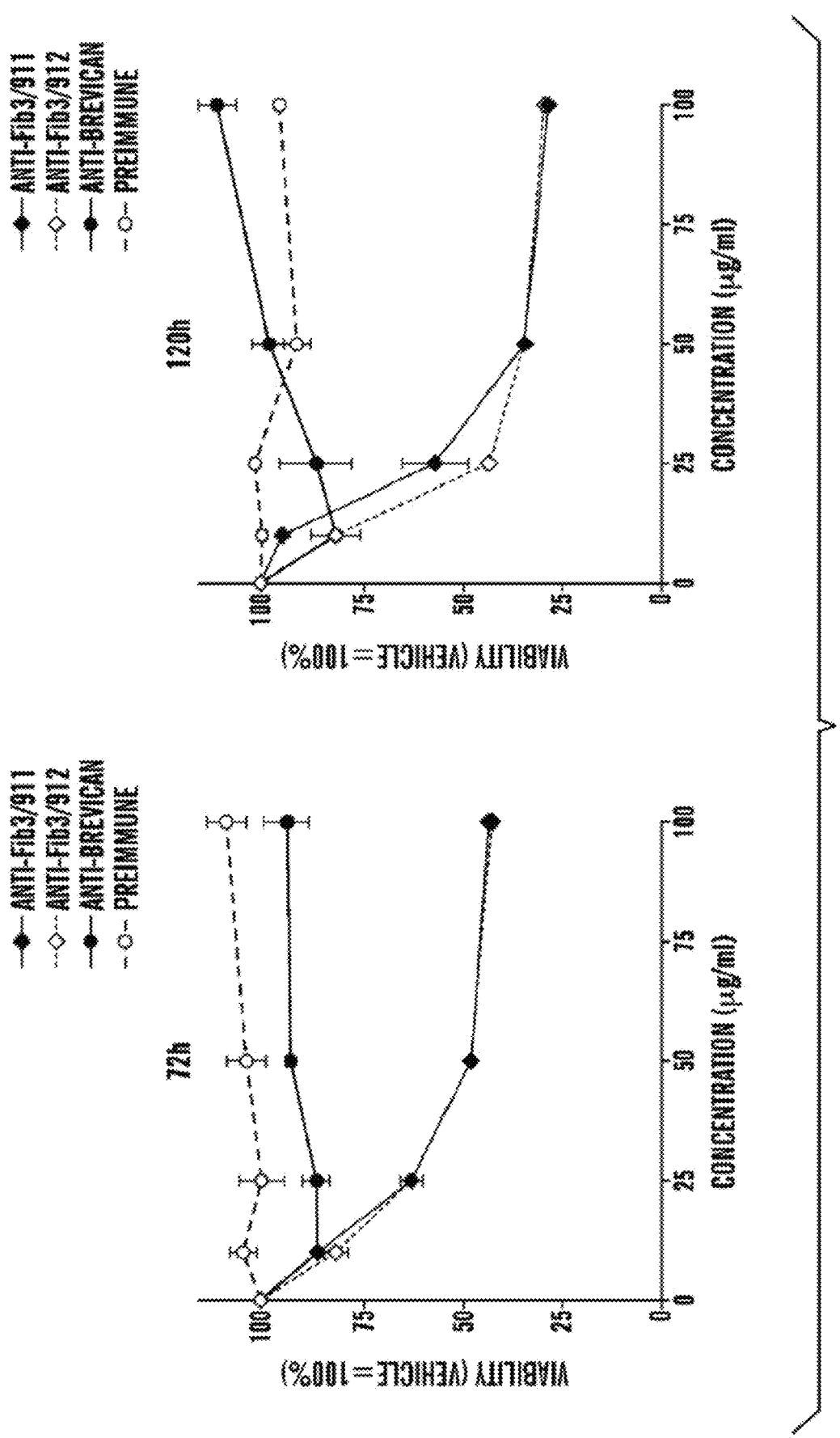
FIG. 6 shows that anti-fibulin-3 antibodies induce dose-response cytotoxicity in glioma cells. Glioma cells U251 MG (10,000 cells per well in 200 µl medium) were cultured in presence of anti-fibulin-3 antibodies or the preimmune serum from one of the rabbits. Cell viability was analyzed 72 h and 120 h after adding the antibodies, using a commercial reagent to measure cell reductive metabolism (CellTiter-96®, Promega). Both anti-Fib3/911 and anti-Fib3/912 induced significant cytotoxicity, with an $IC_{50}$ of 25-30 µg/mL. The preimmune serum had no effects at concentrations up to 100 µg/mL (shown in the graph) and up to 500 µg/mL (not shown). An antibody against the core of another extracellular protein secreted by glioma cells (anti-brevican), tested at the same concentrations, was also unable to affect cell viability.

Both anti-fibulin-3 antibodies were added to cultured glioma cells (U251MG cell line), followed by analysis of cell viability after 72 and 120 h. The pre-immune serum of anti-Fib3/911 was also used as a control. Results from viability tests demonstrated that the anti-fibulin-3 antibodies significantly reduced glioma cell viability in a dose dependent manner, with an $IC_{50}$ of 25-30 µg/ml (FIG. 6). The pre-immune serum showed no effects in the same culture conditions (even at concentrations up to 500 ug/ml, not shown in the graphs). As an additional control, a polyclonal antibody against a different extracellular protein (anti-brevican) was used in the same conditions, and also failed to show any significant effects on cell viability.

Figure 7:
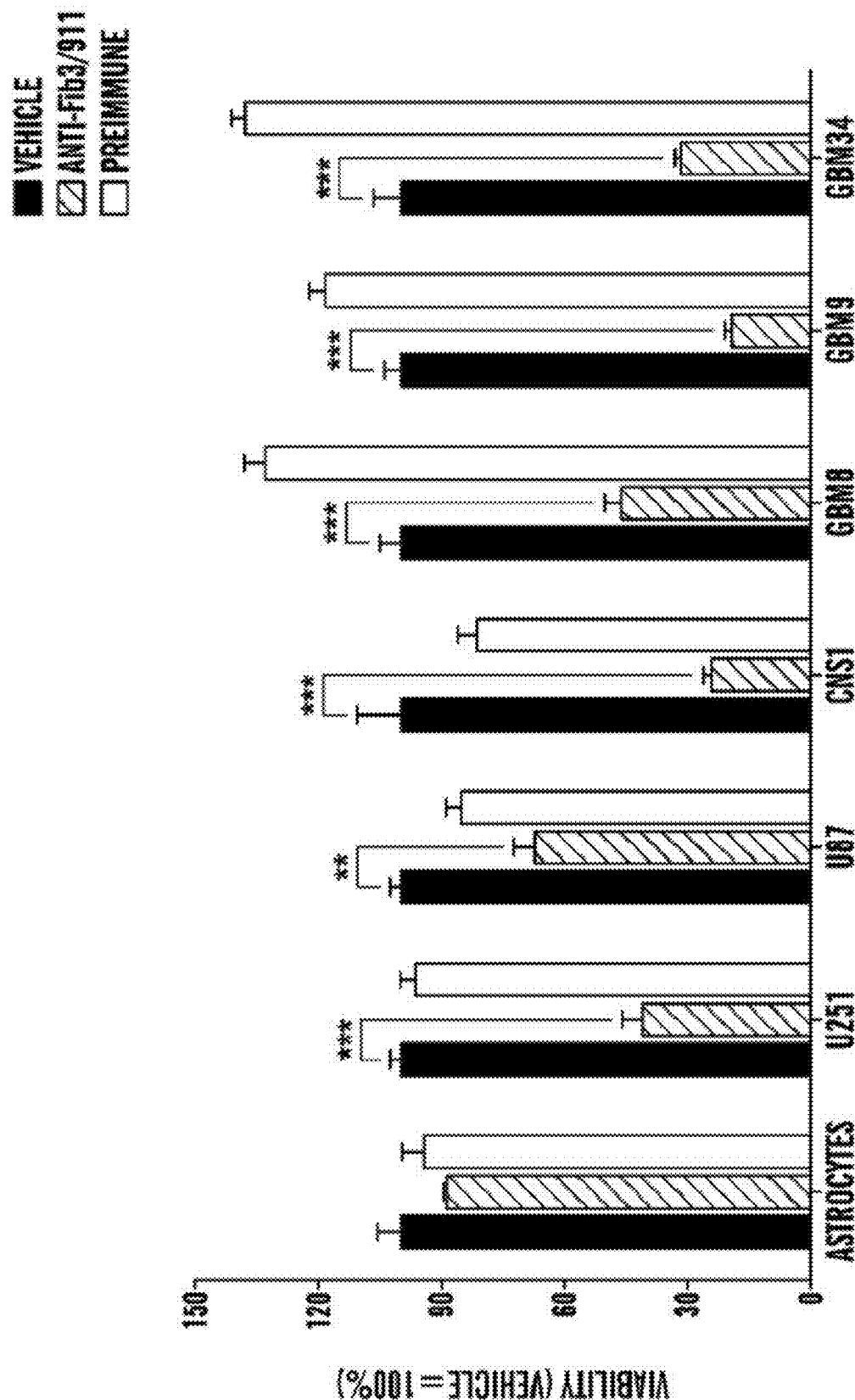
FIG. 7 shows that anti-fibulin-3 antibody is cytotoxic against glioma cells but not against normal neural cells. Normal human astrocytes and glioma cell lines (U251MG, U87MG and CNS1) were cultured as adherent cells in 96-well plates (10,000 cells/well). Three primary cultures of glioma-initiating cells (GBM8, GBM9 and GBM34) were cultured in suspension using appropriate medium in 96-well plates (25,000 cells/well). All cells were exposed to anti-Fib3/911 (50 µg/mL) or its pre-immune serum for 72 h, followed by measurement of cell viability as indicated in FIG. 5. All glioma cells exhibited significant cytotoxicity with anti-Fib3/911 but not with the pre-immune serum or vehicle (PBS). In contrast, normal astrocytes were not affected by the antibody ( $p<0.01$; * $p<0.001$, one-way ANOVA for each cell line)

Antibodies against fibulin-3 induce cytotoxicity in a wide range of glioma cells but not in normal cells. The antibody anti-Fib3/91 I was used for further tests because it showed stronger reactivity against fibulin-3. This antibody was added to cultures of different glioma cell lines (U251MG, U87MG, CNS1) as well as cultures of glioma initiating cells that produce large amounts of fibulin-3 (GBM8, GBM9, GBM34). The antibody was also added to a culture of normal human astrocytes, which do not produce fibulin-3 [9]. Vehicle control (PBS) and the pre-immune serum of anti-fibulin-3/91I were tested as controls. Cell viability was measured after 72 hours. The results indicate that anti-Fib3/911 was highly effective against all the glioma cells tested, but did not have any significant effects on normal neural cells (astrocytes). Neither the vehicle nor the pre-immune serum affected cell viability (FIG. 7).

Figure 8:
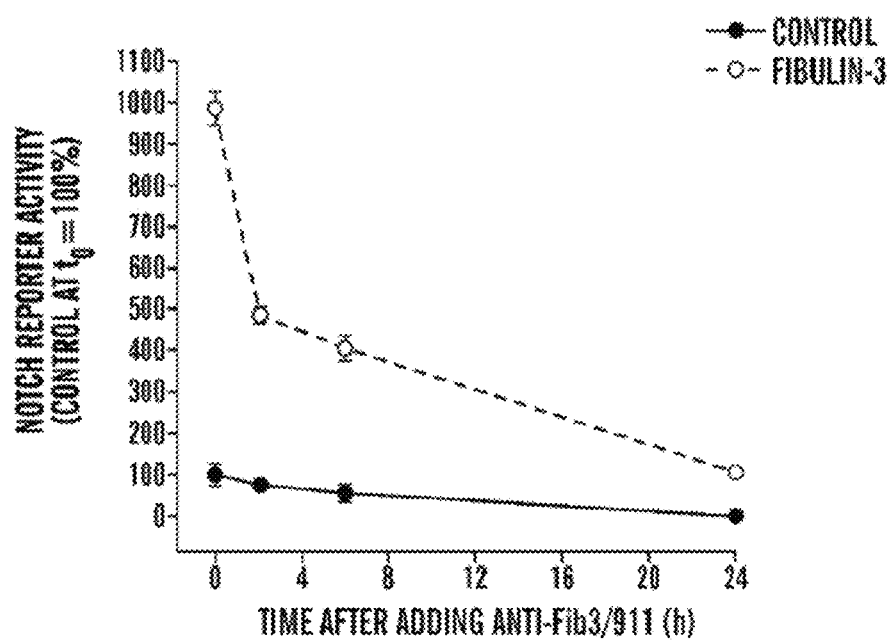
FIG. 8 shows that anti-fibulin-3 antibody blocks the molecular mechanism triggered by fibidin-3. Glioma cells (CNS I line) carrying a Notch-reporter luminescent system were transfected with fibulin-3 cDNA (or a control plasmid) and incubated in serum-free conditions for 24 h. The following day the antibody anti-Fib3/911 (50 µg/ml was added to the cultures and Notch activity was measured at different times. The results show that Notch activity was initially much higher in cells that had been transfected with fibulin-3 cDNA (white circles), as expected. However, this increased activity decayed by 50% after adding anti-fibulin-3 antibody for only 2 h, and reached control levels at 24 h after adding the antibody. Results after 24 h showed further decay of Notch activity in all cells (not shown) due to the cytotoxic effect of the antibody.

Antibodies against fibulin-3 block the molecular mechanism triggered by this protein. To confirm whether the cytotoxic effects were related to specific inhibition of the molecular mechanisms of fibulin-3, the antibody anti-Fib3/911 was added to glioma cells (CNS1 cell line) that had been transfected to overexpress fibulin-3. Overexpression of fibulin-3 in the glioma cells increased Notch signaling activity as expected. However, addition of anti-Fib3/911 to the cells rapidly blocked the effect of fibulin-3 on Notch signaling and eventually abolished activation of Notch (FIG. 8). These results confirmed that anti-Fib3/911 was a specific function-blocking antibody as envisioned.

Figure 9:
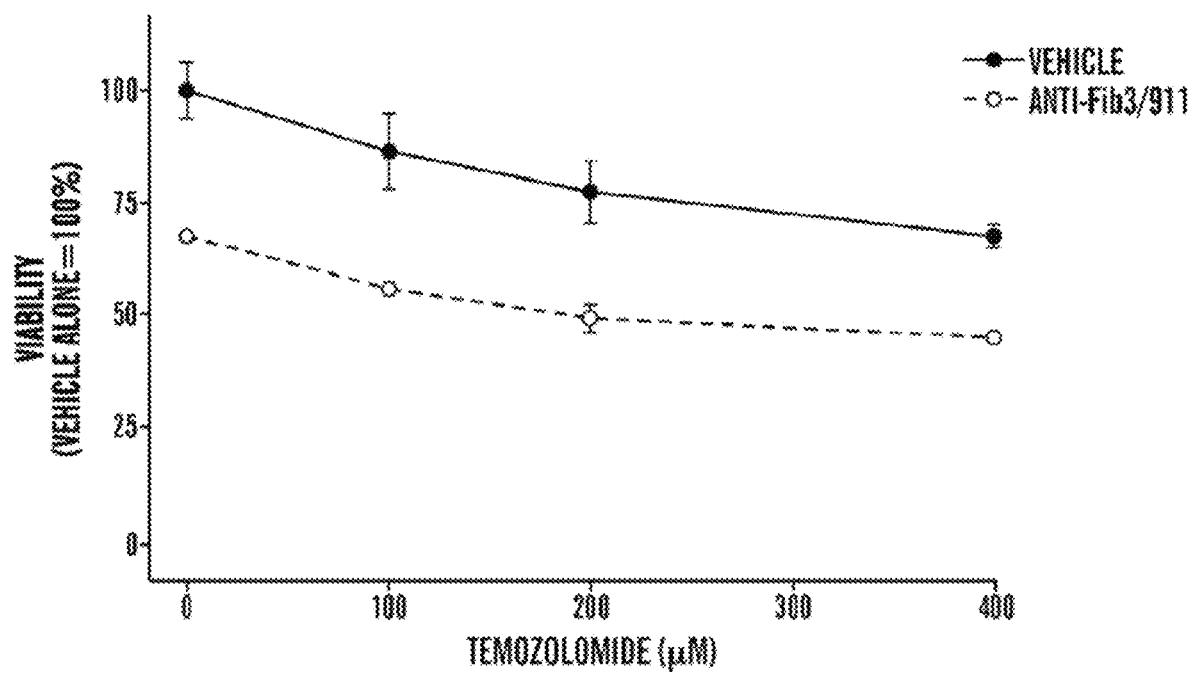
FIG. 9 shows that anti-fibulin-3 antibody potentiates the effect of a glioma chemotherapeutic. U251MG glioma cells were cultured in 96-well plates (10,000 cells/well) in presence of increasing concentrations of temozolomide (TMZ) alone (black circles) or combined with a fixed concentration of anti-Fib3/911 (50 µg/mL, white circles). Cell viability was measured after 72 h as indicated in FIG. 6. The results show that TMZ caused modest, dose-dependent cytoxic effect, which was significantly potentiated in presence of anti-Fib3/911. The antibody increased the cytotoxicity of TMZ by 30% in average.

Antibodies against fibulin-3 can potentiate the effect of a chemotherapeutic drug. Glioma cells (U251MG cell line) were cultured in presence of increasing doses of temozolomide, which is the standard-of-care drug for treatment of malignant glioma. The drug was combined with antibody vehicle (PBS) or with a fixed dose of anti-Fib3/911 antibody. Viability of the cells was analyzed after 72 h, which is a time period at which temozolomide has only a modest effect on glioma cells. Results showed that inclusion of anti-Fib3/911 had a significant potentiating effect on the cytotoxicity of temozolomide, increasing cell death by an additional 30% in average (FIG. 9).

Development and characterization of monoclonal antibodies against human fibulin-3. Following the initial development and characterization of rabbit polyclonal antibodies against human fibulin-3 (anti-Fib3/911 and anti-Fib3/912) the inventors have generated mouse monoclonal antibodies against the same peptide sequence originally used to generate the polyclonal antibodies (sequence TYTQCTDGYEWDPVRQQCRDIDE, SEQ ID NO:2). Mouse immunization, isolation of hybridomas, and purification of monoclonal antibodies were performed at DF/HCC Monoclonal Antibody Core. All validation procedures with antisera, clone supernatants, and purified antibodies were performed in the Viapiano and Chiocca laboratories at BWH/Department of Neurosurgery.

The inventors have developed and characterized the antibody mAb428.3C11 (mouse monoclonal IgG1 kappa subtype, full clone name: 428.2.3C11.H11.G3), which has high specificity for human fibulin-3 and blocks the functionality of this protein in glioblastoma cells. The purified antibody has been prepared in low-endotoxin conditions and validated as negative for a panel of mouse pathogens (MPV, LCMV, TMEV, SENDAI, MVM, MHV, ECTRO, REO and mycoplasma) in preparation for in vivo assays. The FIGS. 10-25 show the development and characterization of one embodiment of an anti-fibulin-3 monoclonal antibody, mAb428.3C11.

Figure 10:
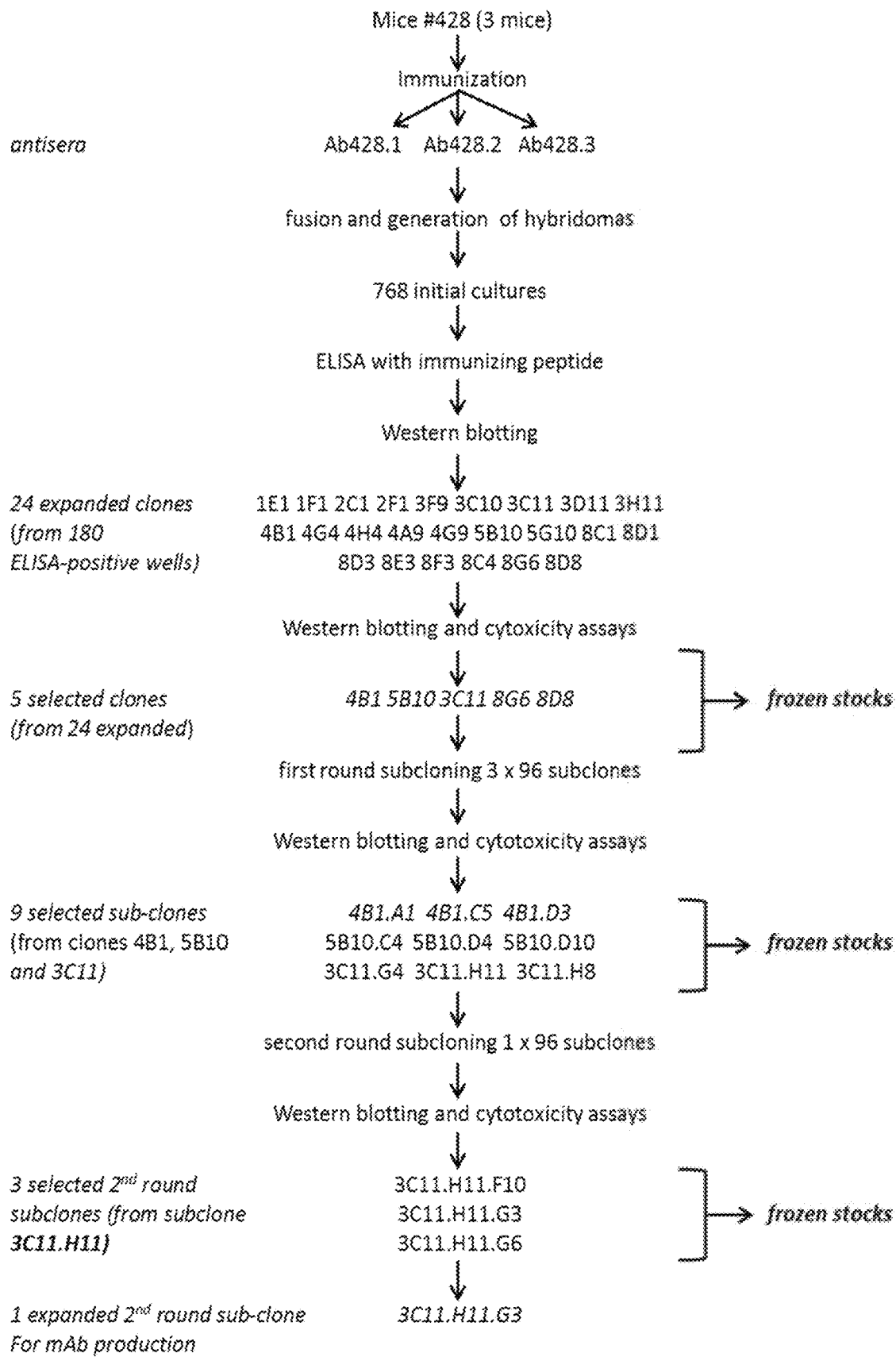
FIG. 10 shows the generation of anti-fibulin-3 monoclonal antibodies.

FIG. 10 shows the generation of anti-fibulin-3 monoclonal antibodies. This flow chart represents the strategy followed to isolate a highly specific monoclonal antibody against human fibulin-3. Mice were immunized with a synthetic peptide derived from fibulin-3 N-terminal domain (TYTQCTDGYEWDPVRQQCRDIDE) (SEQ ID NO:2). Western blotting of clone supernatants was performed against human fibulin-3 (200 ng/lane) prepared in non-reducing conditions. Cytotoxicity tests were performed by incubating U251MG glioma cells (10,000 cells/well) with dilutions of the clone supernatants and assessing cell viability after 48 h. The final clone selected after two rounds of subcloning was named mAb428.2.3C11.H11.G3 and shortened to "mAb428.3C11" or "mAb428.2."

FIG. 11 shows the detection of fibulin-3 by mAb428.3C11. Purified human fibulin-3 (200 ng/lane, ORIGENE) was subjected to SDS-PAGE in reducing and non-reducing conditions and probed with affinity-purified mAb428.3C11 (0.4 to 20 µg/ml, diluted in PBS from a 2 mg/ml stock). Results show high sensitivity of the antibody towards fibulin-3 and detection of the protein in reduced and non-reduced (multimeric) state.

FIG. 12 shows the kinetics of mAb428.3C11 binding to fibulin-3. Purified monoclonal antibody mAb428.3C11 was immobilized on a BIACORE™ flow chip and binding affinity to its antigen was quantified using purified human fibulin-3 pretreated with 10 mM DTT (to dissociate multimers). Experiments were performed in duplicate and fit to a 1:1 binding interaction model. Analysis of the binding curves suggests that the monoclonal antibody has a Kd value of approximately 4.5 nM for fibulin-3.

FIG. 13 shows the sequence of CDR regions of mAb428.3C11. Total RNA was extracted from the clone 428.2.3C11.H11.G3 and processed for sequencing of VH and VL regions following standard procedures with degenerate primers. Purified VH and VL gene products were separately cloned into pCR2.1 subcloning vector using TOPO cloning kit (LIFE TECHNOLOGIES). Cloned products were transfected into One-Shot TOP10 competent bacteriae and amplified. At least 5 colonies were screened for each cloned product and sequenced. The figure shows the amino acid and the nucleic acid sequences of the VH and VL chains, with highlighted complementary determining regions (CDRs). The sequences are SEQ ID NOS: 3-18.

The inventors were able to show that Fibulin-3 is detected in human glioma tissue but not in normal brain using the monoclonal antibodies generated. Frozen sections of human primary glioblastoma and normal adult human brain were fixed in ethanol/acetate buffer and processed for immunohistochemistry with the following anti-fibulin-3 antibodies: rabbit polyclonal anti-Fib3/911 (10 µg/ml), mouse monoclonal anti-fibulin-3 mAb428.3C11 (40 µg/ml), and a commercial mouse monoclonal antibody against human fibulin-3 (mAb3-5, 5 µg/ml, Santa Cruz Biotechnology). Specific staining of fibulin-3 in tumor tissue was detected whereas there was complete absence of staining in normal tissue (Data not shown). Both in-house generated antibodies show stronger staining in the tumor parenchyma compared to the commercial antibody. In all cases, staining is particularly intense around tumor blood vessels. These results highlight the specificity of mAb428.3C11 to detect native fibulin-3 in tumor tissue. Sections were counterstained to identify endothelial markers and cell nuclei by staining with with anti-CD31 and DAPI respectively. (Data not shown).

The inventors were also able to show that Fibulin-3 was detected in the perivascular location in glioblastoma tissue by immunostaining using the the monoclonal antibodies generated. Frozen sections of human primary glioblastoma were processed for immunohistochemistry as indicated in FIG. 5. Specific and striking fibrillar staining patterns of fibulin-3 were observed around tumor blood vessels (magnification: 40×). The antibody mAb428.3C11 detected the same fibrillar pattern observed with a commercial anti-fibulin-3 antibody. Endothelial cells were stained with anti-CD31 and cell nuclei with the dye DAPI. (Data not shown).

Figure 14:
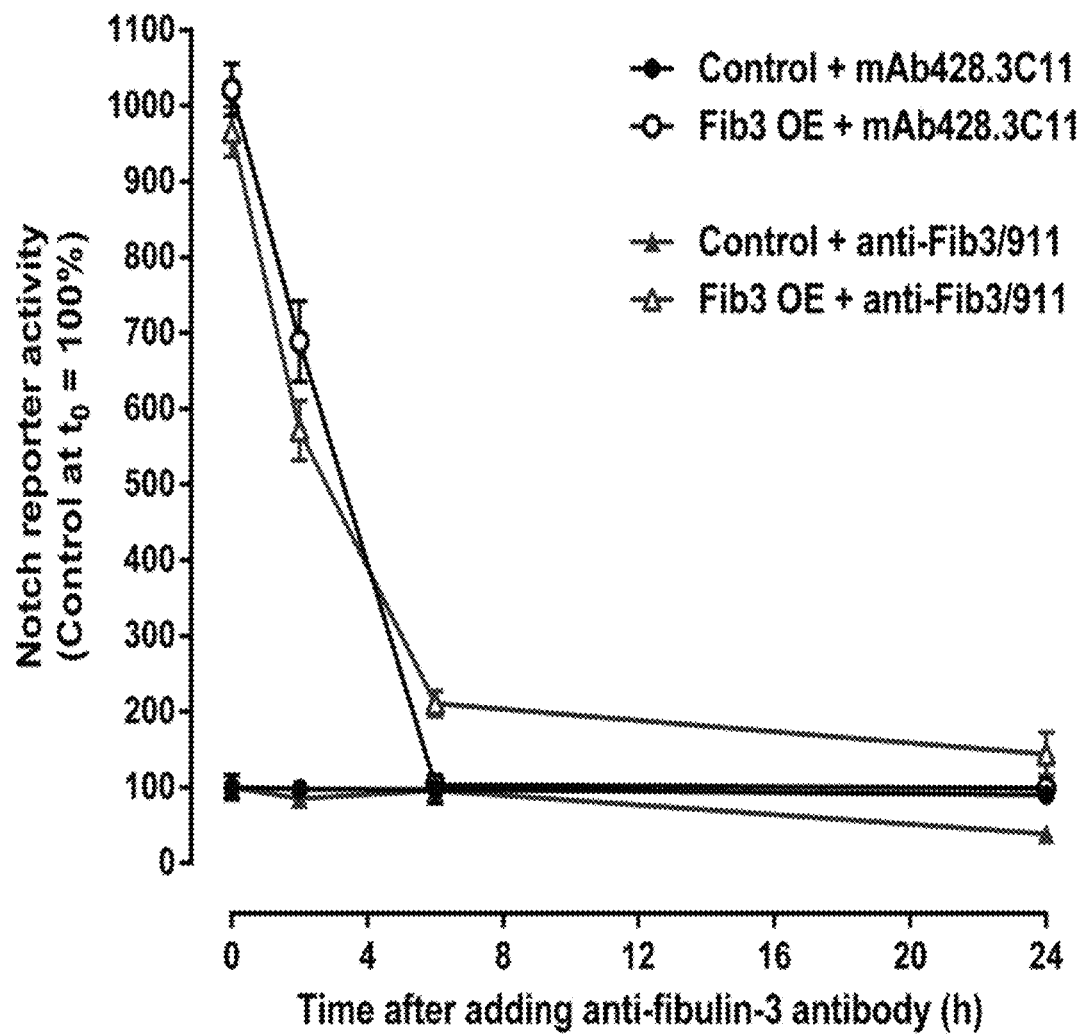
FIG. 14 shows that mAb428.3C11 blocks the molecular mechanism triggered by fibulin-3.

FIG. 14 shows that mAb428.3C11 blocks the molecular mechanism triggered by fibulin-3. Glioma cells (CNS1 line) carrying a Notch-driven luminescent reporter system were transfected with fibulin-3 cDNA (Fib3 OE) or a control plasmid (Control) and incubated in serum-free conditions for 24 h. The following day the antibodies anti-Fib3/911 (50 µg/ml) or mAb428.3C11 (100 µg/ml) were added to the cultures and Notch activity was measured after 0, 2, 6, and 24 h. Results show that the marked increase of Notch activity induced by fibulin-3 is blocked by both anti-fibulin-3 antibodies. Notice that at t=4 h the antibody mAb428.3C11 has completely abolished fibulin-3 effects on Notch activation while cells treated with anti-Fib3/911 still show considerable residual effect of fibulin-3. At t=24 h the levels of Notch activity in cells treated with mAbn428.3C11 are indistinguishable from controls while anti-Fib3/911 causes some decrease below baseline due to non-specific cytotoxic effects on the cells.

Figure 15:
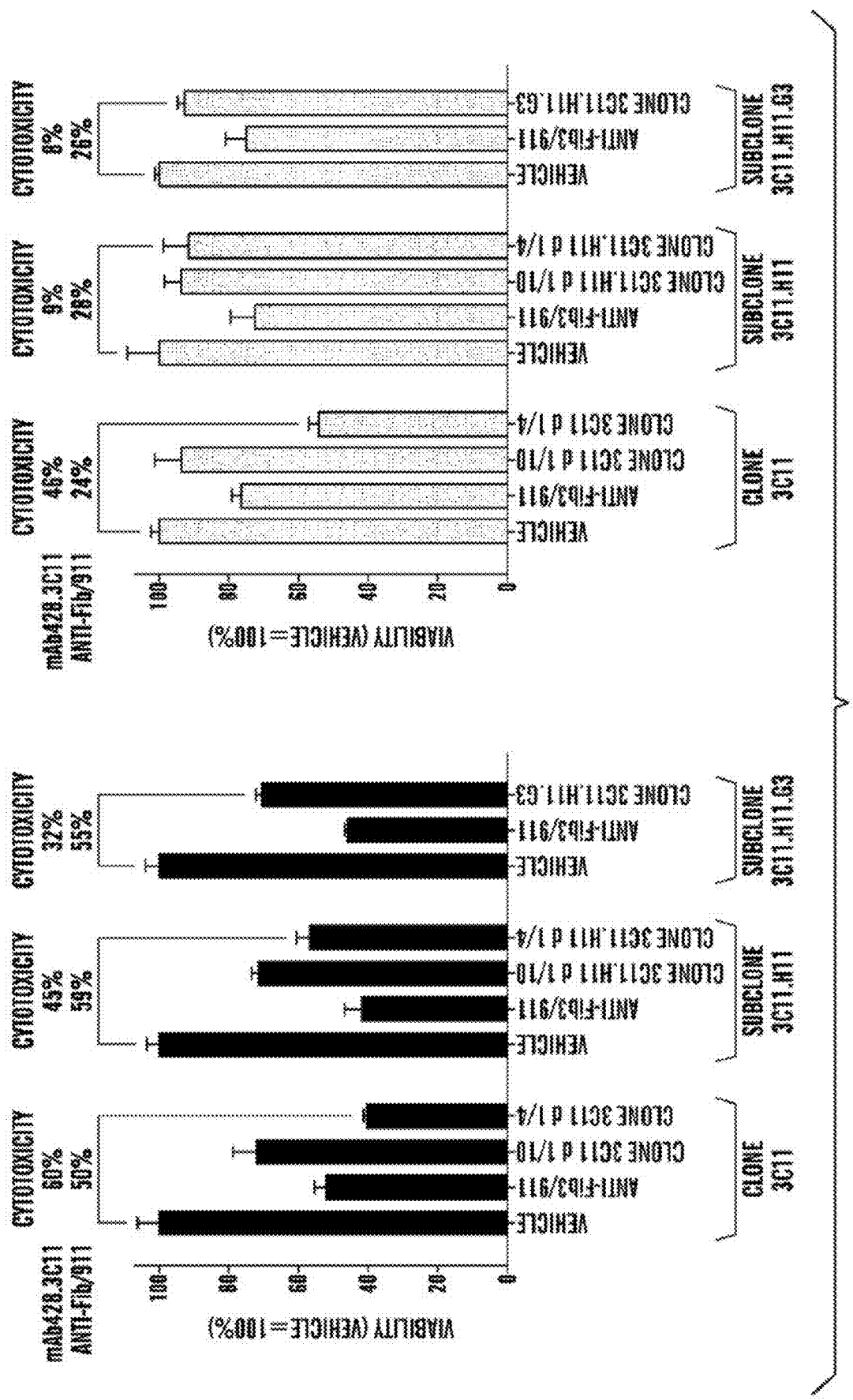
FIG. 15 shows that mAb428.3C11 is cytotoxic against glioma cells.

FIG. 15 shows that mAb428.3C11 is cytotoxic against glioma cells Human glioma cells (U251MG line) and control HEK293 cells (that do not express fibulin-3) were cultured in 96-well plates (10,000 cells/well) in presence of supernatants of the clones 428.3C11 and 428.3C11.H11 (at dilutions 1/4 and 1/10) as well as purified antibodies mAb428.3C11.H11.G3 (100 µg/ml) and anti-Fib3/911 (50 µg/ml). After 48 h cell viability was measured by a conventional redox (soluble MTS) assay. The figure shows average viability of the cells from experiments performed in triplicate. Results suggest that repeated rounds of subcloning reduced in part the cytotoxicity of mAb428.3C11 but it is still detectable and significant. At the same time, this antibody shows negligible toxicity against control cells compared to the polyclonal antibody. Vehicle: control medium or PBS.

Figure 16:
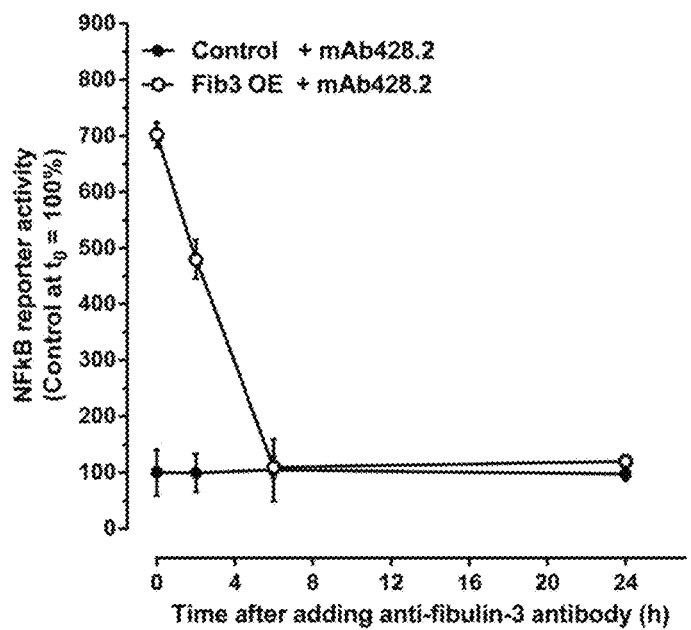
FIG. 16 shows that mAb428.2 inhibits NFkB signaling induced by fibulin-3 in glioma cells.

FIG. 16 shows the inhibitory effect of mAb428.2 on NFkB signaling induced by fibulin-3 in glioma cells. Glioma cells (U251 line) were transfected with a luminescent reporter plasmid driven by NF-kB signaling (pGL4.32 [luc2P/NF-κB-RE/Hygro], PROMEGA). Cells were co-transfected with plasmids carrying fibulin-3 cDNA (Fib3 OE) or a control cDNA (Control) and incubated in serum-free conditions for 24 h. The following day mAb428.2 (100 µg/ml) was added to the cultures and NFkB signaling activity was measured after 0, 2, 6, and 24 h. Results show a marked increase in NFkB signaling induced by fibulin-3 and the blocking of this effect caused by the monoclonal antibody.

Figure 17:
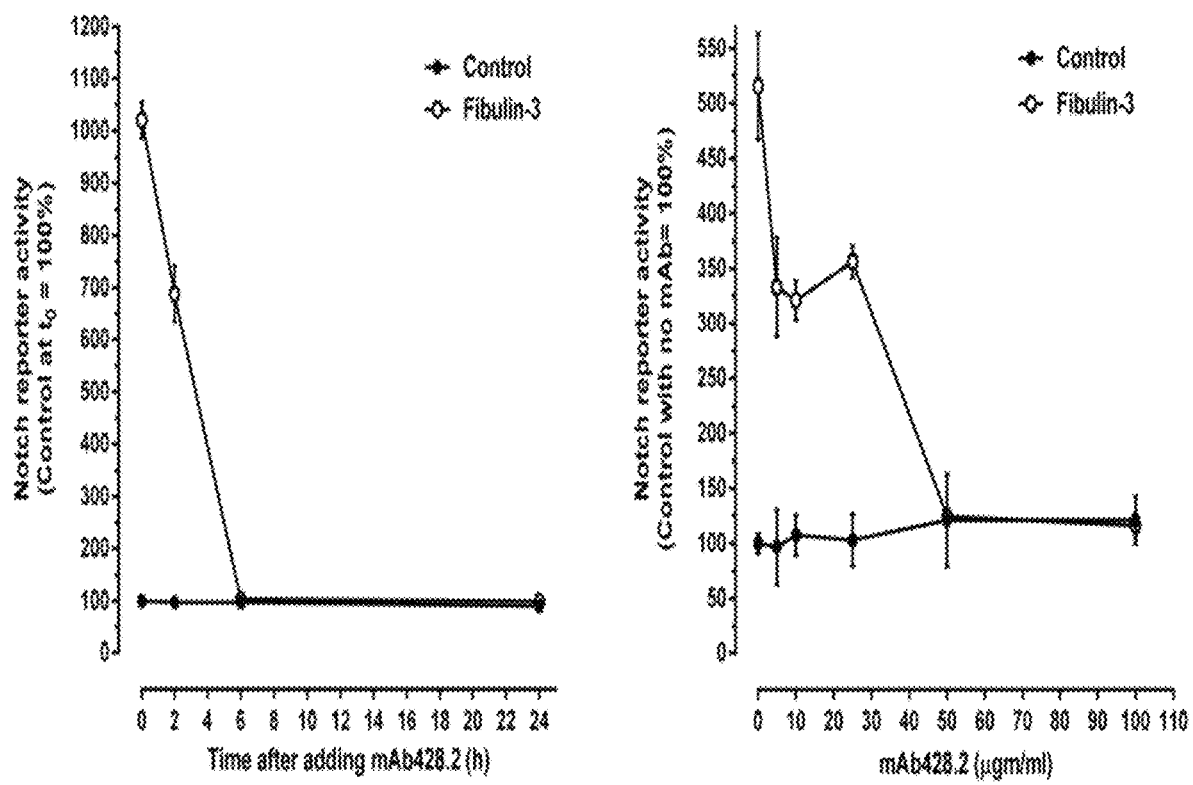
FIG. 17 shows that the inhibitory effect of mAb428.2 on fibulin-3-induced Notch signaling in glioma cells is concentration-dependent.

FIG. 17 shows the concentration-dependent effect of mAb428.2 against fibulin-3-induced Notch signaling in glioma cells. Glioma cells (CNS1 line) carrying a Notch-driven luminescent reporter system were transfected with fibulin-3 cDNA (Fib3 OE) or a control plasmid (Control) and incubated in serum-free conditions for 24 h. Results on the left panel show the effect of adding mAb428.2 (100 µg/ml), followed by measurement of Notch activity after 0, 2, 6, and 24 h. Results on the right panel show the effect of adding variable concentrations of mAb428.2 (0, 5, 10, 25, 50, and 100 µg/ml), followed by measurement of Notch activity after 6 h. In both cases, there were marked increase of Notch activity induced by fibulin-3 and the strong inhibitory effect of mAb428.2, which is time- and concentration-dependent. This indicates that the monoclonal antibody is specific for fibulin-3 expressed on glioma cells.

Figure 18:
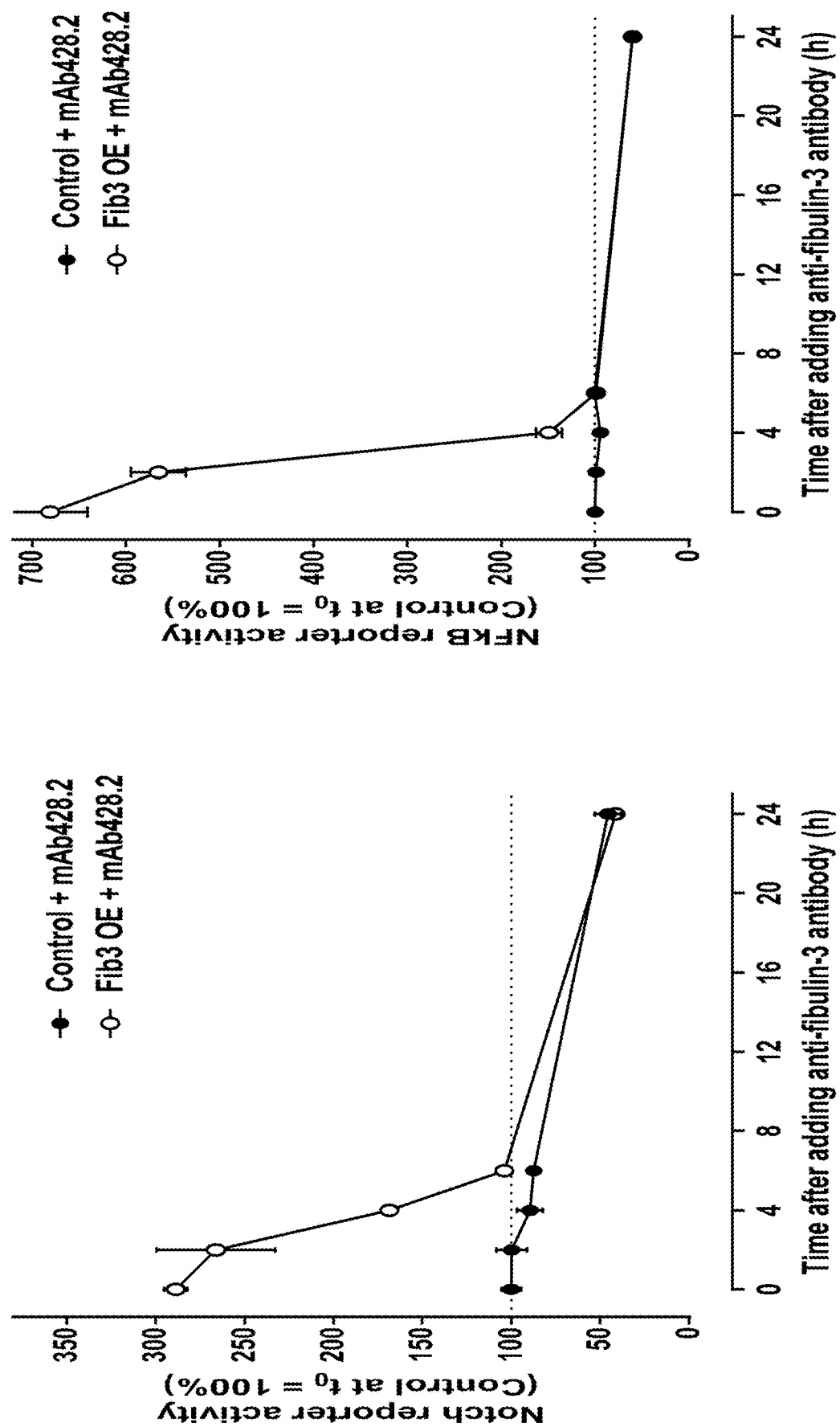
FIG. 18 shows that mAb428.2 inhibits Notch and NFkB signaling induced by fibulin-3 in retinal epithelial cells.

FIG. 18 shows the inhibitory effect of mAb428.2 on Notch and NFkB signaling induced by fibulin-3 in retinal epithelial cells Human retinal pigmented epithelial cells (ARPE19), which are used as in vitro model to study retinal degeneration, were transfected with luminescent reporter plasmids driven by Notch or NF-kB signaling as previously described in FIGS. 16 and 17.

Retinal degeneration is a condition associated by increased fibulin-3 activity. Fibulin-3 is one of the proteins that is consistently increased in retinal degeneration. Forced expression of fibulin-3 can induce the formation of retinal deposits that are a pre-requisite for retinal dystrophy (Marmorstein et al., Hum Mol Genet (2007) 16:2423-2432; Garland et al., Hum Mol Genet (2014) 23:52-68).

In addition, fibulin-3 has a mutant variant with a single aminoacid substitution (R345W) that is highly correlated with inherited forms of retinal dystrophy. Expression of this mutant fibulin-3 causes macular degeneration in transgenic models (Stone et al., Nature Genetics (1999) 22:199-202; Fu et al. Hum Mol. Genet (2007) 16:2411-2422).

Cells were co-transfected with plasmids carrying fibulin-3 cDNA (Fib3 OE) or a control cDNA (Control) and incubated in serum-free conditions for 24 h (FIG. 18). The following day mAb428.3C11 (100 µg/ml) was added to the cultures and Notch (left panel) or NF-kB (right panel) signaling activities were measured after 0, 2, 4, 6, and 24 h. Results show a marked increase in the activity of these reporters induced by fibulin-3 (as expected), followed by a strong blocking effect caused by the antibody. The inhibitory effect caused by the antibody on control reporter signaling (black dots) may have been caused by blocking of endogenous fibulin-3 that is highly expressed by ARPE19 cells.

FIGS. 19A-19B shows an embodiment of the generation of a semi-humanized mAb428.2. This experiment was performed to test feasibility of creating a recombinant antibody containing the original VL and VH sequences of mAb428.2 and demonstrate that this recombinant antibody still recognizes fibulin-3.

FIG. 19A shows the general schematic of subcloning the VL and VH sequences of mAb428.2 to generate chimeric humanized monoclonal anti-Fibulin-3 antibody. The VL and VH sequences of mAb428.2 were subcloned, respectively, into the custom plasmids pFuse-Light and pFuse-Heavy obtained from the Structural Genomics Consortium (Ontario, Canada). These plasmids are derived, respectively from pFUSE2ss-CLIg-mk and pFUSEss-CHIg-mG1 (INVIVOGEN™), and carry the cDNA to produce full-length light and heavy chains of chimeric human/mouse antibodies (Fab fragment is human and Fc fragment is from mouse). Plasmids carrying the resulting chimeric heavy and light chains were transfected into HEK293 cells. The cDNA and protein sequences of the chimeric heavy and light chains of the semi-humanized mAb428.2 are found in SEQ. ID. NOS: 19, 20, 23 and 24.

FIG. 19B shows the activity of the semi-humanized mAb428.2 as demonstrated by Western Blot analysis. Concentrated, serum-free culture medium from HEK293 cells (1 mg/ml total protein) was probed with anti-human IgG secondary antibody (HRP conjugate) to detect the chains of antibody in reducing and non-reducing conditions. C) Concentrated medium from HEK293 cells (1 mg/ml total protein) was directly used to probe purified human fibulin-3 (resolved by SDS-PAGE in non-reducing conditions). The chimeric antibody was detected with anti-human IgG secondary antibody. mAb428.2 (1 µg/ml) was used as positive control. Results show that non-purified, chimeric mouse/human mAb428.2 detects the same pattern of bands as purified mouse mAb428.2.

FIG. 20 summarizes the results of the cross-reactivity profile of mAb428.2 against healthy, normal, non-cancerous human tissues. Frozen sections (~5 µm thick) from a tissue microarray (Biochain #T6234700-5) were fixed for 20 minutes with buffered acidic alcohol (8.5 mM sodium acetate buffer, pH 5, in 90% ethanol) and processed for fluorescence immunohistochemistry with mAb428.2 (20 µg/ml) or a commercial anti-fibulin-3 antibody (mAb3-5, Santa Cruz Technology, 2 µg/ml). Antibodies were detected with ALEXA488-conjugated secondary antibodies. Tissue sections were treated with Sudan Black after staining but there was still considerable auto fluorescence arising from elastic fibers (collagen and elastin), melanin, and lipofuscin, all of which made detection of fibulin-3 difficult. The inventors therefore compared identical sequential sections stained with and without primary antibodies to determine the pattern of fibulin-3 detection by mAb428.2. Results were mostly negative for mAb428.2, indicating low cross-reactivity in normal tissues. The antibody detected fibulin-3 in the basement membrane of skin (intense staining) and a scant fibrillar pattern of this protein in the stroma of uterus (bright staining) and breast (weak staining).

Table 2 summarizes the results of acute toxicity assays for mAb428.2 injected intravenously (IV) into mice. A dose-escalation study was performed with athymic mice that received a single IV injection of mAb428.2 (purified in low-endotoxin conditions). Doses ranged from 0.1 to 30 mg/kg and mice were observed (and weighed) for periods ranging from 15 minutes to 14 days after injection. Mice were perfused with 4% paraformaldehyde and several organs were recovered, processed for histochemistry and analyzed by a specialist in rodent histopathology. Note that recovered organs and tissues for FFPE+H&E processing were: cerebrum, cerebellum, eyes, liver, kidney, skin, forepaws (to assess connective tissue). This study was performed independently at the Beth Israel Deaconess Medical Center Preclinical Murine Pharmacogenomics Core and tissues were evaluated at the Dana-Farber/Harvard Cancer Center Rodent Histopathology Core. Results showed no adverse effects after injection, no weight loss in the animals and no evidence of histopathology in tissues stained by H&E. The table summarizes the doses and post-injection periods (each row corresponds to one animal). This study showed that maximum tolerated dose before causing toxicity (MTD) was not achieved up to 30 mg/kg (for a single IV injection).

Detection of circulating mAb428.2 injected IV in naïve and tumor-bearing mice. The inventors then analyzed the in vivo circulation and detection of mAb428.2 after the antibody has been injected intravenously (IV) into mice.

To detect circulating antibody mAb428.2 and accumulation of this antibody in tumors, an aliquot of purified, low-endotoxin, mAb428.2 was labeled with the fluorochrome DyLight-755 (Thermo-Pierce #84538) and injected via tail-vein in mice at a dose of 2.5 mg/kg. Naïve and tumor-bearing animals were anesthetized at different times post-injection and placed in a fluorescence imaging system (IVIS Lumina III-LT) to detect fluorescence emitted by the antibody.

In naïve mice, results showed rapid accumulation of the fluorescence in the bladder (t=2 h) suggesting rapid entrance into circulation followed by clearance of the mAb (or its fluorochromes, due to breakdown). The antibody also accumulated more slowly in the liver (t>=6). In both cases, clearance occurred by t>=24 h. (Data not shown).

In mice bearing subcutaneous tumors, the antibody accumulated in the tumors by t=5 h post-injection and was still detectable with high intensity of fluorescence after 24 h. A control isotype antibody (mouse IgG1) prepared with the same fluorochrome showed much smaller accumulation in the tumor, indicating that the accumulation of mAb428.2 was specific. (Data not shown).

In mice bearing intracranial tumors, the antibody was only measured at t=5 h post-injection. The amount detected through the skull was very small but higher than the amount of a control IgG1 antibody. The antibody was not detected in significant amounts after 24 h. (Data not shown).

Importantly, the inventors did not detect accumulation of fluorescence in the skin or connective tissues at any time points, suggesting that mAb428.2 did not accumulate in these tissues even though they normally express fibulin-3.

Figure 21:
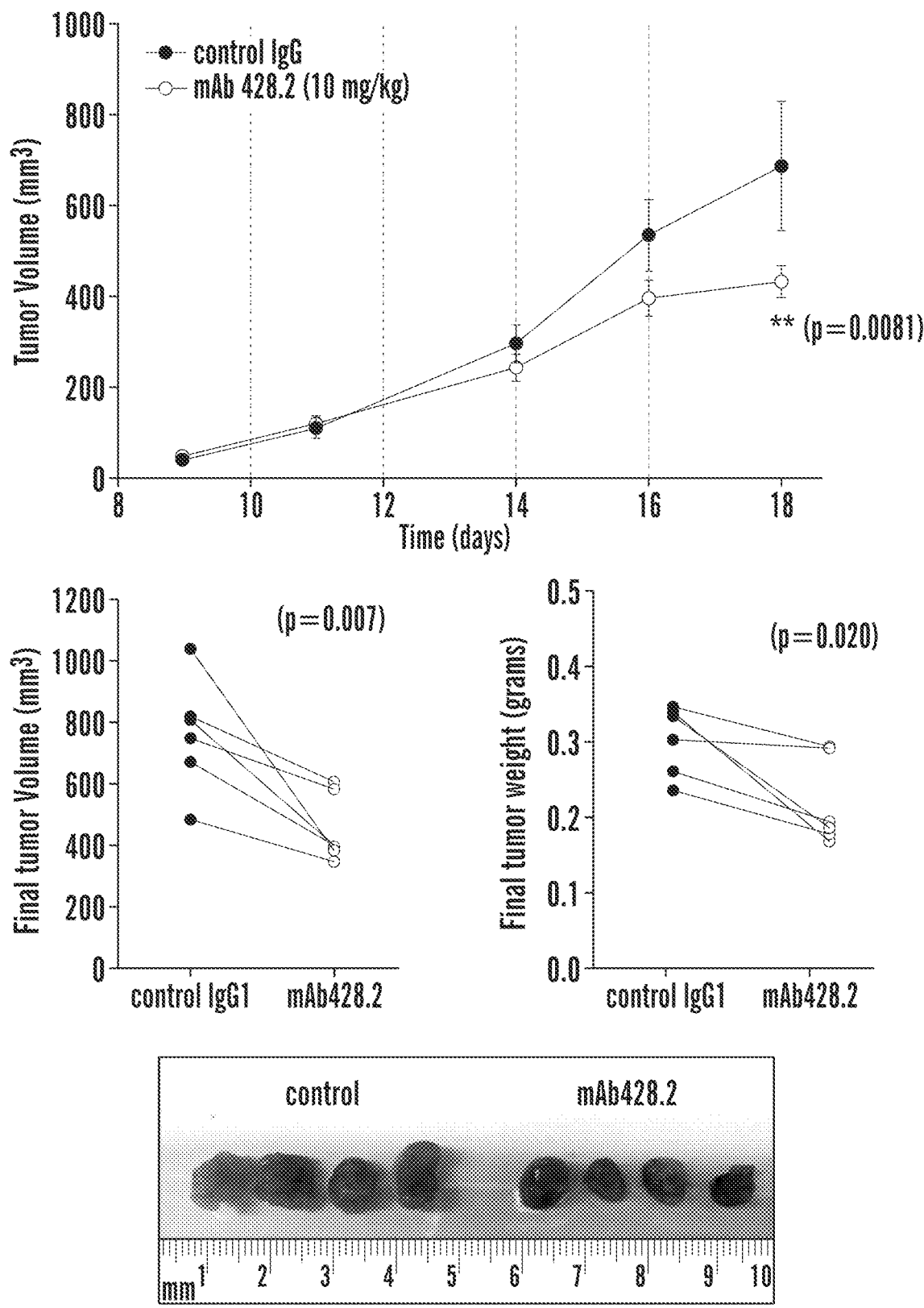
FIG. 21 shows the anti-glioma efficacy of mAb428.2 injected locally and directly into tumors (4 injections of 10 mg/kg each).

FIG. 21 shows the anti-glioma efficacy of mAb428.2 injected locally in the tumor (10 mg/kg). Athymic mice received sub-cutaneous (SQ) bilateral implants of GBM34 glioblastoma stem cells ($1\times10^6$ cells/50 µl). Tumors were allowed to grow until they reached a volume of 100 mm$^3$. Animals (N=5/group) were then injected with mAb428.2 (10 mg/kg) in the left-side tumor and non-immune mouse IgG1 in the right-side tumor, every two days (total: 4 injections). Mice were sacrificed when any of their tumors reached a length >18 mm. Results show the reduction in tumor volume and weight after treatment with mAb428.2 compared to control IgG1. Growth curves were analyzed by repeated-measures ANOVA and final parameters were compared by paired T-test.

Figure 22:
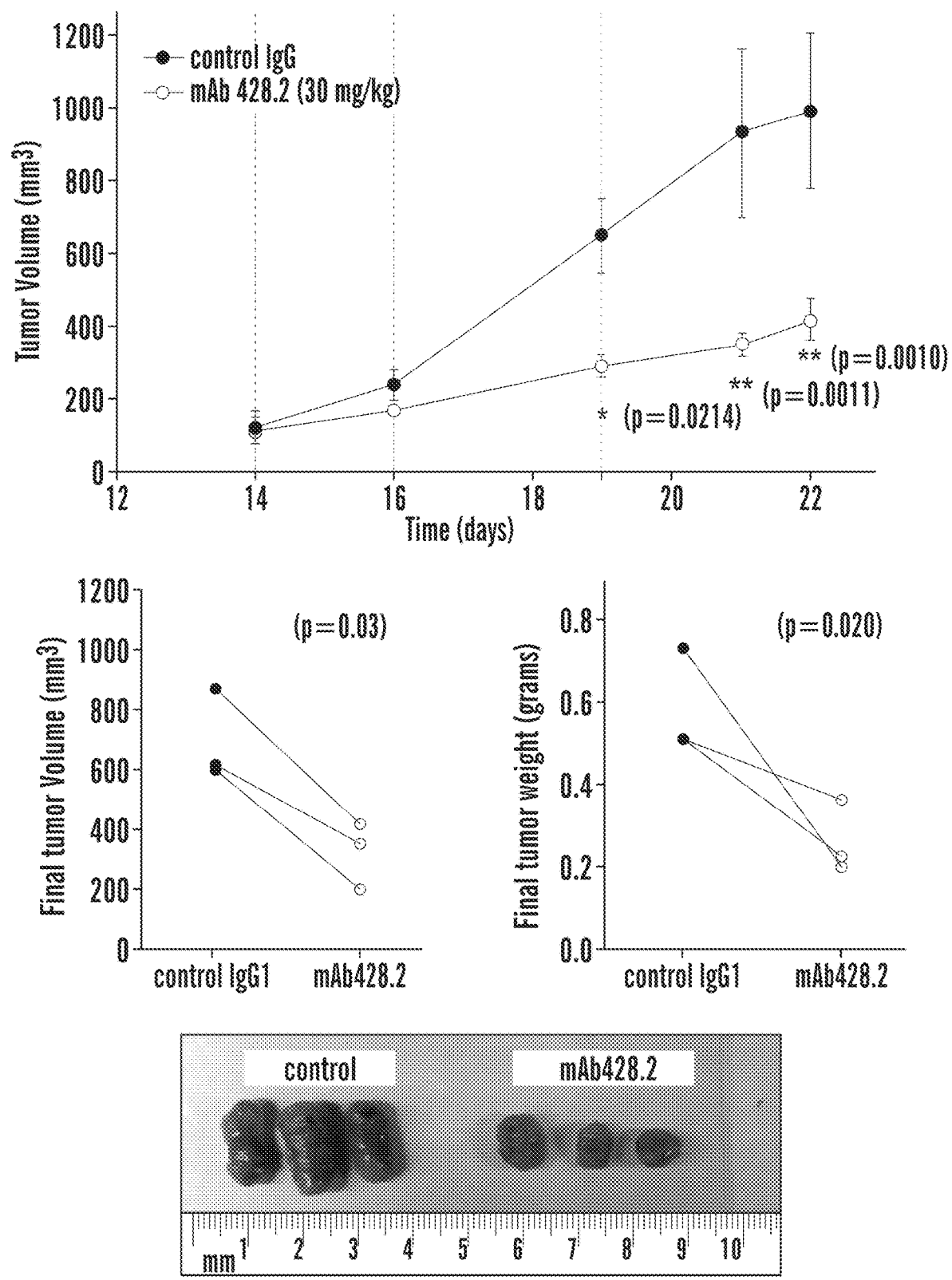
FIG. 22 shows the anti-glioma efficacy mAb428.2 injected locally and directly into tumors (3 injections of 30 mg/kg each).

FIG. 22 is another demonstration of the anti-glioma efficacy of mAb428.2 injected locally in the tumor (10 mg/kg). Athymic mice received SQ bilateral implants of GBM34 glioblastoma stem cells ($1 \times 10^6$ cells/50 µl). Tumors were allowed to grow until they reached a volume of 100 mm$^3$. Animals (N=3/group) were then injected with mAb428.3C11 (30 mg/kg) in the left-side tumor and non-immune mouse IgG1 in the right-side tumor, every two days (total: 3 injections). Mice were sacrificed when any of their tumors reached a length >=20 mm. Results show the reduction in tumor volume and weight after treatment with mAb428.2 compared to control IgG1. Growth curves were analyzed by repeated-measures ANOVA and final parameters were compared by paired T-test.

FIG. 23 shows the target-hit validation for mAb428.2 injected intratumorally. Tumors from FIG. 22 were collected after euthanasia, divided in pieces, and frozen at −80° C. Tumor homogenates were processed for SDS-PAGE and Western blotting with antibodies against molecules representative of the major pathways activated by fibulin-3 (i.e., Notch pathway and NF-kB pathway) (FIG. 23A). Notch activation was assessed by detecting expression of Notch intracellular cleaved domain (NICD) and the Notch-dependent gene Hes5. NF-kB activation was assessed by detecting expression of phosphor-p65 (NF-kB RelA) relative to total p65. Each lane represents one individual tumor. Values of integrated optical density (IOD) for all bands were normalized to tubulin levels (FIG. 23B). Normalized values for each target protein were compared by paired T-test (* $p<0.05$; ** $p<0.01$). Results show that repeated injection of mAb428.2 into the tumor caused significant inhibition of Notch and NF-kB pathways.

Figure 24:
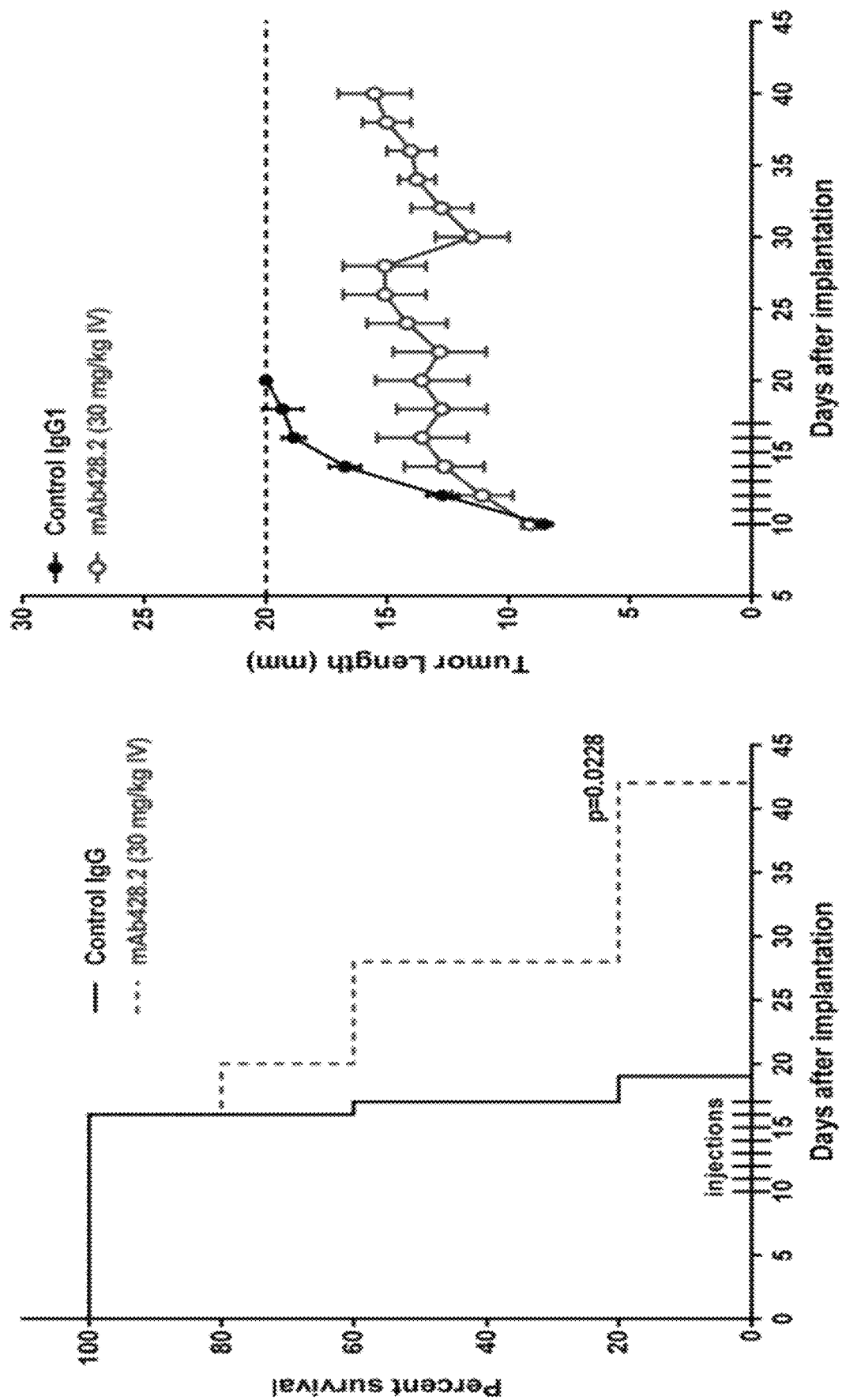
FIG. 24 demonstrates that in vivo administration of mAb428.2 to tumor-bearing mice prolongs overall survival of the mice.
Figure 25:
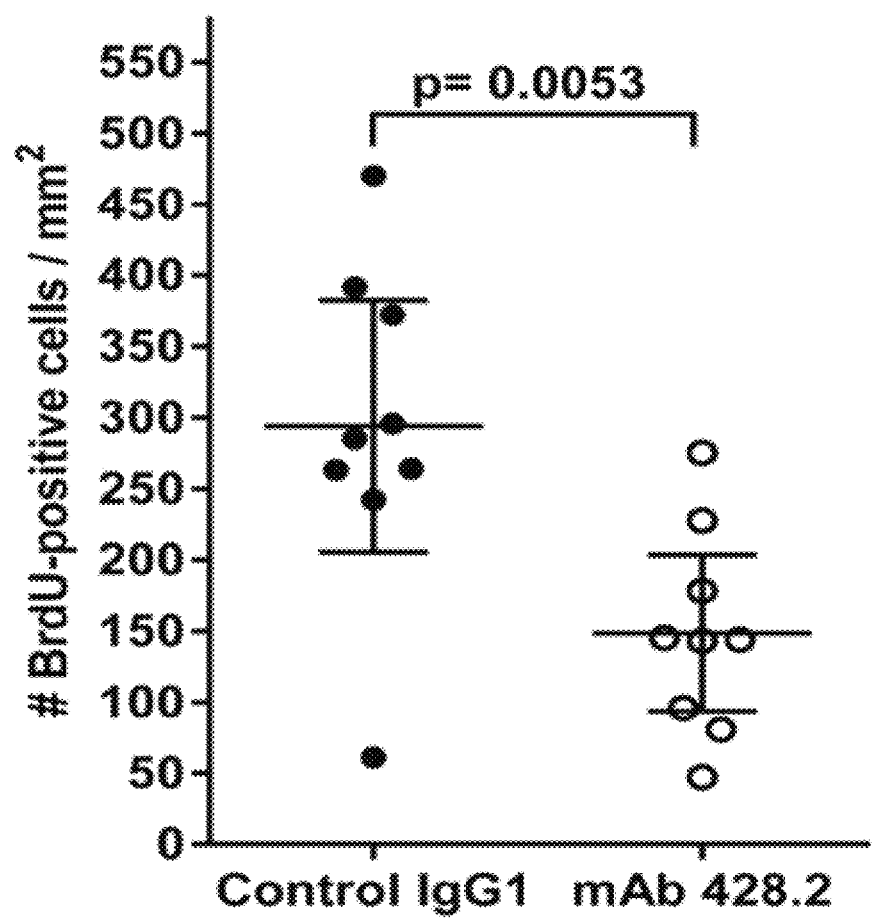
FIG. 25 demonstrates that in vivo administration of mAb428.2 to tumor-bearing mice produces tumor cytostatic effect of the tumors in these mice.

FIG. 24 shows the prolongation of overall survival in tumor-bearing mice injected with mAb428.2 intravenously. Athymic mice received SQ bilateral implants of GBM34 glioblastoma stem cells ($1 \times 10^6$ cells/50 µl). Tumors were allowed to grow until they reached a volume of 100 mm$^3$. Animals (N=5/group) were then injected with mAb428.2 (30 mg/kg) or non-immune mouse IgG1 every day, for a total of 8 days (total: 8 injections). Mice were monitored for tumor growth and sacrificed when any of their tumors reached a length >=20 mm. Long-term survivors (>40 days) in which length was not increasing above 20 mm were euthanized when tumors reached width >=15 mm or presented ulcerations. Results show the significant prolongation of overall survival in mice treated with mAb428.2 compared to control IgG1. Curves for overall survival were compared by long-rank test FIG. 25 shows the verification of tumor cytostatic effect of mAb428.2 injected intravenously. Control and tumor mice studied in FIG. 11 for overall survival (treated with antibody 8×30 mg/kg, IV) were injected with 5-bromo-2'-deoxyuridine (BrdU, 50 mg/kg, IP) 1 h before euthanasia. BrdU staining of actively dividing cells. Tumors from 3 mice per group were processed for immunohistochemistry to detect BrdU uptake, corresponding to actively dividing cells. Tissue sections were imaged by fluorescence microscopy and quantified blindly using ImageJ image analysis software. DAPI was used to stain cell nuclei. Results were expressed as number of BrdU-positive cells per unit of tumor area. Results show a significant decrease in tumor cell division of animals treated with mAb428.2, even after the treatment had ended. (Data not shown). This result indicates a strong cyotostatic effect of mAb428.2 in tumors in vivo.

FIG. 26 shows the generation of a single chain monoclonal antibody, scFv428.2, and the detection of this recombinant protein expressed in expression host cells. FIG. 26A shows the the cDNA sequences corresponding to mAb428.2 VL and VH were subcloned in the vector pcDNA-3 with a 15-aminoacid intervening linker sequence, -GGGGSGGGGSGGGGS- (SEQ. ID. NO: 28), also known as: (G4S)$_3$. The construct was tagged at the C-terminus with Myc-tag and 6× His-tag (SEQ ID NO: 27) sequences to facilitate detection and purification. The plasmid carrying scFv428.2 was stably transfected into HEK293 cells. FIG. 26B shows the results from Western blotting show the detection of scFv in the conditioned medium of HEK293 cells using anti-Myc and anti-His antibodies (10 µg total protein per lane). FIG. 26C shows the small-scale purification using cobalt-based affinity chromatography shows efficient retention and purification of scFv428.3C11. The figure shows the total protein load in the gel (amido black staining, top) and the enrichment in scFv product after affinity chromatography (Western blot, bottom). The lanes indicated in the figure are: input (concentrated conditioned medium from HEK293 cells); flowthrough (non-retained proteins); wash low salt (phosphate buffered saline, 150 mM NaCl); wash high salt (phosphate buffered saline, 500 mM NaCl); and eluate (phosphate buffered saline, 500 mM NaCl and 100 mM imidazole). All lanes contain the same total amount of protein (10 µg/lane).

In addition, the inventors have also generated a second variant of scFv428 been for expression in bacteriae. The bacterial version has the same protein sequence but the signal peptide has been replaced with a pelB leader peptide to facilitate accumulation of soluble scFv in the periplasmic space of bacterial cells. The full coding sequences of scFv that can be expressed in eukaryotic (HEK293) and prokaryotic (E. coli) cells are SEQ. ID. NOS: 21 and 22. The protein sequences of scFv428 optimized for eukaryotic (HEK293) and prokaryotic (E. coli) expression are found in SEQ. ID. NOS: 25 and 26.

FIG. 27 shows the detection of fibulin-3 by scFv428.2 and cytotoxic effect of scFv428.2 in vitro.

In FIG. 27A, the conditioned medium from HEK293 cells expressing scFv428.2 (1 mg/ml, containing non-purified scFv428.2) was used to detect purified fibulin-3. The scFv construct was subsequently detected with anti-His antibody. The antibody mAb428.2 (1 µg/ml) was used as positive control. A separate control was an "inverted scFv" construct where the VL and VH domains of scFv428.2 were swapped (from VL-linker-VH to VH-linker-VL). Results show that scFv428.2 can detect denatured fibulin in reducing and non-reducing conditions. In FIG. 27B, purified, non-reduced, human fibulin-3 was dot-blotted on nitrocellulose and probed with scFv428.2 (conditioned medium from HEK293 cells, 1 mg/ml) or purified mAb428.2 (1 µg/ml). Both reagents were able to detect native fibulin-3 by dot-blotting. In FIG. 27C, U251 glioblastoma cells (5,000 cells/well) were incubated in conditioned medium from control-HEK293 or scFv-expressing HEK293 (1.5 mg/ml total protein). After 48 h cell viability was measured using the CellTiter-Glo kit to measure ATP production (PROMEGA cat #G7572). Results show that medium containing scFv428.2 caused approximately 50% decrease in viability of U251 cells (** $p<0.01$ by Student's t-test).

The references cited herein and throughout the specification are incorporated herein by reference.

REFERENCES

1. Argraves, W. S., et al. Fibulins: physiological and disease perspectives. *EMBO Rep.* 2003, 4, 1127-1131.
2. Obaya, A. J., et al. The dual role of fibulins in tumorigenesis. *Cancer Lett* 2012, 325, 132-138.
3. Gallagher, W. M., et al. Fibulins and cancer: friend or foe? *Trends Mol. Med.* 2005, 11, 336-340.
4. McLaughlin, P. J., et al. Lack of fibulin-3 causes early aging and herniation, but not macular degeneration in mice. *Hum. Mol. Genet.* 2007, 16, 3059-3070.
5. Rahn, D. D., et al. Failure of pelvic organ support in mice deficient in fibulin-3. *The American journal of pathology* 2009, 174, 206-215.
6. Marmorstein, L. Association of EFEMP1 with malattia leventinese and age-related macular degeneration: a mini-review. *Ophthalmic Genet.* 2004, 25, 219-226.
7. Marmorstein, L. Y., et al. Aberrant accumulation of EFEMP1 underlies drusen formation in Malattia Leventinese and age-related macular degeneration. *Proc. Natl. Acad. Sci. U.S.A* 2002, 99, 13067-13072.
8. Albig, A. R., et al. Fibulins 3 and 5 antagonize tumor angiogenesis in vivo. *Cancer Res.* 2006, 66, 2621-2629.
9. Hu, B., et al. Fibulin-3 Is Uniquely Upregulated in Malignant Gliomas and Promotes Tumor Cell Motility and Invasion. *Mol. Cancer Res.* 2009, 7, 1756-1770.
10. Pass, H. I., et al. Fibulin-3 as a blood and effusion biomarker for pleural mesothelioma. *N Engl 1 Med* 2012, 367, 1417-1427.
11. Seeliger, H., et al. EFEMP1 expression promotes in vivo tumor growth in human pancreatic adenocarcinoma. *Mal Cancer Res* 2009, 7, 189-198.
12. Song, E. L., et al. EFEMP1 expression promotes angiogenesis and accelerates the growth of cervical cancer in vivo. *Gynecol Oncol* 2011, 121, 174-180.
13. Hu, B., et al. Fibulin-3 promotes glioma growth and resistance through a novel paracrine regulation of Notch signaling. *Cancer Res* 2012, 72, 3873-3885.
14. Dolecek, T A., et al. CBTRUS statistical report: primary brain and central nervous system tumors diagnosed in the United States in 2005-2009. *Neuro O=1*2012, 14 Sapp, 5, v1-49.

TABLE 1

Diseases where the protein fibulin-3 is upregulated and thought to play a role in etiology

| Disease | Major references or reviews |
| --- | --- |
| Retinal dystrophies (Age-related macular degeneration; Malattia levantinese; Doyne honeycomb retinal distropy) | Marmorstein L. *Opthalmic Genet* (2004) 25: 219-226<br>Lotery A. and Trump D. *Hum Genet* (2007) 122: 219-236<br>Marmorstein L. et al. *Hum Mol Genet* (2007) 16: 2423-2432<br>Wyatt M. et al. *PLoS One* (2013) 8: e68088 |
| Pterygium | Perez-Rico C. et al. *Am J Ophthalmol* (2011) 151: 44-52<br>Engelsvold D. et al. *Exp Eye Res* (2013) 115: 189-198 |
| Malignant brain tumors (gliomas) | Hu B. et al. *Mol Cancer Res* (2009) 7: 1756-1770<br>Hu B. et al. *Cancer Res* (2012) 72: 3873-3885<br>Hiddingh L. et al. *Oncotarget* (2014) 5: 363-374 |
| Pancreatic carcinoma and adenocarcinoma | Seeliger H. et al. *Mol Cancer Res* (2009) 7: 189-198<br>Diersch S. et al. *Oncotarget* (2013) 4: 277-288 |
| Cervical carcinoma | En-lin S. et al. *Gynecol Oncol* (2010) 117: 417-422<br>Song E. et al. *Gynecol Oncol* (2011) 121: 174-180 |
| Nasopharyngeal carcinoma | Hwang C. et al. *J Pathol* (2010) 222: 367-379 |
| Mesothelioma | Pass H. et al. *N Engl J Med* (2012) 367: 1417-1427<br>Creaney J. et al. *Thorax* (2014) 69: 895-902 |
| Ovarian carcinoma | Chen J. et al. *PLoS One* (2013) 8: e78783 |
| Oestheoarthritis | Henrotin Y. et al. *Arthritis Rheum* (2012) 64: 2260-2267 |

TABLE 2

Summary of acute toxicity assays for mAb428.2 injected intravenously (IV) into mice.

| mAb428 dose | Endpoint | Pre-inject weight | Average | Stdev | Endpoint weight | Average | Stdev |
| --- | --- | --- | --- | --- | --- | --- | --- |
| vehicle | 14 days | 27.20 | 26.35 | 1.20 | 28.20 | 27.05 | 1.63 |
| vehicle | 14 days | 25.50 | | | 25.90 | | |
| 0.1 mg/kg | 15 min | 19.7 (*) | 23.95 | 3.32 | 22.40 | 24.27 | 1.67 |
| 0.1 mg/kg | 15 min | 21.60 | | | 24.80 | | |
| 0.1 mg/kg | 15 min | 26.30 | | | 25.60 | | |
| 1 mg/kg | 15 min | 25.30 | 24.77 | 0.47 | 25.20 | 24.40 | 0.69 |
| 1 mg/kg | 15 min | 24.60 | | | 24.00 | | |
| 1 mg/kg | 15 min | 24.40 | | | 24.00 | | |
| 10 mg/kg | 15 min | 23.60 | 23.60 | 0.40 | 23.50 | 23.60 | 0.75 |
| 10 mg/kg | 15 min | 23.20 | | | 22.90 | | |
| 10 mg/kg | 15 min | 24.00 | | | 24.40 | | |
| 0.1 mg/kg | 24 h | 25.10 | 24.93 | 1.46 | 25.40 | 25.27 | 1.31 |
| 0.1 mg/kg | 24 h | 26.30 | | | 26.50 | | |
| 0.1 mg/kg | 24 h | 23.40 | | | 23.90 | | |
| 1 mg/kg | 24 h | 25.80 | 26.13 | 0.49 | 25.80 | 26.30 | 0.50 |
| 1 mg/kg | 24 h | 25.90 | | | 26.30 | | |
| 1 mg/kg | 24 h | 26.70 | | | 26.80 | | |
| 10 mg/kg | 24 h | 26.20 | 26.00 | 0.92 | 26.30 | 26.47 | 0.96 |
| 10 mg/kg | 24 h | 25.00 | | | 25.60 | | |

TABLE 2-continued

Summary of acute toxicity assays for mAb428.2 injected intravenously (IV) into mice.

| mAb428 dose | Endpoint | Pre-inject weight | Average | Stdev | Endpoint weight | Average | Stdev |
|---|---|---|---|---|---|---|---|
| 10 mg/kg | 24 h | 26.80 | | | 27.50 | | |
| 30 mg/kg | 24 h | 27.40 | 26.20 | 1.15 | 27.40 | 26.40 | 0.95 |
| 30 mg/kg | 24 h | 26.10 | | | 26.30 | | |
| 30 mg/kg | 24 h | 25.10 | | | 25.50 | | |
| 0.1 mg/kg | 4 days | 25.10 | 24.93 | 0.15 | 25.20 | 24.53 | 0.61 |
| 0.1 mg/kg | 4 days | 24.80 | | | 24.00 | | |
| 0.1 mg/kg | 4 days | 24.90 | | | 24.40 | | |
| 1 mg/kg | 4 days | 25.30 | 24.23 | 1.29 | 25.00 | 23.93 | 1.10 |
| 1 mg/kg | 4 days | 22.80 | | | 22.80 | | |
| 1 mg/kg | 4 days | 24.60 | | | 24.00 | | |
| 10 mg/kg | 4 days | 24.70 | 24.03 | 0.65 | 24.70 | 24.00 | 0.61 |
| 10 mg/kg | 4 days | 24.00 | | | 23.60 | | |
| 10 mg/kg | 4 days | 23.40 | | | 23.70 | | |
| 30 mg/kg | 4 days | 24.00 | 23.73 | 1.72 | 25.20 | 24.70 | 1.90 |
| 30 mg/kg | 4 days | 25.30 | | | 26.30 | | |
| 30 mg/kg | 4 days | 21.90 | | | 22.60 | | |
| 0.1 mg/kg | 14 days | 24.10 | 22.40 | 3.48 | 25.20 | 23.93 | 1.94 |
| 0.1 mg/kg | 14 days | 24.70 | | | 24.90 | | |
| 0.1 mg/kg | 14 days | 18.40 | | | 21.70 | | |
| 1 mg/kg | 14 days | 24.60 | 24.30 | 0.44 | 24.60 | 24.37 | 0.32 |
| 1 mg/kg | 14 days | 23.80 | | | 24.00 | | |
| 1 mg/kg | 14 days | 24.50 | | | 24.50 | | |
| 10 mg/kg | 14 days | 24.60 | 24.90 | 0.70 | 25.10 | 25.30 | 0.62 |
| 10 mg/kg | 14 days | 24.40 | | | 24.80 | | |
| 10 mg/kg | 14 days | 25.70 | | | 26.00 | | |
| 30 mg/kg | 14 days | 24.20 | 22.90 | 1.47 | 25.50 | 23.70 | 1.80 |
| 30 mg/kg | 14 days | 23.20 | | | 23.70 | | |
| 30 mg/kg | 14 days | 21.30 | | | 21.90 | | |

(*) For mice sacrificed at t = 15 min the pre-injection weight was measured the day before injection.

TABLE 3

General Data Sheet on pFUSE-HEAVY Vector

| | |
|---|---|
| Source | Constructed by Peter Loppnau |
| Company | Structural Genomics Consortium, Toronto |
| Description | The pFUSE-HEAVY vector is a derivative of the pFUSEss-CHIg-mG1 vector (Invivogen). It is a mammalian expression vector for human/mouse hybrid IgG production and is used in a co-transfection with pFUSE-LIGHT. The expressed IgG is a hybrid human FAB from Library E or F, human hinge region, and a mouse Fc |
| Antibiotic resistance | Zeocin 25 ug/ml from 100 mg/ml stock solution |
| Promoter | hEF1-HTLV Promoter |
| Cloning Method | Insertion of DNA sequence into the cloning/expression region is preformed using BD-Biosciences Infusion enzyme mediated directional recombination between complementary 15 nucleotide DNA sequences at the ends of the insert (PCR product) and Afe1/Sph1 linearized vector. Insertion of target sequence involves replacement of SacB gene stuffer sequence, which provides for negative selection of the plasmid on 5% sucrose. |
| Initiation Codon | ATG in vector |
| N-terminal fusion sequence, IL2 signal peptide | MYRMQLLSCIALSLALVTNSEVQ---- (SEQ ID NO: 38) |
| C-terminal fusion sequence, identical to human FAB | ---LVTVSSASTKGPSVFPLAPSSKSTSGGTAALG CLVKDYFPEPVTVSWNSGALTSGVHTFPAVLQSSGL YSLSSVVTVPSSSLGTQTYICNVNHKPSNTKVDKKV EPKSCDKTHTCPPCPAPELLGGPSVFIFPPKPKDVL TITLTPKVTCVVVDISKDDPEVQFSWFVDDVEVHTA QTQPREEQFNSTFRSVSELPIMHQDWLNGKEFKCRV NSAAFPAPIEKTISKTKGRPKAPQVYTIPPPKEQMA KDKVSLTCMITDFFPEDITVEWQWNGQPAENYKNTQ PIMDTDGSYFVYSKLNVQKSNWEAGNTFTCSVLHEG LHNHHTEKSLSHSPGK (SEQ ID NO: 39) |
| Termination codons | TGA in vector |
| Additional features | |
| Preferred Hosts | HEK293 |
| 5' primer for amplification of insert Fwd-HV2 | 5' attcggaggttcagctggtggag 3' (SEQ ID NO: 40) |

TABLE 3-continued

General Data Sheet on pFUSE-HEAVY Vector

| Source | Constructed by Peter Loppnau |
|---|---|
| 3' primer for amplification of insert Rev-HV2 | 5' gagacggtgaccagggttc 3' (SEQ ID NO: 41) |
| 5' sequencing primer pFUSE-FWD | 5' acagatccaagctgtgacc 3' (SEQ ID NO: 42) |
| 3' sequencing primer ScreenSeqRev Heavy | 5' agtagtccttgaccaggcag 3' (SEQ ID NO: 43) |

TABLE 4

General Data Sheet on pFUSE-LIGHT Vector

| Source | Constructed by Peter Loppnau |
|---|---|
| Company | Structural Genomics Consortium, Toronto |
| Descripton | The pFUSE-LIGHT vector is a derivative of the pFUSE2ss-CLIg-mk vector (Invivogen). It is a mammalian expression vector for produc on of human light chain gamma IgG and is used in a co-transfection with pFUSE-HEAVY. The expressed IgG is a hybrid of human FAB from Library E or F, human hinge region, and a mouse Fe region. |
| Antibiotic resistance | Blastocidin S 100 ug/ml from 10 mg/ml stock solution |
| Promoter | hEF1-HTLV composite promoter |
| Cloning Method | Insertion of DNA sequence into the cloning/expression region is preformed using BD-Biosciences Infusion enzyme mediated directional recombination between complementary 15 nucleotide DNA sequences at the ends of the insert (PCR product) and Afe1/Kpn1 linearized vector. Insertion of target sequence involves replacement of a SacB gene staffer sequence, which provides for negative selection of the original plasmid on 5 sucrose. |
| Initiation Codon | ATG in vector |
| N - terminal fusion sequence, IL2 signal peptide | MYRMQLLSCIALSLALVTNSDIQMTQSPSSLSASV GDRVTITCRASQSVSSA---- (SEQ ID NO: 47) |
| C - terminal fusion sequence, identical to human FAB | --GTKVEIKRTVAAPSVFIFPPSDSQLKSGTASVVCLL NNFYPREAKVQWKVDNALQSGNSQESVTEQSK DSTYSLSSTLTLSKADYEKHKVYACEVTHQGLSS PVTKSFNRGEC (SEQ ID NO: 48) |
| Termination codons | TAG in vector |
| Additional features | |
| Prefered Hosts | HEK293 |
| 5' primer for amplification of insert Light Fwd Afe1 | 5' cagtccgtgtccagcgctg 3' (SEQ ID NO: 49) |
| 3' primer for amplification of insert Rev LV2 | 5' tttgatctccaccttggtac 3' (SEQ ID NO: 50) |
| 5' sequencing primer pFUSE-FWD | 5' acagatccaagctgtgacc 3' (SEQ ID NO: 51) |
| 3' sequencing primer SeqscreenRevlight | 5' accttccactgtactttgg 3' (SEQ ID NO: 52) |

(SEQ ID NO: 1)
TYTQCTDGYEWDPVRQQCKDIDE (SEQ ID NO: 2)
TYTQCTDGYEWDPVRQQCRDIDE (SEQ ID NO: 3)
QIQLVQSGPELKKPGETVKISCKASGYSFTTYGMSWVKQAPGKGLKW

MGWINTYSGVPTYADDFKGRFAFFLETSASTAYLQINNLKNEDTATY

FCARWVDYWGQGTTLTVSS (SEQ ID NO: 4)
DIKMTQSPSSMYASLGERVTITCKASQDIKSYLSWHQQKPWKSPKTL

IYYATSLADGVPSRFSGSGSGQDYSLTISSLESDDTATYYCLQHGKS

PYTFGGGTKLEIK (SEQ ID NO: 5)
GYSFTTYGMS (SEQ ID NO: 6)
WINTYSGVPTYADDFKG (SEQ ID NO: 7)
WVDY (SEQ ID NO: 8)
CKASQDIKSYLS (SEQ ID NO: 9)
YATSLAD (SEQ ID NO: 10)
LQHGKSPYT pFUSE-LIGHT WITH VL (MODEL PROTEIN) cDNA
(SEQ ID NO: 19)
ATGCAACTCCTGTCTTGCATTGCACTAAGTCTTGCACTTGTCACGAA
TTCAGATATCCAGATGACCCAGTCCCCGAGCTCCCTGTCCGCCTCTG
TGGGCGATAGGGTCACCATCACCTGCCGTGCCAGTCAGTCCGTGTCC
AGCGCTGACATCAAGATGACCCAGTCTCCATCCTCCATGTATGCATC
GCTGGGAGAGAGAGTCACTATCACTTGCAAGGCGAGTCAGGACATTA
AAAGCTATTTAAGCTGGCACCAGCAGAAACCATGGAAATCTCCTAAG
ACCCTGATCTATTATGCAACAAGCTTGGCAGATGGGGTCCCATCAAG
ATTCAGTGGCAGCGGATCTGGGCAAGATTATTCTCTAACCATCAGCA
GCCTGGAGTCTGACGATACAGCAACTTATTACTGTCTACAGCATGGT
AAGAGCCCGTACACGTTCGGAGGGGGGACCAAGCTGGAAATAAAAGG
TACCAAGGTGGAGATCAAACGAACTGTGGCTGCACCATCTGTCTTCA
TCTTCCCGCCATCTGATTCACAGTTGAAATCTGGAACTGCCTCTGTT
GTGTGCCTGCTGAATAACTTCTATCCCAGAGAGGCCAAAGTACAGTG
GAAGGTGGATAACGCCCTCCAATCGGGTAACTCCCAGGAGAGTGTCA
CAGAGCAGGACAGCAAGGACAGCACCTACAGCCTCAGCAGCACCCTG
ACGCTGAGCAAAGCAGACTACGAAAAACATAAAGTCTACGCCTGCGA
AGTCACCCATCAGGGCCTGAGCTCGCCCGTCACAAAGAGCTTCAACA
GGGGAGAGTGTTAG pFUSE-LIGHT WITH VL Protein sequence
(SEQ ID NO: 23)
MQLLSCIALSLALVTNSDIQMTQSPSSLSASVGDRVTITCRASQSVS
SADIKMTQSPSSMYASLGERVTITCKASQDIKSYLSWHQQKPWKSPK
TLIYYATSLADGVPSRFSGSGSGQDYSLTISSLESDDTATYYCLQHG
KSPYTFGGGTKLEIKGTKVEIKRTVAAPSVFIFPPSDSQLKSGTASV
VCLLNNFYPREAKVQWKVDNALQSGNSQESVTEQDSKDSTYSLSSTL
TLSKADYEKHKVYACEVTHQGLSSPVTKSFNRGEC pFUSE-HEAVY WITH VH (MODEL PROTEIN) cDNA
(SEQ ID NO: 20)
ATGTACAGGATGCAACTCCTGTCTTGCATTGCACTAAGTCTTGCACT
TGTCACGAATTCGGAGGTTCAGCTGGTGGAGCAGATCCAGTTGGTAC
AGTCTGGACCTGAGTTGAAGAAGCCTGGAGAGACAGTCAAGATCTCC
TGCAAGGCTTCTGGATATAGTTTCACAACCTATGGAATGAGCTGGGT
GAAACAGGCTCCAGGAAAGGGTTTAAAGTGGATGGCTGGATAAACA
CCCACTCTGGAGTGCCAACATATGCTGATGACTTCAAGGGACGGTTT
GCCTTCTTTTTGGAAACCTCTGCCAGCACTGCCTATTTGCAGATCAA
TAACCTCAAAAATGAGGACACGGCTACATATTTCTGTGCAAGATGGG
TTGACTACTGGGGCCAAGGCACCACTCTCACAGTCTCCTCAGGAACC
CTGGTCACCGTCTCCTCGGCCTCCACCAAGGGTCCATCGGTCTTCCC
CCTGGCACCCTCCTCCAAGAGCACCTCTGGGGGCACAGCGGCCCTGG
GCTGCCTGGTCAAGGACTACTTCCCCGAACCGGTGACGGTGTCGTGG
AACTCAGGCGCCCTGACCAGCGGCGTGCACACCTTCCCGGCTGTCCT
ACAGTCCTCAGGACTCTACTCCCTCAGCAGCGTGGTGACCGTGCCCT
CCAGCAGCTTGGGCACCCAGACCTACATCTGCAACGTGAATCACAAG
CCCAGCAACACCAAGGTCGACAAGAAAGTTGAGCCCAAATCTTGTGA
CAAAACTCACACATGCCCTCCATGTCCAGCCCCTGAACTTCTGGGAG
GACCTTCTGTCTTCATCTTCCCCCCAAAGCCCAAGGATGTGCTCACC
ATTACTCTGACTCCTAAGGTCACGTGTGTTGTGGTAGACATCAGCAA
GGATGATCCCGAGGTCCAGTTCAGCTGGTTTGTAGATGATGTGGAGG
TGCACACAGCTCAGACGCAACCCCGGGAGGAGCAGTTCAACAGCACT
TTCCGCTCAGTCAGTGAACTTCCCATCATGCACCAGGACTGGCTCAA
TGGCAAGGAGTTCAAATGCAGGGTCAACAGTGCAGCTTTCCCTGCCC
CCATCGAGAAACCATCTCCAAAACCAAAGGCAGACCGAAGGCTCCA
CAGGTGTACACCATTCCACCTCCCAAGGAGCAGATGGCCAAGGATAA
AGTCAGTCTGACCTGCATGATAACAGACTTCTTCCCTGAAGACATTA
CTGTGGAGTGGCAGTGGAATGGGCAGCCAGCGGAGAACTACAAGAAC
ACTCAGCCCATCATGGACACAGATGGCTCTTACTTCGTCTACAGCAA
GCTCAATGTGCAGAAGAGCAACTGGGAGGCAGGAAATACTTTCACCT
GCTCTGTGTTACATGAGGGCCTGCACAACCACCATACTGAGAAGAGC
CTCTCCCACTCTCCTGGTAAATGA pFUSE-HEAVY WITH VH, Protein sequence
(SEQ ID NO: 24)
MYRMQLLSCIALSLALVTNSEVQLVEQIQLVQSGPELKKPGETVKIS
CKASGYSFTTYGMSWVKQAPGKGLKWMGWINTHSGVPTYADDFKGRF
AFFLETSASTAYLQINNLKNEDTATYFCARWVDYWGQGTTLTVSSGT
LVTVSSASTKGPSVFPLAPSSKSTSGGTAALGCLVKDYFPEPVTVSW
NSGALTSGVHTFPAVLQSSGLYSLSSVVTVPSSSLGTQTYICNVNHK
PSNTKVDKKVEPKSCDKTHTCPPCPAPELLGGPSVFIFPPKPKDVLT
ITLTPKVTCVVVDISKDDPEVQFSWFVDDVEVHTAQTQPREEQFNST
FRSVSELPIMHQDWLNGKEFKCRVNSAAFPAPIEKTISKTKGRPKAP
QVYTIPPPKEQMAKDKVSLTCMITDFFPEDITVEWQWNGQPAENYKN
TQPIMDTDGSYFVYSKLNVQKSNWEAGNTFTCSVLHEGLHNHHTEKS
LSHSPGK scFv428 OPTIMIZED PROKARYOTIC SEQUENCE, cDNA:
(SEQ ID NO: 21)
ATGAAATACCTGCTGCCGACCGCTGCTGCTGGTCTGCTGCTCCTCGC
TGCCCAGCCGGCGATGGCCGATATTAAAATGACGCAGTCTCCGAGCA
GTATGTACGCAAGCCTGGGTGAACGTGTGACGATTACCTGTAAAGCC
TCTCAAGATATCAAATCCTATCTGTCATGGCATCAGCAAAAACCGTG
GAAAAGCCCGAAAACCCTGATTTATTACGCAACGTCACTGGCTGATG
GCGTGCCGTCGCGTTTTTCAGGTTCGGGCAGCGGTCAGGATTATAGC
CTGACCATCAGCTCTCTGGAATCTGATGACACCGCGACGTATTACTG
CCTGCAACACGGTAAAAGCCCGTACACCTTCGGCGGTGGCACGAAAC
TGGAAATTAAAGGTGGCGTGGCTCTGGTGGCGGTGGCAGTGGTGGC
GGTGGCTCCCAGATCCAACTGGTTCAGAGTGGCCCGGAACTGAAAAA

```
ACCGGGTGAAACCGTGAAAATTTCCTGTAAAGCGTCGGGCTATAGCT

TTACCACGTACGGTATGAGTTGGGTTAAACAGGCCCCGGGCAAAGGT

CTGAAATGGATGGGCTGGATCAACACCTATTCTGGTGTCCCGACGTA

CGCAGATGACTTTAAAGGCCGTTTCGCGTTTTTCCTGGAAACCTCTG

CGAGTACGGCCTATCTGCAGATCAACAACCTGAAAAACGAAGATACC

GCGACGTATTTCTGCGCACGTTGGGTGGACTACTGGGGTCAAGGTAC

CACGCTGACCGTTAGTTCCGAACAAAAACTGATTAGTGAAGAAGACC

TGAATATGCACACGGGCCACCACCACCACCACCATTAA scFv428 OPTIMIZED PROKARYOTIC SEQUENCE, Protein
sequence:
                                            (SEQ ID NO: 25)
MKYLLPTAAAGLLLLAAQPAMADIKMTQSPSSMYASLGERVTITCKA

SQDIKSYLSWHQQKPWKSPKTLIYYATSLADGVPSRFSGSGSGQDYS

LTISSLESDDTATYYCLQHGKSPYTFGGGTKLEIKGGGGSGGGGSGG

GGSQIQLVQSGPELKKPGETVKISCKASGYSFTTYGMSWVKQAPGKG

LKWMGWINTYSGVPTYADDFKGRFAFFLETSASTAYLQINNLKNEDT

ATYFCARWVDYWGQGTTLTVSSEQKLISEEDLNMHTGHHHHHH scFv428 OPTIMIZED EUKARYOTIC SEQUENCE, cDNA
                                            (SEQ ID NO: 22)
ATGGAAACCGATACACTGCTGCTGTGGGTCCTGCTGCTGTGGGTGCC

CGGGTCAACTGGCGATGACATCAAGATGACACAGAGTCCCTCTAGTA

TGTACGCATCACTGGGCGAGAGGGTGACCATCACATGTAAAGCCTCT

CAGGATATTAAGAGTTATCTGTCATGGCACCAGCAGAAGCCCTGGAA

AAGCCCTAAGACACTGATCTACTATGCAACTAGCCTGGCAGACGGAG

TCCCATCCCGGTTCAGTGGGTCAGGAAGCGGCCAGGATTACTCTCTG

ACCATTTCAAGCCTGGAAAGTGACGATACTGCCACCTACTATTGTCT

GCAGCATGGCAAGAGCCCTTATACCTTTGGCGGGGGAACAAAACTGG

AGATCAAGGGCGGAGGAGGCAGCGGAGGAGGAGGGTCCGGAGGAGGA

GGATCTCAGATTCAGCTGGTCCAGAGCGGCCCAGAGCTGAAGAAACC

CGGGGAAACCGTGAAAATCAGCTGCAAGGCTTCCGGGTACTCTTTCA

CCACATATGGAATGTCCTGGGTCAAGCAGGCACCTGGCAAGGGGCTG

AAATGGATGGGCTGGATTAACACTTACTCCGGGGTGCCAACCTATGC

CGACGATTTCAAAGGCCGGTTTGCTTTCTTTCTGGAGACATCCGCCT

CTACTGCTTACCTGCAGATCAACAATCTGAAGAATGAAGACACAGCT

ACTTACTTTTGCGCAAGATGGGTGGATTATTGGGACAGGGAACTAC

CCTGACCGTCAGCTCCGAACAGAAACTGATTTCCGAGGAGGACCTGA

ACATGCACACTGGGCACCACCACCACCACCACTAA scFv428 OPTIMIZED EUKARYOTIC SEQUENCE, Protein
sequence:
                                            (SEQ ID NO: 26)
METDTLLLWVLLLWVPGSTGDDIKMTQSPSSMYASLGERVTITCKAS

QDIKSYLSWHQQKPWKSPKTLIYYATSLADGVPSRFSGSGSGQDYSL

TISSLESDDTATYYCLQHGKSPYTFGGGTKLEIKGGGGSGGGGSGGG

GSQIQLVQSGPELKKPGETVKISCKASGYSFTTYGMSWVKQAPGKGL

KWMGWINTYSGVPTYADDFKGRFAFFLETSASTAYLQINNLKNEDTA

TYFCARWVDYWGQGTTLTVSSEQKLISEEDLNMHTGHHHHHH
```

Antibody variable region sequencing for 328.2.3C11.H11.G3 hybridoma

VH CDR Sequences:

```
cag atc cag ttg gta cag tct gga cct gag
 Q   I   Q   L   V   Q   S   G   P   E ttg aag aag cct gga gag aca gtc aag atc
 L   K   K   P   G   E   T   V   K   I tcc tgc aag gct tct gga tat agt ttc aca
 S   C   K   A   S   G   Y   S   F   T acc tat gga atg agc tgg gtg aaa cag gct
 T   Y   G   M   S   W   V   K   Q   A cca gga aag ggt tta aag tgg atg ggc tgg
 P   G   K   G   L   K   W   M   G   W ata aac acc tac tct gga gtg cca aca tat
 I   N   T   Y   S   G   V   P   T   Y gct gat gac ttc aag gga cgg ttt gcc ttc
 A   D   D   F   K   G   R   F   A   F ttt ttg gaa acc tct gcc agc act gcc tat
 F   L   E   T   S   A   S   T   A   Y ttg cag atc aat aac ctc aaa aat gag gac
 L   Q   I   N   N   L   K   N   E   D acg gct aca tat ttc tgt gca aga tgg gtt
 T   A   T   Y   F   C   A   R   W   V gac tac tgg ggc caa ggc acc act ctc aca
 D   Y   W   G   Q   G   T   T   L   T gtc tcc tca (SEQ ID NO: 11)
 V   S   S  (SEQ ID NO: 3)
```

| CDR | Nucleotide sequence | Protein Sequence | # of AA residues |
|---|---|---|---|
| VH CDR-1 | ggatatagtttcaca acctatggaatgagc (SEQ ID NO: 13) | GYSFTTYGMS (SEQ ID NO: 5) | 10 |
| VH CDR-2 | tggataaacacctac tctggagtgccaaca tatgctgatgacttc aaggga (SEQ ID NO: 14) | WINTYSGVPTYADD FKG (SEQ ID NO: 6) | 17 |
| VH CDR-3 | tgggttgactac (SEQ ID NO: 15) | WVDY (SEQ ID NO: 7) | 4 |

VL CDR Sequences:

```
gac atc aag atg acc cag tct cca tcc tcc
 D   I   K   M   T   Q   S   P   S   S atg tat gca tcg ctg gga gag aga gtc act
 M   Y   A   S   L   G   E   R   V   T atc act tgc aag gcg agt cag gac att aaa
 I   T   C   K   A   S   Q   D   I   K agc tat tta agc tgg cac cag cag aaa cca
 S   Y   L   S   W   H   Q   Q   K   P
```

```
tgg aaa tct cct aag acc ctg atc tat tat
 W   K   S   P   K   T   L   I   Y   Y gca aca agc ttg gca gat ggg gtc cca tca
 A   T   S   L   A   D   G   V   P   S aga ttc agt ggc agc gga tct ggg caa gat
 R   F   S   G   S   G   S   G   Q   D tat tct cta acc atc agc agc ctg gag tct
 Y   S   L   T   I   S   S   L   E   S gac gat aca gca act tat tac tgt cta cag
 D   D   T   A   T   Y   Y   C   L   Q cat ggt aag agc ccg tac acg ttc gga ggg
 H   G   K   S   P   Y   T   F   G   G
```

```
ggg acc aag ctg gaa ata aaa (SEQ ID NO: 12)
 G   T   K   L   E   I   K  (SEQ ID NO: 4)
```

| CDR | Nucleotide sequence | Protein Sequence | # of AA residues |
|---|---|---|---|
| VL CDR-1 | tgcaaggcgagtcag gacattaaaagctat ttaagc (SEQ ID NO: 16) | CKASQDIKSYLS (SEQ ID NO: 8) | 12 |
| VL CDR-2 | tatgcaacaagcttg gcagat (SEQ ID NO: 17) | YATSLAD (SEQ ID NO: 9) | 7 |
| VL CDR-3 | ctacagcatggtaag agcccgtacacg (SEQ ID NO: 18) | LQHGKSPYT (SEQ ID NO: 10) | 9 |

What is claimed:

1. A T-cell or a Natural Killer (NK) cell comprising a chimeric antigen receptor (CAR) protein comprising an antigen-binding region of an anti-Fibulin-3 monoclonal antibody, the antigen-binding region comprising the amino acid sequences SEQ ID NO: 5-10.

2. The T cell or the NK cell of claim 1, wherein the CAR protein is labeled with an agent.

3. The T cell or the NK cell of claim 2, wherein the agent is selected from the group consisting of a radioisotope, fluorescent compound, bioluminescent compound, chemiluminescent compound, metal chelator, and enzyme.

4. The T cell or the NK cell of claim 2, wherein the agent is a cytotoxic or a therapeutic agent.

5. The T cell or the NK cell of claim 4, wherein the cytotoxic agent is selected from the group consisting of ricin, ricin A-chain, doxorubicin, daunorubicin, taxol, ethidium bromide, mitomycin, etoposide, teniposide, vincristine, vinblastine, colchicine, dihydroxy anthracenedione, actinomycin, diphtheria toxin, *Pseudomonas* exotoxin (PE) A, PE40, abrin, abrin A chain, modeccin A chain, alpha-sarcin, gelonin, mitogellin, phenomycin, enomycin, curicin, calicheamicin, *Saponaria officinalis* inhibitor, and glucocorticoid.

6. The T cell or the NK cell of claim 3, wherein the radioisotope is selected from the group consisting of $^{212}$Bi, $^{131}$I, $^{131}$In, $^{90}$Y, and $^{186}$Re.

7. A composition comprising a population of T cells or Natural Killer cells of claim 1.

8. The composition of claim 7 further comprising a pharmaceutically acceptable excipient.

9. The T cell or the NK cell of claim 1, wherein the anti-Fibulin-3 monoclonal antibody is mAb428.3C11.

* * * * *